(12) United States Patent
Purkayastha et al.

(10) Patent No.: US 8,362,242 B2
(45) Date of Patent: Jan. 29, 2013

(54) ANALYTE DETERMINATION UTILIZING MASS TAGGING REAGENTS COMPRISING A NON-ENCODED DETECTABLE LABEL

(75) Inventors: Subhasish Purkayastha, Acton, MA (US); Subhakar Dey, North Billerica, MA (US)

(73) Assignee: DH Technologies Development PTE. Ltd., Singapore (SG)

( * ) Notice: Subject to any disclaimer, the term of this patent is extended or adjusted under 35 U.S.C. 154(b) by 1460 days.

(21) Appl. No.: 11/769,890

(22) Filed: Jun. 28, 2007

(65) Prior Publication Data

US 2011/0028685 A1 Feb. 3, 2011

Related U.S. Application Data

(60) Provisional application No. 60/818,007, filed on Jun. 30, 2006.

(51) Int. Cl.
*C07D 241/04* (2006.01)
(52) U.S. Cl. .................................................... 544/230
(58) Field of Classification Search .................. None
See application file for complete search history.

(56) References Cited

U.S. PATENT DOCUMENTS

| 5,705,610 | A | 1/1998 | Zuckermann et al. |
| 5,800,992 | A | 9/1998 | Fodor et al. |
| 6,027,890 | A | 2/2000 | Ness et al. |
| 6,270,976 | B1 | 8/2001 | Schmidt et al. |
| 6,287,780 | B1 | 9/2001 | Schmidt et al. |
| 6,475,807 | B1 | 11/2002 | Geysen et al. |

FOREIGN PATENT DOCUMENTS

| WO | WO 98/31830 A | 7/1998 |
| WO | WO 2004/019000 A | 3/2004 |
| WO | WO 2004/070352 A | 8/2004 |
| WO | WO 2005/068446 A | 7/2005 |
| WO | WO 2006/063167 | * 6/2006 |

OTHER PUBLICATIONS

Byrn et al. Solid-State Chemistry of Drugs, 2nd ed. Chapter 11, "Hydrates and Solvates," p. 233-247.*
Byrn et al. Solid-State Chemistry of Drugs, $2^{nd}$ ed. (1999) Chapter 11, "Hydrates and Solvates," p. 233-247.*
Bottari P et al: "Design and Synthesis of Visible Isotope-Coded Affinity Tags for the Absolute Quantification of Specific proteins in Complex Mixtures" Bioconjugate Chemistry, ACS, Washington, D.C., U.S. vol. 15, No. 2, Feb. 21, 2004, pp. 380-388.
Dunayevskiy, Yuriy M.: "Application of Capillary Electrophoresis-Electrospray ionization Mass Spectrometry in the Determination of Molecular Diversity"; PNAS 1996, Proc. Natl. Acad. Sci. USA 93—Boston, MA, Jan. 30, 1996, pp. 6152-6157.
Gygi S P et al: "Quantitative Analysis of Complex Protein Mixtures using Isotope-Coded Affinity Tags" Nature Biotechnology, nature Publishing Group, New York, NY, U.S. vol. 17, No. 10, Oct. 1, 1999, pp. 994-999.

* cited by examiner

*Primary Examiner* — Rebecca L. Anderson
*Assistant Examiner* — Alicia L Otton

(57) ABSTRACT

This invention pertains to methods, mixtures, kits and compositions pertaining to analyte determination and/or quantification by mass spectrometry using compounds comprising a reporter moiety and a non-encoded detectable label. The compounds can be used in sets for the analysis of mixtures of labeled analytes.

2 Claims, 23 Drawing Sheets

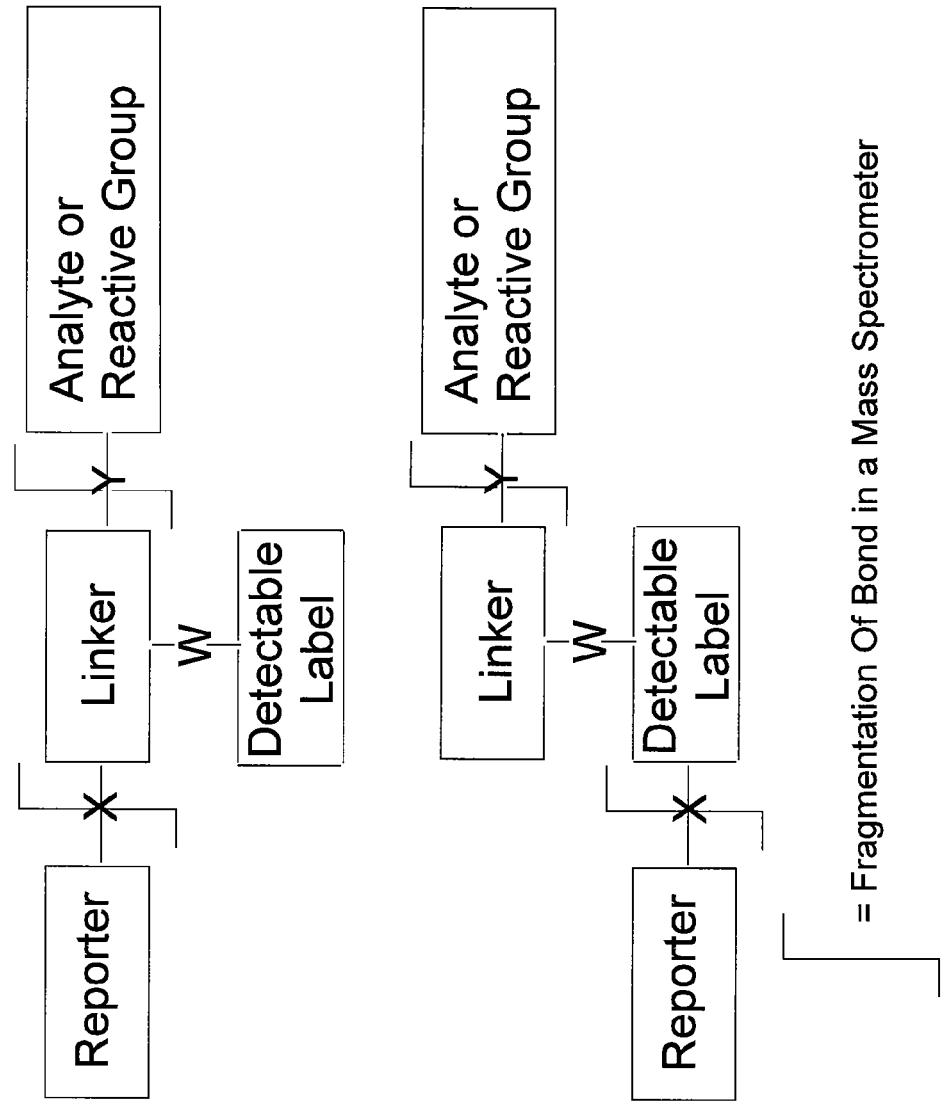

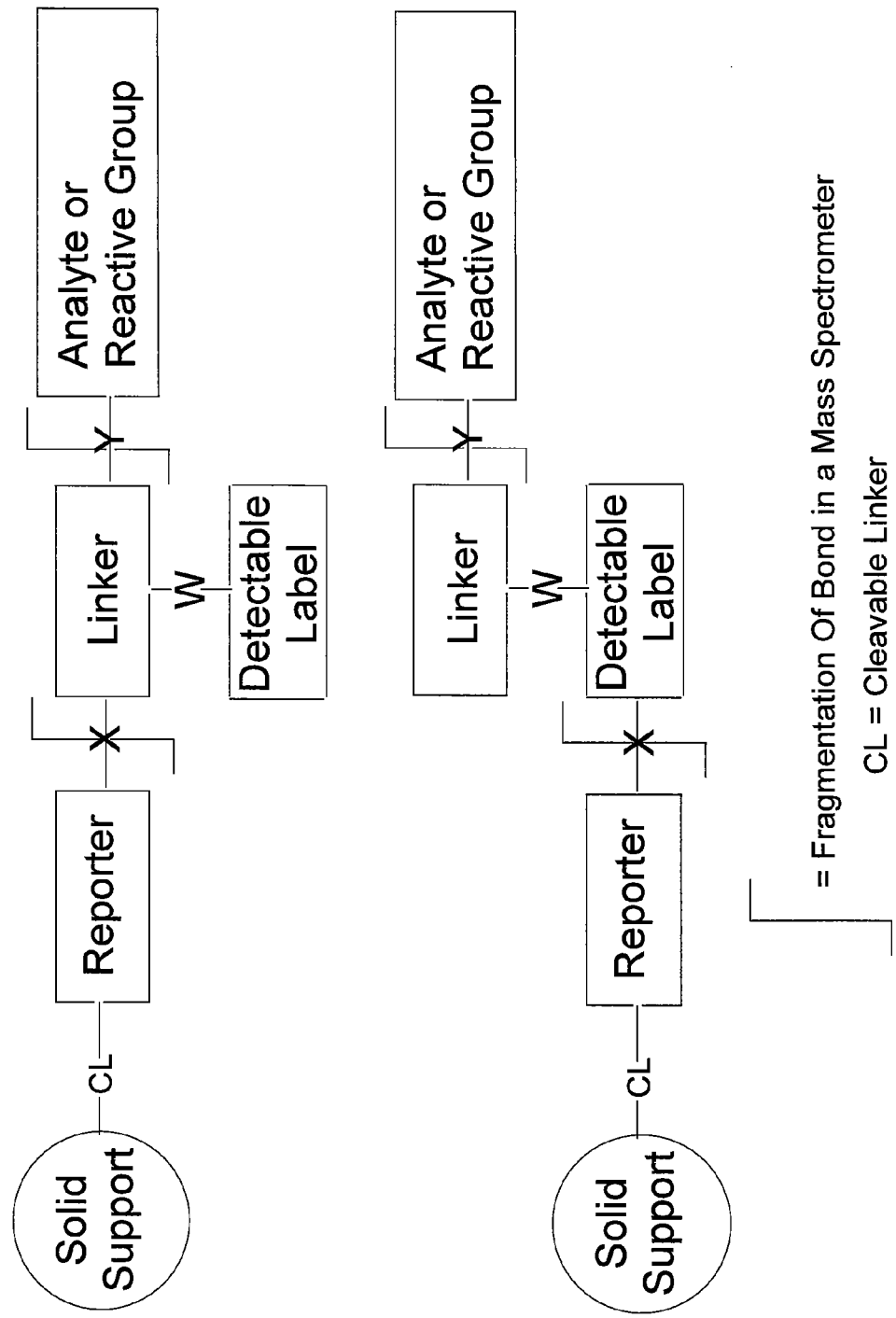

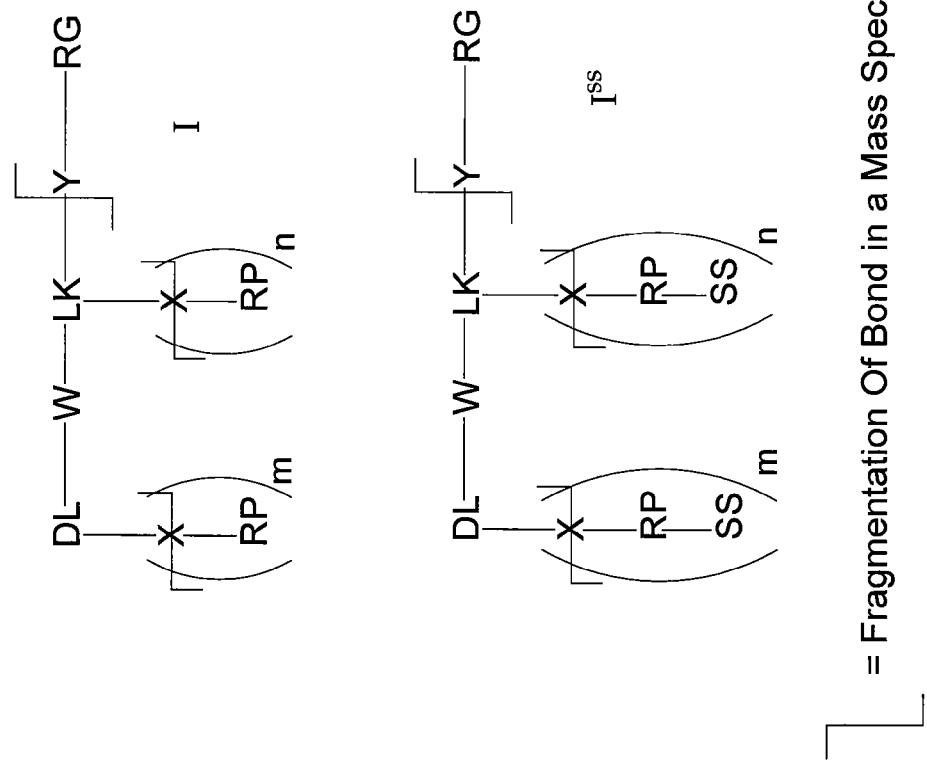

Various Labeling Reagents With Certain Fragmentations Illustrated

⌐ = Fragmentation Of Bond in a Mass Spectrometer

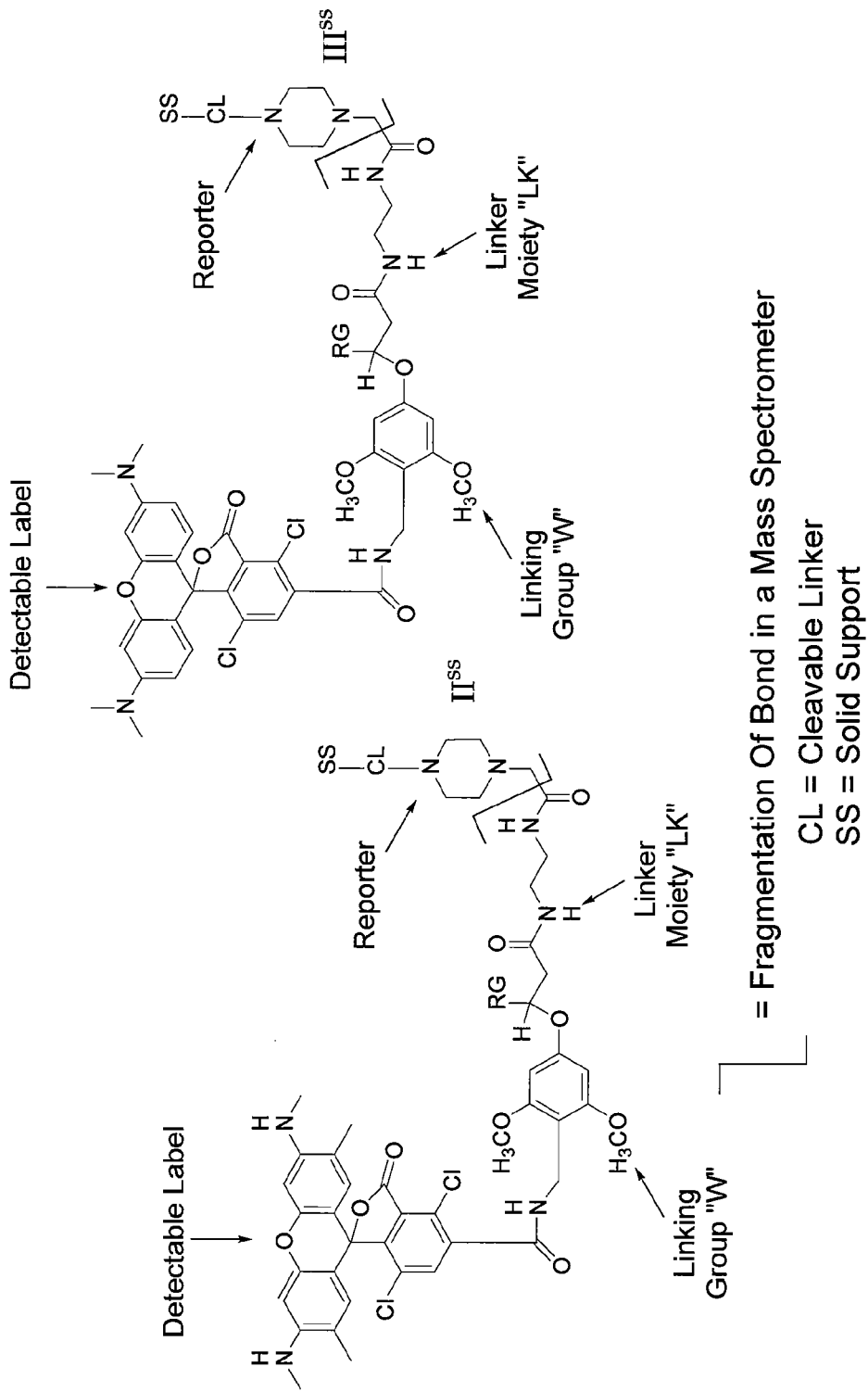
FIG. 2c Various Labeled Analytes With Certain Fragmentations Illustrated Generic Formula of Various Labeled Analytes With Certain Fragmentations Illustrated Various Labeled Analytes With Certain Fragmentations Illustrated ⌐ = Fragmentation Of Bond in a Mass Spectrometer Various Support Bound Labeled Analytes With Certain Fragmentations Illustrated ⌐ = Fragmentation Of Bond in a Mass Spectrometer
CL = Cleavable Linker
SS = Solid Support Various Labeled Analytes Released From A Solid Support With Certain Fragmentations Illustrated = Fragmentation Of Bond in a Mass Spectrometer Q' = Functional Group Released From The Cleavable Linker

FIG. 4a
Exemplary Isobars
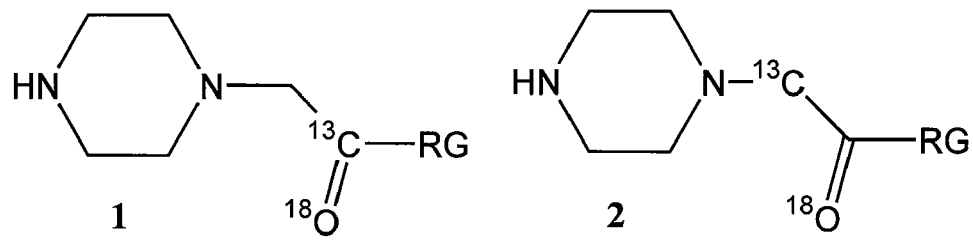
Mass Of Compounds 1 and 2 = 130.095
Mass Of Compounds 3 and 4 = 130.085
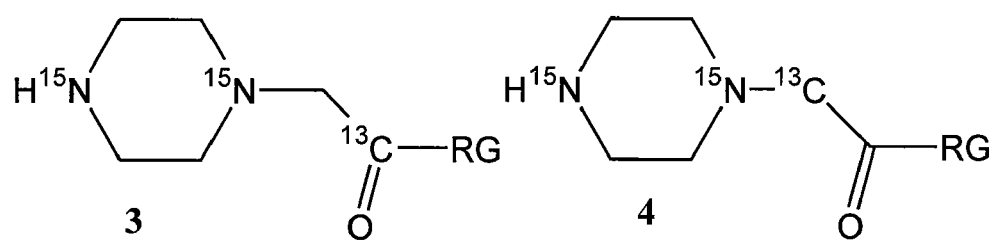
Fig. 4b
Exemplary Isomeric Isobars
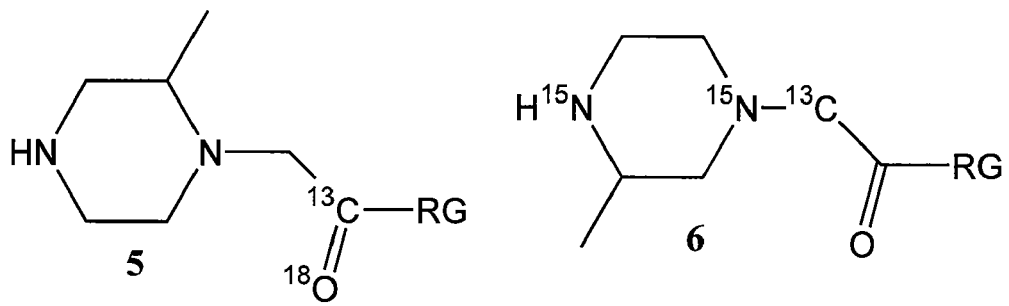
Mass of Compound 5 = 144.111
Mass of Compound 6 = 144.100
Notes: RG = Reactive Group
The Mass Stated Is Only For The
Reporter/Linker Combination where the linker moiety
is the carbonyl group and no detectable label is shown

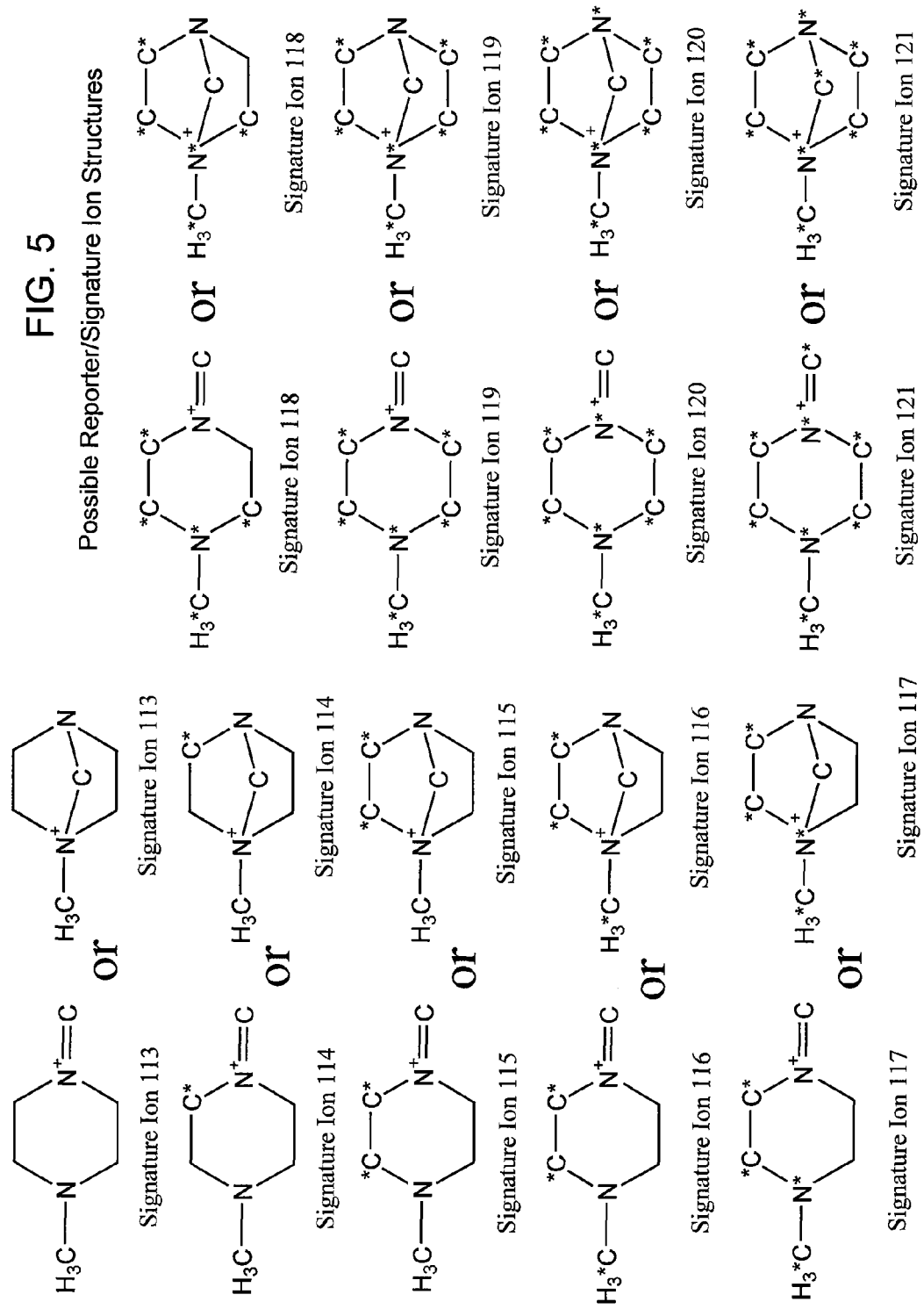

Scheme For The Synthesis Of Various Active Esters

FIG. 8a
Possible Isotopic Coding For Labeling Reagents II and III
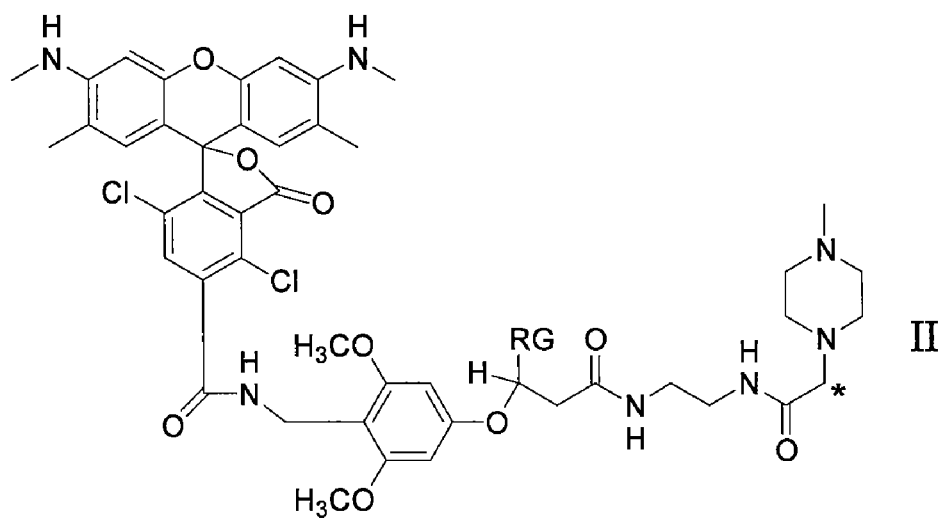
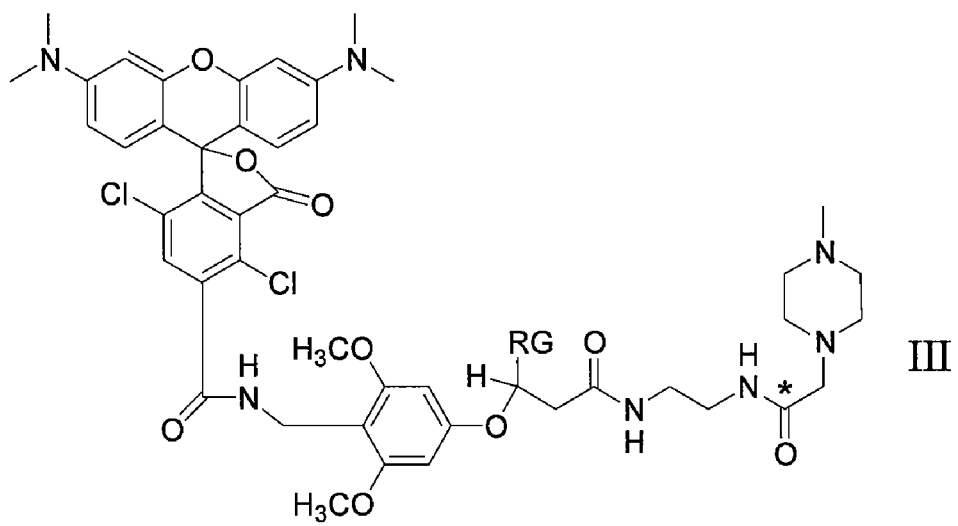
* indicates where $^{13}C$ is substituted for $^{12}C$

FIG. 8b
Possible Isotopic Coding For Support Bound Labeling Reagents II$^{ss}$ and III$^{ss}$
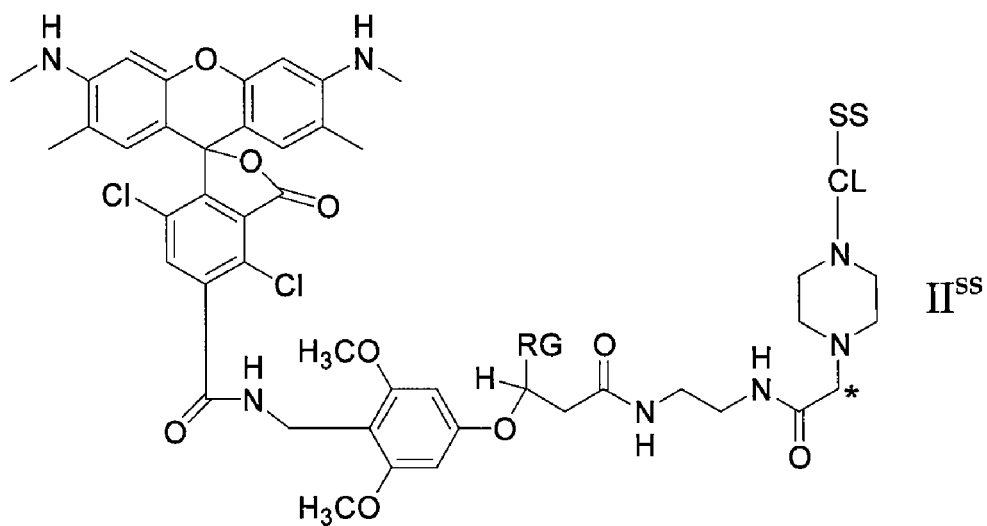
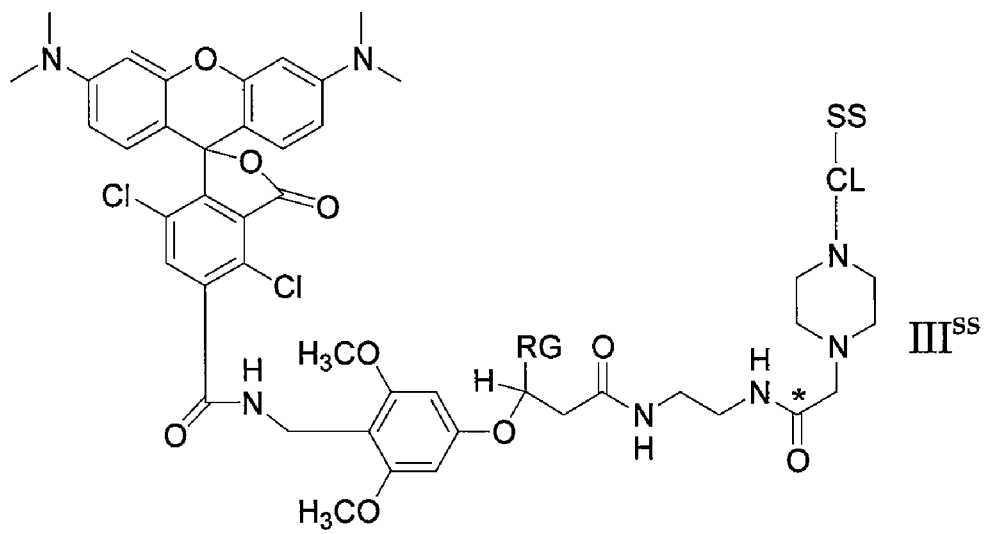
* indicates where $^{13}C$ is substituted for $^{12}C$ Proposed Synthetic Route To Labeling Reagent III Proposed Synthetic Route To Labeling Reagent III

ANALYTE DETERMINATION UTILIZING MASS TAGGING REAGENTS COMPRISING A NON-ENCODED DETECTABLE LABEL

PRIORITY AND RELATED APPLICATIONS

This application claims the benefit of U.S. Provisional Patent Application Ser. No. 60/818,007 filed Jun. 30, 2006, incorporated herein by reference.

The section headings used herein are for organizational purposes only and should not be construed as limiting the subject matter described herein in any way.

FIELD

This invention pertains to methods, mixtures, kits and compositions pertaining to analyte determination using mass spectrometry techniques.

INTRODUCTION

This invention pertains the determination of an analyte or analytes by mass analysis. In various embodiments, the mass spectrometric analysis can be coupled with an electrophoretic separations technique. An analyte can be any molecule of interest. Non-limiting examples of analytes (natural and/or synthetic) include, but are not limited to, proteins, peptides, nucleic acids, carbohydrates, lipids, amino acids, vitamins, steroids, prostaglandins and/or other small molecules having a mass of less than 1500 daltons (Da). Analytes can be determined using unique labeling reagents that permit the relative and/or absolute quantification of the analytes in complex mixtures. The labeling reagents can be used in isomeric and/or isobaric sets for the analysis of complex sample mixtures wherein the labeling reagents can be isomeric and/or isobaric.

Isomeric and/or isobaric labeling reagents comprising a reporter moiety, a balance (or linker) moiety and a reactive group, wherein the reactive group can be substituted by the analyte in the analyte reacted form of the composition, are known. Examples of labeling reagents and labeled analytes comprising these three elements have been disclosed in, for example, published copending and commonly owned U.S. Patent Application Serial Nos. US 2004-0219685 A1, US 2005-0114042 A1, US 2005-0147982 A1, US 2005-0147985 A1, US 2005-0147987 A1, US 2005-0148771 A1, US 2005-0148773 A1 and US 2005-0148774 A1. Sets of isomeric and/or isobaric labeling reagents can be used to label, for example, the analytes of two or more different samples wherein the different labeling reagents of a set all have the same gross mass but wherein each reporter moiety can be uniquely encoded such that each reporter moiety of the set has a unique gross mass and produces a corresponding signature ion of unique gross mass. Because all the reagents of the set can have the same gross mass but can comprise a reporter moiety of unique gross mass, the balance (or linker) will generally (but not necessarily) also comprise one or more heavy atom isotopes to thereby "balance" the mass of each unique reporter such that the reporter/linker combination of each labeling reagent of the set has the same gross mass.

Described herein are new labeling reagents that can be used in isomeric and/or isobaric sets, wherein the labeling reagents comprise a non-encoded detectable label. FIG. 1a illustrates the elements of exemplary labeling reagents (and labeled analytes) of this invention and some information about possible fragmentation characteristics of the molecules in a mass spectrometer. As illustrated, the linker moiety can either connect the elements of the labeling reagent (or labeled analyte) in a linear or a branched mode. When used in isomeric and/or isobaric sets, various non-encoded detectable labels of the labeling reagents of a set can all: 1) be independently detectable; 2) comprise the same gross mass; and 3) comprise the same net charge. Accordingly, the labeling reagents disclosed herein can comprise both a moiety that can be independently detected by non-mass spectrometry methods as well as a different moiety that can be independently detected in a mass spectrometer. In particular, the novel labeling reagents described herein can be used, for example, in electrophoretic separations processes combined with mass spectrometric analysis wherein the properties of the non-encoded detectable labels can be used to locate and/or quantify mixtures of labeled analytes during and/or after the electrophoretic separation and wherein mass spectrometry can be used to identify and/or quantify the analytes of interest in a sample or samples, or fractions thereof.

In some embodiments, the labeling reagents and/or labeled analytes can be support-bound. FIG. 1b illustrates the elements of exemplary support-bound labeling reagents (and support-bound labeled analytes) of this invention and some information about the fragmentation characteristics of the molecules in a mass spectrometer. As illustrated, the linker moiety can either connect the elements of the support-bound labeling reagent (or support-bound labeled analyte) in a linear or a branched mode.

Embodiments of this invention are particularly well suited for the multiplex analysis of complex sample mixtures. For example, some embodiments of this invention can be used in proteomic analysis and/or genomic analysis as well as for correlation studies related to genomic and/or proteomic analysis. Some embodiments of this invention can be used for small molecule analysis, such as for lipid, steroid, vitamin, prostaglandins and/or amino acid analysis. Experimental analysis for which the isomeric and/or isobaric reagents can be used includes, but is not limited to, time course studies, biomarker analysis, multiplex proteomic analysis, mudpit experiments, affinity pull-downs, determination of post-translational modifications (PTMs) (see for example published United States Patent Application No. US 2005-0208550 A1) and multiple control experiments.

DRAWINGS

The skilled artisan will understand that the drawings, described below, are for illustration purposes only. The drawings are not intended to limit the scope of the present teachings in any way.

FIG. 1a is an illustration of the various fragmentation characteristics of exemplary labeling reagents represented in the form of their elements.

FIG. 1b is an illustration of the certain fragmentation characteristics of exemplary support-bound labeling reagents represented in the form of their elements.

FIG. 2a is an illustration of the certain fragmentation characteristics of various labeling reagents represented by a generic formula.

FIG. 2c is an illustration of the certain fragmentation characteristics of various labeling reagents.

FIG. 4a is an illustration of exemplary isobaric compounds.

FIG. 4b is an illustration of exemplary isomeric isobaric compounds.

FIG. 5 is an illustration of various possible reporter ions (signature ions) that can be generated from certain N-methyl piperazine based reporter moieties.

FIG. 8a is an illustration of a possible isotopic coding strategy for labeling reagents of formulas II and III.

FIG. 8b is an illustration of a possible isotopic coding strategy for labeling reagents of formulas $II^{ss}$ and $III^{ss}$.

Figure 2B:
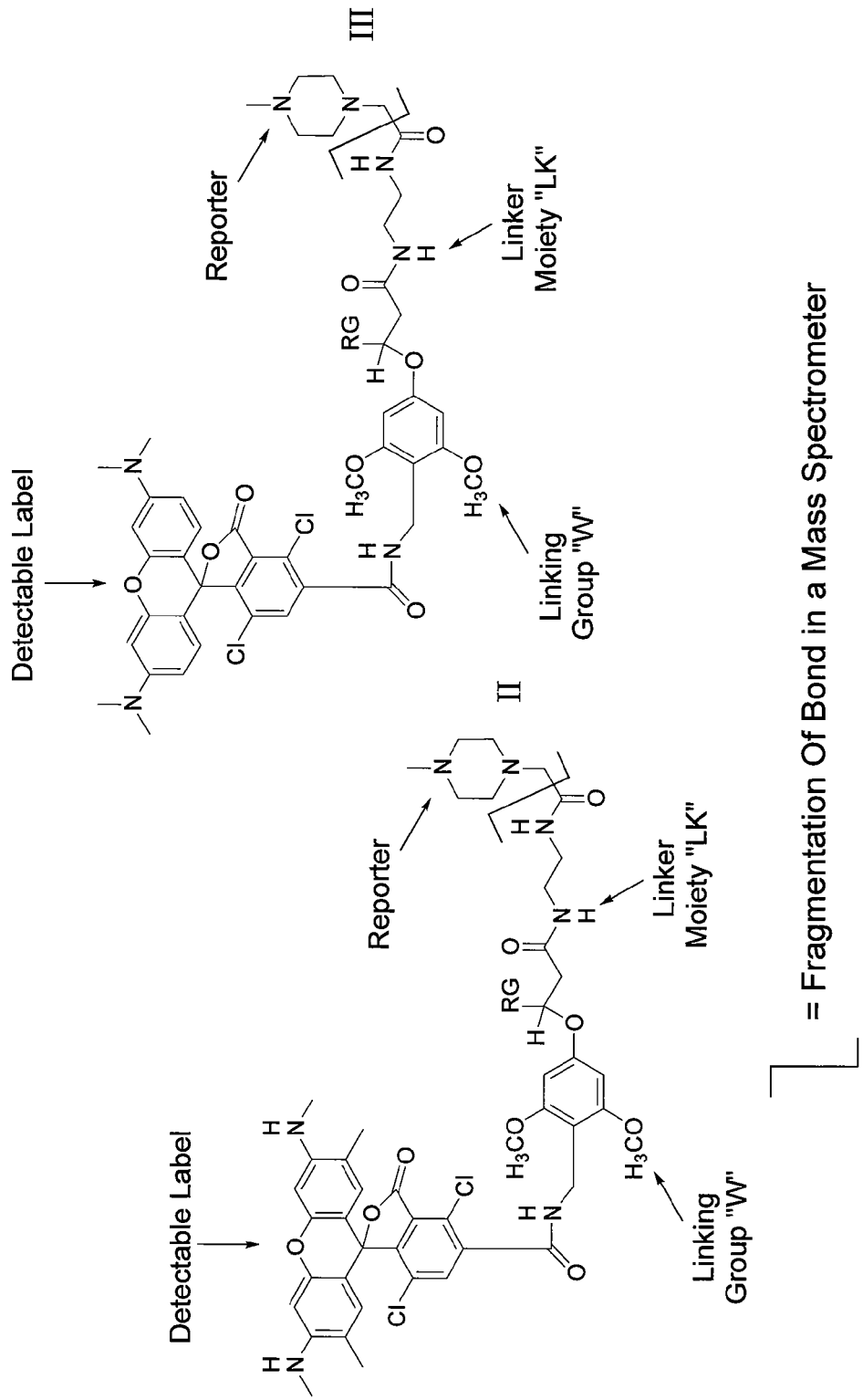
FIG. 2b is an illustration of the certain fragmentation characteristics of various labeling reagents.

All literature and similar materials cited in this application, including but not limited to, patents, patent applications, articles, books, treatises, and internet web pages, regardless of the format of such literature and similar materials, are expressly incorporated by reference herein in their entirety for any and all purposes.

DEFINITIONS

For the purposes of interpreting this specification, the following definitions will apply and whenever appropriate, terms used in the singular will also include the plural and vice versa. In the event that any definition set forth below conflicts with the usage of that word in any other document, including any document incorporated herein by reference, the definition set forth below shall always control for purposes of interpreting this specification and its associated claims unless a contrary meaning is clearly intended (for example in interpreting the document where the term is originally used). The use of "or" herein means "and/or" unless stated otherwise or where the use of "and/or" is clearly inappropriate. The use of "a" herein means "one or more" unless stated otherwise or where the use of "one or more" is clearly inappropriate. The use of "comprise," "comprises," "comprising" "include," "includes," and "including" are interchangeable and not intended to be limiting. Furthermore, where the description of one or more embodiments uses the term "comprising," those skilled in the art would understand that in some specific instances, the embodiment or embodiments can be alternatively described using language "consisting essentially of" and/or "consisting of." It should also be understood that in some embodiments the order of steps or order for performing certain actions is immaterial so long as the present teachings remain operable. Moreover, in some embodiments two or more steps or actions can be conducted simultaneously.

a.) As used herein, "analyte" refers to any molecule of interest that may be determined. Non-limiting examples of analytes include, but are not limited to, proteins, peptides, nucleic acids (e.g. DNA or RNA), amino acids, carbohydrates, lipids, steroids, vitamins (e.g. vitamin $D_2$ (sometimes referred to as ergocalciferol), vitamin $D_3$ (sometimes referred to a cholecalciferol), vitamin $B_2$, vitamin $B_6$, vitamin A, vitamin $A_2$, vitamin E, vitamin K, and metabolites thereof), prostaglandins, and other small molecules with a molecular weight of less than 1500 daltons (Da). The source of the analyte, or the sample comprising the analyte, is not a limitation as it can come from any source. The analyte or analytes can be natural or synthetic. Non-limiting examples of sources for the analyte, or the sample comprising the analyte, include cells or tissues, or cultures (or subcultures) thereof. Non-limiting examples of analyte sources include, but are not limited to, crude or processed cell lysates, body fluids, tissue extracts, cell extracts or fractions (or portions) from a separations process such as a chromatographic separation, a 1D electrophoretic separation, a 2D electrophoretic separation or a capillary electrophoretic separation. Body fluids include, but are not limited to, blood, urine, feces, spinal fluid, cerebral fluid, amniotic fluid, lymph fluid or a fluid from a glandular secretion. By processed cell lysate we mean that the cell lysate is treated, in addition to the treatments needed to lyse the cell, to thereby perform additional processing of the collected material. For example, the sample can be a cell lysate comprising one or more analytes that are peptides formed by treatment of the cell lysate with one or more proteolytic enzymes to thereby digest precursor peptides and/or proteins.

b.) Except as when clearly not intended based upon the context in which it is being used (e.g. when made in reference to a specific structure that dictates otherwise), "ester" refers to both an ester and/or a thioester.

c.) As used herein, "cleavable linker" refers to a moiety covalently attached to a solid support that cleavably links a labeling reagent or labeled analyte to a support and wherein at least one bond in the cleavable linker can be cleaved by treatment with light, heat or chemical reagent(s) (for the avoidance of doubt, "chemical reagent(s)" is intended to include an enzyme or enzymes) to thereby release the label or labeled analyte, or a fragment thereof, from the support.

d.) As used herein, "fragmentation" refers to the breaking of a covalent bond.

e.) As used herein, "fragment" refers to a product of fragmentation (noun) or the operation of causing fragmentation (verb).

f.) As used herein, "hydrate form" refers to any hydration state of a compound or a mixture of more than one hydration states of a compound. For example, a labeling reagent discussed herein can be a hemihydrate, a monohydrate, a dihydrate, etc. Moreover, a sample of a labeling reagent described herein can, for example, simultaneously comprise monohydrate, dihydrate and hemihydrate forms.

g.) As used herein, a halogen group or halide refers to —F (fluorine), —Cl (chlorine), —Br (bromine), or —I (iodine).

h.) As used herein with respect to a compound, "isotopically enriched" refers to a compound (e.g. labeling reagent) that has been enriched with one or more heavy atom isotopes (e.g. stable isotopes such as deuterium (i.e. $^2$H), $^{13}$C, $^{15}$N, $^{18}$O, $^{34}$S, $^{37}$Cl or $^{81}$Br). The isotopically enriched compound can be synthetically enriched. In some embodiments, unstable isotopes can also be used (e.g. $^{14}$C or $^3$H). By "enriched" we mean that the amount of heavy atom isotope exceeds natural isotopic abundance. In various embodiments, the isotopically enriched compound can comprise 1, 2, 3, 4, 5, 6, 7, 8, 9, 10, 11, 12, 13, 14, 15, 16, 17, 18, 19, 20, 21, 22, 23, 24, 25, 26, 27, 28, 29, 30 or more isotopically enriched sites.

Because isotopic enrichment is not 100% effective, there can be impurities in a sample of the compound that are of lesser states of enrichment and these will have a lower mass. Likewise, because of over-enrichment (e.g. undesired enrichment) and because of natural isotopic abundance, there can be impurities in a sample of the compound that are of greater mass. In some embodiments, each incorporated heavy atom isotope can be present at an isotopically enriched site in at least 80 percent isotopic purity. In some embodiments, each incorporated heavy atom isotope can be present at an isotopically enriched sited in at least 93 percent isotopic purity. In some embodiments, each incorporated heavy atom isotope can be present at an isotopically enriched site in at least 96 percent isotopic purity. In some embodiments, each incorporated heavy atom isotope can be present at an isotopically enriched site in at least 98 percent purity.

i.) As used herein, "isotopically enriched site" refers to the position in a compound where a heavy atom isotope is substituted for a light version of the atom (e.g. substitution of $^{13}$C for $^{12}$C, $^{18}$O for $^{16}$O, $^{15}$N for $^{14}$N or deuterium for hydrogen).

j.) As used herein with respect to a compound, "light" refers to the compound as not being enriched with a heavy atom isotope. As used herein with respect to an atom, "light" refers to the lowest mass isotope of the atom. As used herein with respect to a compound, "heavy" refers to the compound as being enriched with at least one heavy atom isotope. As used herein with respect to an atom, "heavy" refers to a heavy mass isotope of the atom.

k). As used herein, "labeling reagent" refers to a moiety suitable to mark an analyte for determination. The term label is synonymous with the terms tag and mark and other equivalent terms and phrases. For example, a labeled analyte can also be referred to as a tagged analyte or a marked analyte. Accordingly the terms "label", "tag", "mass tag", "mark" and derivatives of these terms, are equivalent and interchangeable and refer to a moiety suitable to mark, or that has marked, an analyte for determination. Sometimes a labeling reagent can be referred to a tagging reagent or a mass tagging reagent.

l.) As used herein, "natural isotopic abundance" refers to the level (or distribution) of one or more heavy isotopes found in a compound based upon the natural prevalence of an isotope or isotopes in nature. For example, a natural compound obtained from living plant matter may contain about 1.08% $^{13}$C relative to $^{12}$C.

m.) As used herein, isobars are structurally indistinguishable compounds (except for isotopic content and/or distribution of heavy atom isotopes) of the same nominal gross mass. For the avoidance of any doubt, compounds 1-4 of FIG. 4$a$ are isobaric by the definition set forth herein. By comparison, as used herein isomers are structurally distinguishable compounds of the same nominal gross mass. Exemplary isomeric isobars are illustrated in FIG. 4$b$.

n.) As used herein, "support", "solid support", "solid carrier" or "resin" refers to any solid phase material. Solid support encompasses terms such as "support", "synthesis support", "solid phase", "surface" "membrane" and/or "support". A solid support can be composed of organic polymers such as polystyrene, polyethylene, polypropylene, polyfluoroethylene, polyethyleneoxy, and polyacrylamide, as well as co-polymers and grafts thereof. A solid support can also be inorganic, such as glass, silica, controlled-pore-glass (CPG), or reverse-phase silica. The configuration of a solid support can be in the form of beads, spheres, particles, granules, a gel, a membrane or a surface. Surfaces can be planar, substantially planar, or non-planar. Solid supports can be porous or non-porous, and can have swelling or non-swelling characteristics. A solid support can be configured in the form of a well, depression or other container, vessel, feature or location. A plurality of solid supports can be configured in an array at various locations, addressable for robotic delivery of reagents, or by detection methods and/or instruments.

o.) As used herein, "support-bound" refers to a compound that is covalently immobilized to a solid support.

p.) As used herein, "sample, or a fraction thereof" or "sample fraction" can be used to refer to a fraction of a sample. The fraction of the sample can be generated either by simply withdrawing a fraction of a sample else it can be generated by performing a separations process that results in the sample being fractionated into two or more fractions. Unless the content of the description indicates otherwise, these phrases are equivalent and interchangeable and refer to either type of creation of a fraction (or portion) of a sample.

q.) As used herein, "signature ion" and "reporter ion" are interchangeable and both refer to the signature ion of unique mass produced from the reporter moiety by fragmentation of a labeling reagent or labeled analyte in a mass spectrometer. The signature ion or reporter ion can be used to identify the unique labeling reagent used to label an analyte and its peak intensity in MS/MS analysis can be correlated with the amount of labeled analyte present in the sample (or fraction thereof) that is analyzed. As used herein, the signature ion or reporter ion is sometimes merely referred to as a reporter. As used herein, the reporter moiety is also sometimes merely referred to a reporter. It is to be understood that the reporter moiety refers to the group attached to a labeling reagent, labeled analyte or fragment thereof and the reporter ion refers to the fragment ion generated upon fragmentation of the bond that links the reporter moiety to the labeling reagent, labeled analyte or a fragment thereof. Accordingly, the context in which the word "reporter" is used will indicate its intended meaning. It also is to be understood that the phrase "unique reporter moiety" is equivalent to, and interchangeable with, "reporter moiety of unique mass" and that "unique reporter ion" or "unique signature ion" is equivalent to, and interchangeable with, "reporter ion of unique mass" or "signature ion of unique mass".

r.) As used herein, the term "salt form" refers to a salt of a compound or a mixture of salts of a compound. In addition, zwitterionic forms of a compound are also included in the term "salt form." Salts of compounds having an amine, or other basic, group can be obtained, for example, by reaction with a suitable organic or inorganic acid, such as hydrogen chloride, hydrogen bromide, acetic acid, perchloric acid and the like (including any combinations thereof). Compounds with a quaternary ammonium group may also contain a counteranion such as chloride, bromide, iodide, acetate, perchlorate and the like (including any combinations thereof). Salts of compounds having a carboxylic acid, or other acidic functional group, can be prepared by reacting the compound with a suitable base, for example, a hydroxide base. Accordingly, salts of acidic functional groups may have a countercation, such as sodium, potassium, magnesium, calcium, etc. (including any combinations thereof).

s.) As used herein, the term "steroid" is intended to include, but not be limited to, cortisol, 11-desoxycortisol (compound S), corticosterone, testosterone, epitestosterone, desoxymethyltestosterone, tetrahydrogestrinone (THG), estradiol, estrone, 4-hydroxyestrone, 2-methoxyestrone, 2-hydroxyestrone, 16-ketoestradiol, 16 alpha-hydroxyestrone, 2-hydroxyestrone-3-methylether, prednisone, prednisolone, pregnenolone, progesterone, dehydroepiandrosterone (DHEA), 17 OH pregnenolone, 17 OH progesterone, 17 OH progesterone, androsterone, epiandrosterone, delta 4 androstenedione (D4A), stigmasterol, and cholesterol.

t.) As used herein, "synthetic compound" refers to a compound that is created by manipulation of processes including the manipulation of naturally occurring pathways. Thus, a synthetic compound can be produced using synthetic chemistry techniques. However, as used herein, "synthetic compound" is also intended to include compounds that are produced, for example, by enzymatic methods, including for example, feeding isotopically enriched compounds to organisms, such as bacteria or yeast, that alter them to thereby produce the isotopically enriched labeling reagents, or intermediates of the labeling reagents, described herein.

u.) As used herein, "synthetically enriched" or "enriched synthetically" refers to the manipulation of a synthetic or natural process to thereby produce a synthetic compound such as the isotopically enriched labeling reagents, or intermediates to the labeling reagents, described herein.

v.) It is well accepted that the mass of an atom or molecule can be approximated, often to the nearest whole number atomic mass unit or the nearest tenth or hundredth of an atomic mass unit. As used herein, "gross mass" refers to the absolute mass as well as to the approximate mass within a range where the use of isotopes of different atom types are so close in mass that they are the functional equivalent for the purpose of balancing the mass of the reporter and/or linker moieties (so that the gross mass of the reporter/linker combination is the same within a set or kit of isomeric and/or isobaric labeling reagents) whether or not the very small difference in mass of the different isotopes types used can be detected.

For example, the common isotopes of sulfur have a gross mass of 32 (actual mass 31.9720) and 34 (actual mass 33.9678), the common isotopes of oxygen have a gross mass of 16.0 (actual mass 15.9949) and 18.0 (actual mass 17.9992), the common isotopes of carbon have a gross mass of 12.0 (actual mass 12.00000) and 13.0 (actual mass 13.00336) and the common isotopes of nitrogen have a gross mass of 14.0 (actual mass 14.0031) and 15.0 (actual mass 15.0001). Whilst these values are approximate, one of skill in the art will appreciate that if one uses the $^{18}O$ isotope (or the $^{34}S$ isotope) at an isotopically enriched site within one label of a set, the additional 2 mass units (over the isotope of oxygen having a gross mass of 16.0) can, for example, be compensated for in a different label of the set comprising $^{18}O$ (or the $^{32}S$ isotope) by incorporating, elsewhere in the label, two carbon $^{13}C$ atoms, instead of two $^{12}C$ atoms, two $^{15}N$ atoms, instead of two $^{14}N$ atoms or even one $^{13}C$ atom and one $^{15}N$ atom, instead of a $^{12}C$ and a $^{14}N$, to compensate for the $^{18}O$ (or the $^{34}S$ isotope). In this way the two different labels of the set can have the same gross mass since the very small actual differences in mass between the use of two $^{13}C$ atoms (instead of two $^{12}C$ atoms), two $^{15}N$ atoms (instead of two $^{14}N$ atoms), one $^{13}C$ and one $^{15}N$ (instead of a $^{12}C$ and $^{14}N$) or one $^{18}O$ atom (instead of one $^{18}O$ atom—or one $^{34}S$ instead of one $^{32}S$), to thereby achieve an increase in mass of two Daltons in all of the labels of the set or kit, is not an impediment to the nature of the analysis.

This can be illustrated with reference to FIG. 4a. In FIG. 4a, the reporter/linker combination of compound 3 (FIG. 4a; molecular formula: $C_5{}^{13}CH_{11}{}^{15}N_2O$) has two $^{15}N$ atoms and one $^{13}C$ atom and a total theoretical mass of 130.085. By comparison, the reporter/linker moiety of isobar 1 (FIG. 4a; molecular formula $C_5{}^{13}CH_{11}N_2{}^{18}O$) has one $^{18}O$ atom and one $^{13}C$ atom and a total theoretical mass of 130.095. Compounds 1 and 3 can be isobars that are structurally indistinguishable, except for heavy atom isotope content, although there can be a slight absolute mass difference of the reporter/linker moiety (mass 130.095 vs. mass 130.085 respectively). However, the gross mass of the reporter/linker moiety of compounds 1 and 3 is 130.1 for the purposes of this invention since this is not an impediment to the analysis whether or not the mass spectrometer is sensitive enough to measure the small difference between the absolute mass of the reporter ions generated from isobars 1 and 3.

Similarly with reference to FIG. 4b, two isomeric reagents are illustrated wherein the mass of the reporter/linker moiety of compounds 5 and 6 is 144.111 and 144.100, respectively. The gross mass of the reporter/linker moiety of these compounds is 144.1 for the purposes of this invention since it is not an impediment to the analysis whether or not the mass spectrometer is sensitive enough to measure the small difference between the absolute mass of the reporter ions generated from compounds 5 and 6.

From FIGS. 4a and 4b, it is clear that the distribution of the same heavy atom isotopes within a structure is not the only consideration for the creation of sets of isomeric and/or isobaric labeling reagents. It is possible to mix heavy atom isotope types to achieve isomers and/or isobars of a desired gross mass. In this way, both the selection (combination) of heavy atom isotopes as well as their distribution is available for consideration in the production of the isomeric and/or isobaric labeling reagents useful for embodiments of this invention.

w.) As used herein, the term "alkyl" refers to a straight chained or branched $C_2$-$C_8$ hydrocarbon or a cyclic $C_3$-$C_8$ hydrocarbon (i.e. a cycloalkyl group such as a cyclopropyl group, a cyclobutyl group, a cyclopentyl group, a cyclohexyl group or a cyclohexylmethylene group) that can be completely saturated. When used herein, the term "alkyl" refers to a group that may be substituted or unsubstituted. In some embodiments, the term "alkyl" is also intended to refer to those compounds wherein one or more methylene groups in the alkyl chain can be replaced by a heteroatom such as —O—, —Si— or —S—. In some embodiments, alkyl groups can be straight chained or branched $C_2$-$C_6$ hydrocarbons or cyclic $C_3$-$C_6$ hydrocarbons that can be completely saturated.

x.) As used herein, the term "alkylene" refers to a straight or branched alkyl chain or a cyclic alkyl group that comprises at least two points of attachment to at least two moieties (e.g., —{$CH_2$}— (methylene), —{$CH_2CH_2$}—, (ethylene),

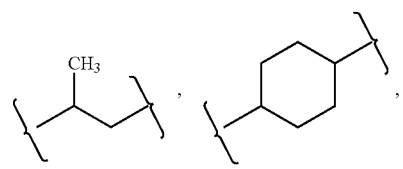

etc., wherein the brackets indicate the points of attachment. When used herein the term "alkylene" refers to a group that may be substituted or unsubstituted. In some embodiments, the term "alkylene" is also intended to refer to those compounds wherein one or more methylene groups, if any, in an alkyl chain of the alkylene group can be replaced by a heteroatom such as —O—, —Si— or —S—. In some embodiments, an alkylene group can be a $C_1$-$C_{10}$ hydrocarbon. In some embodiments, an alkylene group can be a $C_2$-$C_6$ hydrocarbon.

y.) As used herein, the term "alkenyl" refers to a straight chained or branched $C_2$-$C_8$ hydrocarbon or a cyclic $C_3$-$C_8$ hydrocarbon that comprises one or more double bonds. When used herein, the term "alkenyl" refers to a group that can be substituted or unsubstituted. In some embodiments, the term "alkenyl" is also intended to refer to those compounds wherein one or more methylene groups, if any, in an alkyl chain of the alkenyl group can be replaced by a heteroatom such as —O—, —Si— or —S—. In some embodiments, alkenyl groups can be straight chained or branched $C_2$-$C_6$ hydrocarbons or cyclic $C_3$-$C_6$ hydrocarbons that comprise one or more double bonds.

z.) As used herein, the term "alkenylene" refers to an alkenyl group that comprises two points of attachment to at least two moieties. When used herein the term "alkenylene" refers to a group that may be substituted or unsubstituted. In some embodiments, the term "alkenylene" is also intended to refer to those compounds wherein one or more methylene groups, if any, in an alkyl chain of the alkenylene group can be replaced by a heteroatom such as —O—, —Si— or —S—.

aa.) As used herein, the term "alkynyl" refers to a straight chained or branched $C_2$-$C_8$ hydrocarbon or a cyclic $C_3$-$C_8$ hydrocarbon that comprises one or more triple bonds.

When used herein, the term "alkynyl" refers to a group that may be substituted or unsubstituted. In some embodiments, the term "alkynyl" is also intended to refer to those compounds wherein one or more methylene groups, if any, in an alkyl chain of the alkynyl group can be replaced by a heteroatom such as —O—, —Si— or —S—. In some embodiments, alkynyl groups can be straight chained or branched $C_2$-$C_6$ hydrocarbons or cyclic $C_3$-$C_6$ hydrocarbons that have one or more triple bonds.

ab.) As used herein, the term "alkynylene" refers to an alkynyl group that comprises two points of attachment to at least two moieties. When used herein the term "alkynylene" refers to a group that may be substituted or unsubstituted. In some embodiments, the term "alkynylene" is also intended to refer to those compounds wherein one or more methylene groups, if any, in an alkyl chain of the alkynylene group can be replaced by a heteroatom such as —O—, —Si— or —S—.

ac.) As used herein, the term "aliphatic" refers to any of the straight, branched, or cyclic alkyl, alkenyl, and alkynyl moieties as defined above. When used herein the term "aliphatic" refers to a group that may be substituted or unsubstituted.

ad.) As used herein, the term "aryl", either alone or as part of another moiety (e.g., arylalkyl, etc.), refers to carbocyclic aromatic groups such as phenyl. Aryl groups also include fused polycyclic aromatic ring systems in which a carbocyclic aromatic ring is fused to another carbocyclic aromatic ring (e.g., 1-naphthyl, 2-naphthyl, 1-anthracyl, 2-anthracyl, etc.) or in which a carbocylic aromatic ring is fused to one or more carbocyclic non-aromatic rings (e.g., tetrahydronaphthylene, indan, etc.). As used herein, the term "aryl" refers to a group that may be substituted or unsubstituted.

ae.) As used herein, the term "heteroaryl," refers to an aromatic heterocycle that comprises 1, 2, 3 or 4 heteroatoms selected, independently of the others, from nitrogen, sulfur and oxygen. As used herein, the term "heteroaryl" refers to a group that may be substituted or unsubstituted. A heteroaryl may be fused to one or two rings, such as a cycloalkyl, an aryl, or a heteroaryl ring. The point of attachment of a heteroaryl to a molecule may be on the heteroaryl, cycloalkyl, heterocycloalkyl or aryl ring, and the heteroaryl group may be attached through carbon or a heteroatom. Examples of heteroaryl groups include imidazolyl, furyl, pyrrolyl, thienyl, thiazolyl, isoxazolyl, isothiazolyl, thiadiazolyl, oxadiazolyl, pyridinyl, pyrimidyl, pyrazinyl, pyridazinyl, quinolyl, isoquinolinyl, indazolyl, benzoxazolyl, benzisooxazolyl, benzofuryl, benzothiazolyl, indolizinyl, imidazopyridinyl, pyrazolyl, triazolyl, oxazolyl, tetrazolyl, benzimidazolyl, benzoisothiazolyl, benzothiadiazolyl, benzoxadiazolyl, indolyl, tetrahydroindolyl, azaindolyl, imidazopyridyl, quinazolinyl, purinyl, pyrrolo[2,3]pyrimidyl, pyrazolo[3,4]pyrimidyl or benzo(b)thienyl, each of which can be optionally substituted.

af.) As used herein, the term "arylene" refers to an aryl or heteroaryl group that comprises at least two points of attachment to at least two moieties (e.g., phenylene, etc.). The point of attachment of an arylene fused to a carbocyclic, non-aromatic ring may be on either the aromatic, non-aromatic ring. As used herein, the term "arylene" refers to a group that may be substituted or unsubstituted.

ag.) As used herein, the term "arylalkyl" refers to an aryl or heteroaryl group that is attached to another moiety via an alkylene linker. As used herein, the term "arylalkyl" refers to a group that may be substituted or unsubstituted. In some embodiments, the term "arylalkyl" is also intended to refer to those compounds wherein one or more methylene groups, if any, in the alkyl chain of the arylalkyl group can be replaced by a heteroatom such as —O—, —Si— or —S—.

ah.) As used herein, the term "arylalkylene" refers to an arylalkyl group that has at least two points of attachment to at least two moieties. The second point of attachment can be on either the aromatic ring or the alkylene group. As used herein, the term "arylalkylene" refers to a group that may be substituted or unsubstituted. In some embodiments, the term "arylalkylene" is also intended to refer to those compounds wherein one or more methylene groups, if any, in the alkyl chain of the arylalkylene group can be replaced by a heteroatom such as —O—, —Si— or —S—. When an arylalkylene is substituted, the substituents may be on either or both of the aromatic ring or the alkylene portion of the arylalkylene.

ai.) As used herein, the terms "optionally substituted" and "substituted or unsubstituted" are equivalent and interchangeable. Suitable substituents for any an alkyl, an alkylene, an alkenyl, an alkenylene, an alkynyl, an alkynylene, an aryl, an aryl alkyl, an arylene, a heteroaryl or an arylalkylene group includes any substituent that is stable under the reaction conditions used in embodiments of this invention. Non limiting examples of suitable substituents can include: an alkyl (e.g., methyl, ethyl, n-propyl, isopropyl, n-butyl, isobutyl, sec butyl, t-butyl, cyclohexyl, etc.) group, a haloalkyl (e.g., trifluoromethyl, 2,2,2-trifluoroethyl-, etc.) group, an alkoxy (e.g., methoxy, ethoxy, etc.) group, an aryl (e.g., phenyl) group, an arylalkyl (e.g., benzyl) group, a nitro group (—$NO_2$), a cyano group (—CN), a quaternized nitrogen atom or a halogen group (e.g., fluorine, chlorine, bromine and/or iodine) group.

In addition, a portion of an alkyl, an alkylene, an alkenyl, an alkenylene, an alkynyl, an alkynylene, an aryl, an aryl alkyl, an arylene, a heteroaryl or an arylalkylene group may optionally be substituted with =O or =S.

aj.) As used herein, the term "active ester" refers to compounds that can react readily under basic conditions with amines, alcohols and certain thiols to provide amides, esters and thioesters, respectively. Additional reference is made to: Leo A Paquette, *Encyclopedia of Reagents for Organic Synthesis*, Vol. 2, John Wiley and Sons, New York, 1995 as evidence that active ester is a term well-established in field of organic chemistry.

ak.) As used herein, the term "heterocyclic ring" refers to any cyclic molecular structure comprising atoms of at least two different elements in the ring or rings. Additional reference is made to: *Oxford Dictionary of Biochemistry and Molecular Biology*, Oxford University Press, Oxford, 1997 as evidence that heterocyclic ring is a term well-established in field of organic chemistry.

al.) As used herein, the term "leaving group" refers to any atom or group, charged or uncharged, that departs during a substitution or displacement reaction from what is regarded as the residual or main part of the substrate of the reaction. Additional reference is made to: *Oxford Dictionary of Biochemistry and Molecular Biology*, Oxford University Press, Oxford, 1997 as evidence that leaving group is a term well-established in field of organic chemistry.

am.) As used herein, the term "protecting group" refers to a chemical group that is reacted with, and bound to, a functional group in a molecule to prevent the functional group from participating in subsequent reactions of the molecule but which group can subsequently be removed to thereby regenerate the unprotected functional group. Additional reference is made to: *Oxford Dictionary of Biochemistry and Molecular Biology*, Oxford University Press, Oxford, 1997 as evidence that protecting group is a term well-established in field of organic chemistry.

DESCRIPTION OF VARIOUS EMBODIMENTS

It is to be understood that the discussion set forth below in this "General" section can pertain to some, or to all, of the various embodiments of the invention described herein.

I. General

The Labeling Reagent:

As discussed previously, a labeling reagent that can be used for the analysis of an analyte or analytes using mass spectrometry can comprise a reporter moiety, a balance moiety (or linker moiety) and a reactive group. Novel labeling reagents disclosed herein also comprise at least one non-encoded detectable label such as a chromophore, a fluorophore, a spin label, an enzyme or a chemiluminescent compound and, in some embodiments, can be represented by the general formula I;

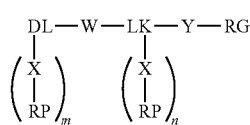

including a salt form and/or a hydrate form thereof. RG is a reactive group as described in more detail below. RP is a reporter moiety as described in more detail below. DL is a non-encoded detectable label as discussed in more detail below. LK is a linker moiety as described in more detail below. X is a covalent bond as described in more detail below. Y and W are each independently a covalent bond or a linking group as described in more detail below and m and n are each 0 or 1 provided that m+n=1.

In some embodiments, the labeling reagent can be support-bound. Thus, in some embodiments, the labeling reagent can be represented by the general formula $I^{ss}$:

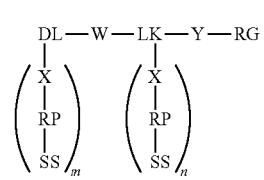

including a salt form and/or a hydrate form thereof. RG is a reactive group as described in more detail below. RP is a reporter moiety as described in more detail below. DL is a non-encoded detectable label as discussed in more detail below. LK is a linker moiety as described in more detail below. SS is a solid support to which the reporter moiety "RP" of the labeling reagent is covalently linked through a cleavable linker as described in more detail below. X is a covalent bond as described in more detail below. Y and W are each independently a covalent bond or a linking group as described in more detail below and m and n are each 0 or 1 provided that m+n=1.

The Reactive Group:

The reactive group (sometimes represented by use of the shorthand "RG") of the labeling reagent or reagents used in various embodiments can comprise any electrophilic or a nucleophilic group that is capable of reacting with one or more functional groups of one or more reactive analytes of a sample. The reactive group reacts with a functional group of the analyte to thereby covalently link the analyte to the labeling reagent. Thus, each labeling reagent is capable of reacting with the one or more reactive analytes of a sample to thereby form the one or more labeled analytes from the sample.

It is to be understood that in some embodiments, the reactive group may be considered to include an atom or group associated with the linker moiety (i.e. balance moiety). For example, if the reactive group is an active ester or carboxylic acid halide group, the carbonyl group of the active ester or carboxylic acid halide may, in some embodiments, also be considered to be associated with the linker moiety for purposes of balancing the mass of the reporter moiety within a set of isomeric and/or isobaric labeling reagents where the carbonyl carbon is present in both the labeling reagent and in the labeled analyte. This will typically be apparent where heavy atom isotopes are included in the carbonyl group of some or all of the labeling reagents of a set of isomeric and/or isobaric labeling reagents. Consequently, in some embodiments, the reactive group can be understood to merely represent the leaving group of a reactive group while in other embodiments the reactive group can comprise additional atoms or moieties that are associated with the linker moiety. Thus, it is also to be understood that when the reactive group is represented by some of the specific moieties discussed below, the analyte (may be linked to the linker moiety (i.e. balance moiety) through one or more additional atoms or groups that may, or may not, be considered to be part of the linker moiety.

The reactive group can be preexisting or it can be prepared in-situ. In-situ preparation of the reactive group can proceed in the absence of the reactive analyte or it can proceed in the presence of the reactive analyte. For example, a carboxylic acid group can be modified in-situ with water-soluble carbodiimide (e.g. 1-(3-dimethylaminopropyl)-3-ethylcarbodiimide hydrochloride; EDC) to thereby prepare an electrophilic group that can be reacted with a nucleophile such as an alkyl or aryl amine group of the analyte. In some embodiments, activation of the carboxylic acid group of a labeling reagent with EDC can be performed in the presence of an amine (or other nucleophile) containing analyte. In some embodiments, the amine (or other nucleophile) containing analyte can also be added after the initial reaction with EDC is performed. In other embodiments, the reactive group can be generated in-situ by the in-situ removal of a protecting group. Consequently, any existing or newly created reagent or reagents that can effect the derivatization of analytes by the reaction of nucleophiles and/or electrophiles are contemplated by the method, mixture, kit and/or composition embodiments of this invention.

Where the reactive group of the labeling reagent comprises an electrophile, it can react with a suitable nucleophilic group of the analyte or analytes. Where the reactive group of the labeling reagent comprises a nucleophile, it can react with a suitable electrophilic group of the analyte or analytes. Numerous pairs of suitable nucleophilic groups and electrophilic groups are known and often used in the chemical and biochemical arts. Non-limiting examples of reagents comprising suitable nucleophilic or electrophilic groups that can be coupled to analytes (e.g. such as proteins, peptides, nucleic acids, carbohydrates, lipids, steroids, vitamins, prostaglandins or other small molecules having a mass of less that 1500 daltons) to effect their derivatization, are described in the Pierce Life Science & Analytical Research Products Catalog & Handbook (a Perstorp Biotec Company), Rockford, Ill. 61105, USA. Other suitable reagents are well known in the art and are commercially available from numerous other vendors such as Sigma-Aldrich.

The reactive group of a labeling reagent can comprise an amine reactive group. For example, the amine reactive group can be an active ester. Active esters are well known in peptide synthesis and refer to certain esters that can be easily reacted with the N-α amine of an amino acid under conditions commonly used in peptide synthesis. (See: Leo A Paquette, *Encyclopedia of Reagents for Organic Synthesis*, Vol. 2, John Wiley and Sons, New York, 1995) The amine reactive active ester group can be an N-hydroxysuccinimidyl ester (NHS), a N-hydroxysulfosuccinimidyl ester (NHSS), a pentafluorophenyl ester (Pfp), a 2-nitrophenyl ester (2-NP), a 3-nitrophenyl ester (3-NP) a 4-nitrophenyl ester (4-NP), a 2,4-dinitrophenylester (2,4-NP), a pentafluorophenyl ester (Pfp), a pentachlorophenyl ester (Pcp), 3-hydroxy-1,2,3-benzotriazine-4(3H)-one ester (Dhbt), hydroxypyrrolidinone ester (NHP), a 2,4-dihalophenyl ester, a 2,2,2-trifluoroethanyl ester or a 1,1,1,3,3,3-hexafluoro-2-propanyl ester. For example, the leaving group of an active ester (referred to herein generally as Z' in some embodiments such that in the situation where the variable RG is synonymous with only the leaving group portion of the reactive group) can be represented by the following formulas:

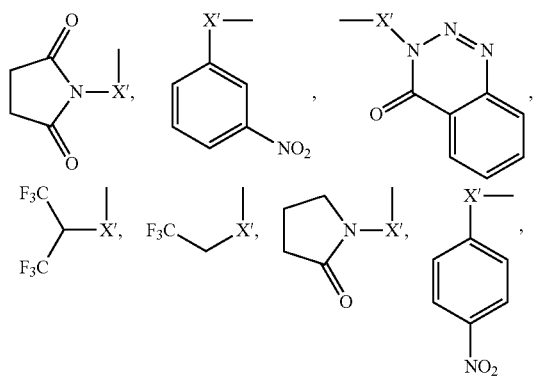

Figure 7:
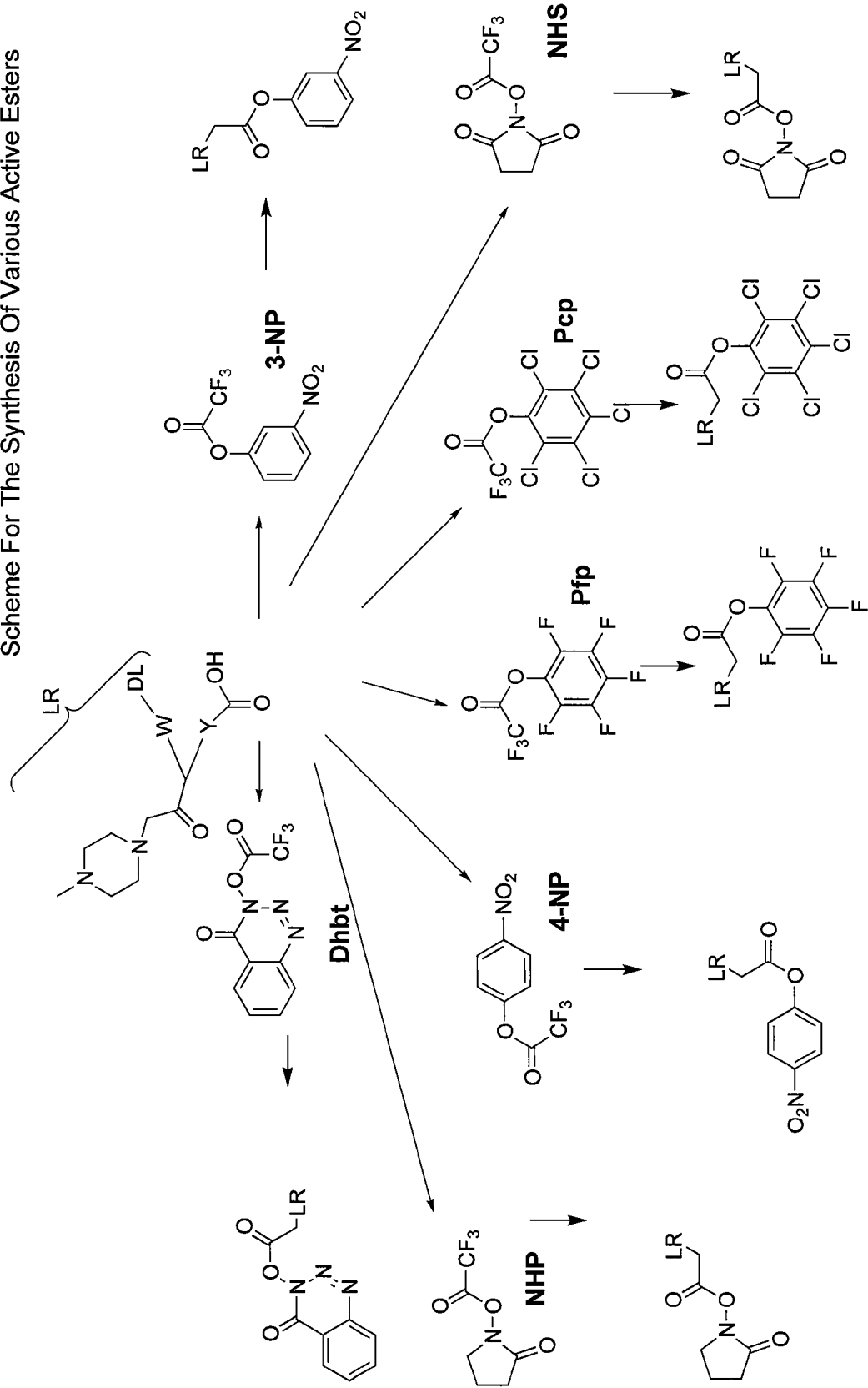
FIG. 7 is an illustration of a scheme for the synthesis of various active esters.

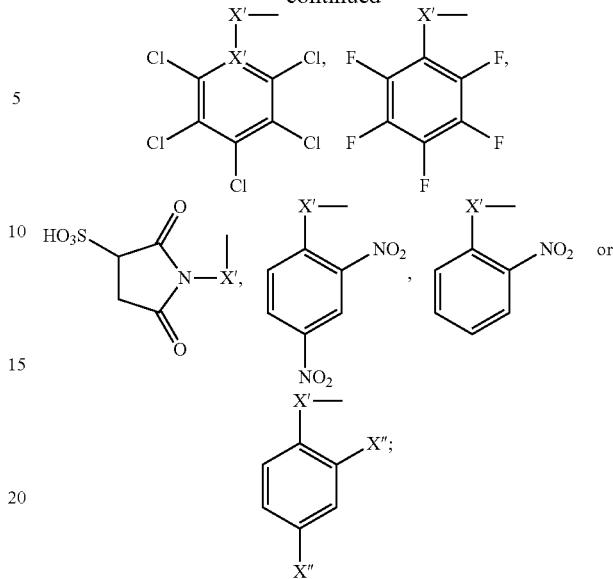

wherein X' is —O— or —S— and each X" is, independently of the other, —F, —Cl, —Br or —I (See: United States Published Patent Application No. US 2005-0148771 A1 for a more detailed description of the synthesis of active esters of N-methyl piperazine compounds and FIG. 7 for an illustration of various synthetic routes to said active esters). All of the foregoing being alcohol or thiol leaving groups of an active ester wherein said alcohol or thiol leaving group can be displaced by the reaction of the N-α-amine of the amino acid with the carbonyl carbon of the active ester group. Accordingly, it should be apparent to the ordinary practitioner that the active ester (e.g. N-hydroxysuccinimidyl ester) of any suitable labelling/tagging reagent described herein could be prepared using well-known procedures in combination with the disclosure provided herein (Also see for example: Greg T. Hermanson (1996). "*The Chemistry of Reactive Groups*" in "*Bioconjugate Techniques*", Chapter 2, pages 137-165, Academic Press, (New York); and also see: "*Innovation And Perspectives In Solid Phase Synthesis*", Editor: Roger Epton, SPCC (UK) Ltd, Birmingham, 1990).

In some embodiments, the reactive group of the labelling reagent can comprise a mixed anhydride since mixed anhydrides are known to efficiently react with amine groups to thereby produce amide bonds. Mixed anhydrides are well known and can be prepared using well-known methods often applied in the fields of organic and/or peptide chemistry.

In some embodiments, the reactive group of the labelling reagent can be a carboxylic acid halide group, such as an acid fluoride group (See: Carpino et al., *J. Am. Chem. Soc.,* 112: 9651 (1990)) or acid chloride group. Reaction of the acid halide group with an amine of the analyte will form an amide. Reaction of the acid halide group with a hydroxyl or thiol group of the analyte will produce an ester or thio ester, respectively.

In some embodiments, the reactive group can be a sulfonic acid group of a sulfonyl halide. If a sulfonic acid, it can be activated for reaction with the analyte. If a sulfonyl halide, it can be reacted directly with the analyte as this is an activated form.

In some embodiments, the reactive group can be an isocyanate or isothiocyanate group.

In some embodiments, the reactive group of a labeling reagent can comprise a thiol reactive group. For example, the thiol reactive group can be a malemide group, an alkyl halide group, an α-halo-acyl group, an α-halo thione group or an α-halo imine group. By 'halide group' or 'halo' or 'halo group' we mean atoms of fluorine, chlorine, bromine or iodine. Said thiol reactive groups are well known and can be prepared using methods often applied in the field of peptide chemistry.

In some embodiments, the reactive group of a labeling reagent can comprise a hydroxyl reactive group. For example, the hydroxyl reactive group can be a trityl-halide or a silyl-halide reactive moiety. The trityl-halide reactive moieties can be substituted (e.g. X'''-methoxytrityl, X'''-dimethoxytrityl, X'''-trimethoxytrityl, etc) or unsubstituted wherein X''' is the bond that links the reactive group to the linker (i.e. balance). The silyl reactive moieties can be alkyl substituted silyl halides, such as X'''-dimethylsilyl, X'''-ditriethylsilyl, X'''-dipropylsilyl, X'''-diisopropylsilyl, etc.) wherein X''' is the bond that links the reactive group to the linker (i.e. balance). Said reactive groups are well known and can be prepared using methods often applied in the field of nucleic acid chemistry.

In some embodiments, the reactive group of the labeling reagent comprise a nucleophile such as an amine group, a hydroxyl group, a thiol group or a hydrazide group. In some embodiments, the nucleophilic reactive group can be an aminoalkyl group, a hydroxyalkyl group or a thioalkyl group. Said reactive groups are well known and can be prepared using methods often applied in the field of organic chemistry.

The Reporter Moiety:

The reporter moiety (sometimes represented by use of the shorthand "RP") of the labeling reagent or reagents used in embodiments of this invention is a group that has a unique mass (or mass to charge ratio in a mass spectrometer) that can be determined. Accordingly, in some embodiments, each reporter moiety of a set of isomeric and/or isobaric labeling reagents has a unique gross mass, and its corresponding signature ion, is different for each labeling reagent of the set.

Different reporter moieties can comprise one or more heavy atom isotopes to achieve their unique gross mass. For example, isotopes of carbon ($^{12}C$, $^{13}C$ and $^{14}C$), nitrogen ($^{14}N$ and $^{15}N$), oxygen ($^{16}O$ and $^{18}O$), sulfur ($^{32}S$ and $^{34}S$) or hydrogen (hydrogen, deuterium and tritium) exist and can be used in the preparation of a diverse group of reporter moieties. These are not limiting as other light and heavy atom isotopes can also be used in the reporter moieties. Basic starting materials suitable for preparing reporter moieties comprising light and heavy atom isotopes are available from various commercial sources such as Cambridge Isotope Laboratories, Andover, Mass. (See: list of "basic starting materials" at www.isotope.com) and Isotec (a division of Sigma-Aldrich). Cambridge Isotope Laboratories and Isotec will also prepare desired compounds under custom synthesis contracts. Id.

The reporter moiety can either comprise a fixed charge or can become ionized during the analysis process. Because the reporter moiety can either comprises a fixed charge or can become ionized, the labeling reagent might be isolated or be used to label the reactive analyte in a salt (or a mixture of salts) or zwitterionic form. Ionization of the reporter moiety (or reporter ion) facilitates its determination in a mass spectrometer. Accordingly, the presence of the reporter moiety in a labeled analyte can be determined as a fragment ion, sometimes referred to as a signature ion (or reporter ion). Various reporter ions of an N-methyl piperazine reporter moiety are illustrated in FIG. 5. The molecular formulas of the ions are $^{13}CC_5H_{13}N_2^+$, $^{13}CC_5H_{13}^{15}NN^+$, $^{13}C_2C_4H_{13}^{15}NN^+$ and $^{13}C_3C_3H_{13}^{15}NN^+$.

When ionized, the signature ion (i.e. reporter ion) can comprise one or more net positive or negative charges. Thus, the reporter ion can comprise one or more acidic groups and/or basic groups since such groups can be easily ionized in a mass spectrometer. For example, the reporter moiety can comprise one or more basic nitrogen atoms (positive charge) and/or one or more ionizable acidic groups such as a carboxylic acid group, sulfonic acid group or phosphoric acid group (negative charge) provided that on balance there are more of one or the other of the basic or acidic groups such that the reporter moiety produces a reporter ion comprising a net positive or negative charge. Non-limiting examples of reporter moieties comprising at least one basic nitrogen include substituted or unsubstituted morpholine, piperidine or piperazine containing compounds.

A unique reporter moiety can be associated with a sample of interest thereby labeling one or multiple analytes of that sample with said unique reporter moiety. In this way information about the unique reporter moiety (generally detected as a signature ion (i.e. reporter ion) in a mass spectrometer) can be associated with information about one or all of the analytes of said sample.

However, the unique reporter moiety need not be physically linked to an analyte when the signature ion is determined. Rather, the unique gross mass of the signature ion can, for example, be determined in a second mass analysis of a tandem mass analyzer, after ions of the labeled analyte are fragmented to thereby produce daughter fragment ions and signature ions.

The determined signature ion can be used to identify the sample from which a determined analyte originated. Further, the amount (often expressed as a concentration and/or quantity) of the unique signature ion, either relative to the amount of other signature ions or relative to the signature ion associated with a calibration standard (e.g. an analyte expected in the sample and labeled with a specific reporter moiety), can be used to determine the relative and/or absolute amount (often expressed as a concentration and/or quantity) of analyte in the sample or samples (such as those used to form a sample mixture). In some embodiments, rather than using an internal calibration standard, absolute quantification can be determined based on comparison of the peak intensities of the various signature ions with a calibration curve. Therefore information, such as the amount of one or more analytes in a particular sample, can be associated with the reporter moiety that is used to label each particular sample. Where the identity of the analyte or analytes is also determined, that information can be correlated with information pertaining to the different signature ions to thereby facilitate the determination of the identity and amount of each labeled analyte in one sample or in a plurality of samples.

In some embodiments, the reporter moiety can comprise a nitrogen atom covalently linked to the methylene carbon of a substituted or unsubstituted N-alkylated acetic acid moiety wherein the substituted or unsubstituted methylene carbon but not the carbonyl group of the carboxylic acid (or thiocarboxylic acid) group of the acetic acid moiety is part of the reporter. Thus, in some embodiments, the carboxylic acid (or thio carboxylic acid) group can be used to link the reporter to the linker but it is not considered part of the reporter. The nitrogen atom can be alkylated with one, two or three groups. For example, the moiety comprising the nitrogen atom can be a substituted primary amine such as a methyl, ethyl or propyl group or a substituted secondary amine such as dimethylamine, diethylamine, di-n-propylamine or diisopropylamine. Thus, for example the reporter moiety "RP" can be illustrated by formulas $X^1, X^2, X^3, X^4, X^5, X^6, X^7, X^8$, or $X^9$ as follows wherein the reporter moiety "RP" is set off by the bracket:

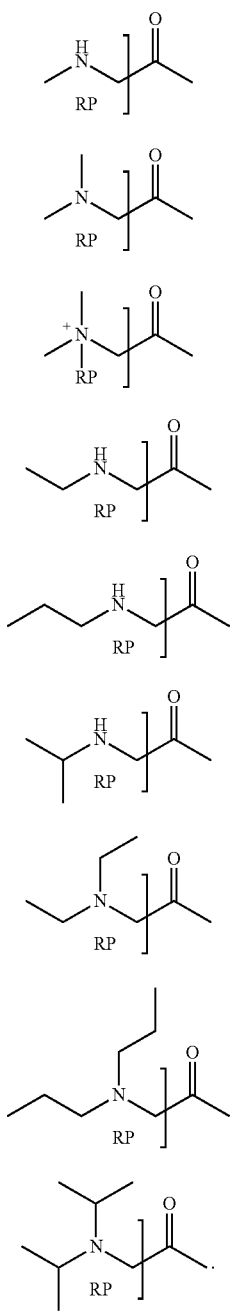

The reporter moiety can be a 5, 6 or 7 membered heterocyclic ring comprising a ring nitrogen atom covalently linked to the methylene carbon of a substituted or unsubstituted N-alkylated acetic acid moiety to which the analyte is (directly or indirectly) linked through the carbonyl carbon of the N-alkyl acetic acid moiety and wherein the substituted or unsubstituted methylene carbon but not the carbonyl group of carboxylic acid group is part of the reporter. The heterocyclic ring can be aromatic or non-aromatic. Thus, the reporter moiety can be represented by formula Y-J- wherein the group Y can represent the 5, 6 or 7 membered heterocyclic ring and the group J can represent the substituted or unsubstituted methylene group of the substituted or unsubstituted acetic acid moiety. The heterocyclic ring can be substituted or unsubstituted. For example, substituents of the heterocyclic moiety can include alkyl, alkoxy and/or aryl groups. The substituents can comprise protected or unprotected groups, such as amine, hydroxyl or thiol groups, suitable for linking the analyte to a support (See FIG. 6). The heterocyclic ring can comprise additional heteroatoms such as one or more silicon, nitrogen, oxygen and/or sulfur atoms. Thus, for example the reporter moiety "RP" can be illustrated by formulas $X^{10}, X^{11}, X^{12}, X^{13}, X^{14}, X^{15}, X^{16}, X^{17}, X^{18}, X^{19}, X^{20}, X^{21}, X^{22}, X^{23}, X^{24}, X^{25}$, or $X^{26}$ as follows wherein the reporter moiety "RP" is set off by the bracket:

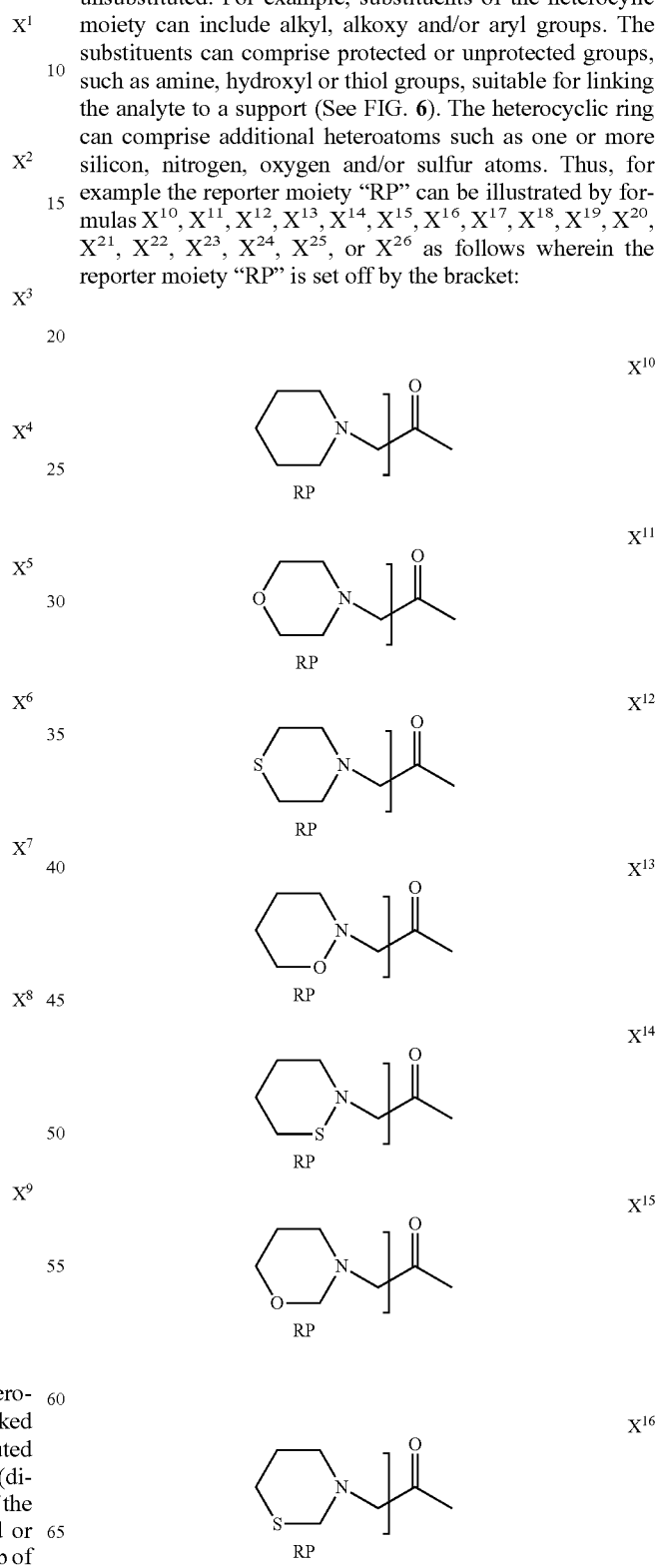

-continued

X¹⁷ 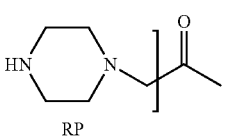
RP

X¹⁸ 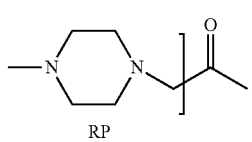
RP

X¹⁹ 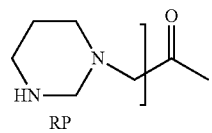
RP

X²⁰ 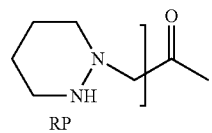
RP

X²¹ 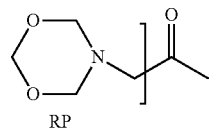
RP

X²² 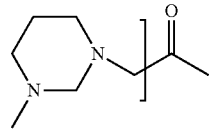
RP

X²³ 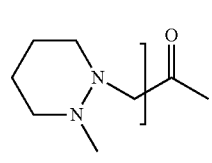
RP

X²⁴ 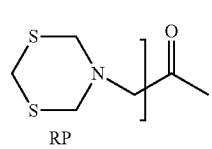
RP

X²⁵ 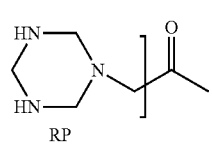
RP

X²⁶ 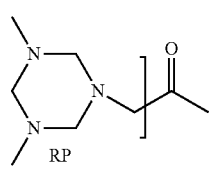
RP

The reporter moiety can be selected so that it does not substantially sub-fragment under conditions typical for the analysis of the analyte. For the avoidance of any doubt, this is an optional, not a required, feature. For example, the reporter can be chosen so that it does not substantially sub-fragment under conditions of dissociative energy applied to cause fragmentation of the labeled analyte in a mass spectrometer. By "does not substantially sub-fragment" we mean that fragments of the reporter are difficult or impossible to detect above background noise when applied to the successful determination of the labeled analyte.

In some embodiments, the gross mass of a reporter ion can be intentionally selected to be different as compared with the mass of the analyte sought to be determined or the mass of any of the expected fragments of the analyte (i.e. a "quiet zone"). For example, where proteins or peptides are the analytes, the gross mass of the reporter ion can be chosen to be different as compared with any naturally occurring amino acid or peptide, or expected fragment ion thereof. This can facilitate analyte determination since, depending on the analyte, the lack of any possible components of the sample having the same coincident mass can add confidence to the result of any analysis. Examples of mass ranges where little background can be expected for peptides can be found in Table 1.

TABLE 1

Possible "Quiet Zones" For Selection Of Label
Fragment Ion m/z Associated With Peptide Analysis
M/z start-end

| |
|---|
| 10-14 |
| 19-22 |
| 24-26 |
| 31-38 |
| 40-40 |
| 46-50 |
| 52-52 |
| 58-58 |
| 61-69 |
| 71-71 |
| 74-83 |
| 89-97 |
| 103-109 |
| 113-119 |
| 121-125 |
| 128-128 |
| 131-135 |
| 137-147 |
| 149-154 |
| 156-156 |
| 160-174 |
| 177-182 |
| 184-184 |
| 188-189 |
| 191-191 |
| 202-207 |
| 210-210 |
| 216-222 |
| 224-226 |

The reporter moiety can be non-polymeric. The reporter moiety can be selected to produce a signature ion of m/z that indicates its mass is less than 250 atomic mass units (amu). The reporter moiety can be selected to produce a signature ion of m/z less than 200 amu. The reporter moiety can be selected to produce a signature ion of m/z less than 150 amu. Such a small molecule can be easily determined in the second mass analysis, free from other components of the sample having the same coincident mass in the first mass analysis. In this context, the second mass analysis can be performed, typically in a tandem mass spectrometer (or, for example by post source decay in a single stage instrument), on selected ions that are determined in the first mass analysis. Because ions of a particular mass to charge ratio can be specifically selected out of the first mass analysis for possible fragmentation and further mass analysis, the non-selected ions from the first mass analysis are not carried forward to the second mass analysis and therefore do not contaminate the spectrum of the second mass analysis. Furthermore, the sensitivity of a mass spectrometer and the linearity of the detector (for purposes of quantification) can be quite robust in this low mass range. Additionally, the present state of mass spectrometer technology can allow for baseline mass resolution of less than one Dalton in this mass range. For all these reasons, reporters possessing the above described characteristics can provide quite accurate quantification of determined analytes from complex mixtures utilizing methods as described herein.

The Linker (or Balance) Moiety:

The linker (or balance) moiety (sometimes referred to by use of the shorthand "LK") of the labeling reagent or reagents can be used with embodiments of this invention to link the reporter moiety (RP) and the non-encoded detectable label (DL) to the analyte or the reactive group depending on whether or not a reaction with the analyte has occurred. The linker moiety can be branched or unbranched. For example, the linker can be branched where the reporter and the non-encoded detectable label each, independently of the other, are linked to the linker but may be linear where the non-encoded detectable label and reporter moiety are linked in sequence to the linker moiety (c.f. FIGS. 1a and 1b). The non-encoded detectable label may be linked directly or indirectly to the linker.

The linker can be selected to produce a neutral species (i.e. undergo neutral loss in a mass spectrometer) wherein both the bond that links the linker to the reporter moiety (i.e. the X bond) and the bond or group that links the linker to the analyte (in some embodiments this is Y) fragment in a mass spectrometer. In some embodiments, the linker moiety can be designed to sub-fragment when subjected to dissociative energy, including sub-fragmentation to thereby produce only neutral fragments of the linker. In some embodiments, the linker can be designed to produce one or more detectable fragments.

When used in a set and/or kit comprising a set of isomeric and/or isobaric labeling reagents, the linker moiety can comprise one or more heavy atom isotopes such that the mass of the linker moiety of each different reagent of the set compensates for the difference in gross mass between the reporter moieties for the different labeling reagents of the set such that the aggregate gross mass of the combination of the reporter moiety and the linker moiety is the same for each labeling reagent of the set. Thus, the aggregate gross mass (i.e. the gross mass taken as a whole) of the reporter/linker combination (i.e. the reporter/linker moiety) can be the same (on a gross basis) for each labeled analyte of a mixture or for the labeling reagents of set and/or kit. More specifically, the linker moiety can compensate for the difference in gross mass between reporter moieties of labeled analytes from different samples wherein the unique gross mass of the reporter moiety correlates with the sample from which the labeled analyte originated and the aggregate gross mass of the reporter/linker combination is the same for each labeled analyte of a sample mixture regardless of the sample from which it originated. In this way, the gross mass of identical analytes in two or more different samples can have the same gross mass when labeled and then mixed to produce a sample mixture.

For example, the labeled analytes, or the labeling reagents of a set and/or kit for labeling the analytes, can be isomers and/or isobars. Thus, if ions of a particular mass to charge ratio (taken from the sample mixture) are selected (i.e. selected ions) in a mass spectrometer from a first mass analysis of the sample mixture, identical analytes from the different samples that make up the sample mixture can be represented in the selected ions in proportion to their respective concentration and/or quantity in the sample mixture since they all have the same gross mass regardless of which label is linked to the analyte. Accordingly, the linker not only links the reporter and non-encoded detectable label to the analyte, it also serves to compensate for the differing masses of the unique reporter moieties to thereby harmonize the gross mass of the reporter/linker moiety in the labeled analytes of the various samples.

Because the linker can act as a mass balance for the reporter moieties in the labeling reagents, the greater the number of atoms in the linker, the greater the possible number of different isomeric/isobaric labeling reagents of a set and/or kit. Stated differently, generally the greater the number of atoms that a linker comprises, the greater the number of potential reporter/linker combinations since isotopes can be substituted at most any position in the linker to thereby produce isomers and/or isobars of the linker portion wherein the linker portion is used to offset the differing masses of the reporter portion and thereby create a set of unique isomeric and/or isobaric labeling reagents. Such diverse sets of labeling reagents are particularly well suited for multiplex analysis of analytes in the same and/or different samples.

The total number of labeling reagents of a set and/or kit can be two, three, four, five, six, seven, eight, nine, ten, eleven, twelve, thirteen, fourteen, fifteen, sixteen, fifteen, sixteen, seventeen, eighteen, nineteen, twenty or more. Based upon mass balancing considerations, the diversity of the labeling reagents of a set or kit is limited only by the number of atoms of the reporter and linker moieties, the heavy atom isotopes available to substitute for the light isotopes and the various synthetic configurations in which the isotopes can be synthetically placed. As suggested above however, numerous isotopically enriched basic starting materials are readily available from manufacturers such as Cambridge Isotope Laboratories and Isotec. Such isotopically enriched basic starting materials can be used by the ordinary practitioner in synthetic processes used to produce sets of isobaric and/or isomeric labeling reagents or be used to produce the isotopically enriched starting materials (i.e. synthetically enriched compounds) that can be used in the synthetic processes used to produce sets of isobaric and/or isomeric labeling reagents.

The Reporter/Linker Combination (i.e. the Reporter/Linker Moiety):

The labeling reagents can comprise reporter moieties and linker moieties that are linked directly to each other through the bond X. As described above, the reporter/linker moiety can be identical in gross mass for each member of a set and/or kit of labeling reagents or for each labeled analyte in a mixture of labeled analytes. Moreover, the bond (i.e. bond X) that links the reporter moiety (directly or indirectly) to the linker moiety can be designed to fragment, in at least a portion of the selected ions, when subjected to dissociative energy thereby releasing the signature ion (i.e. the reporter ion) from the linker moiety, linker/analyte and/or linker/analyte/non-encoded detectable label moiety. Accordingly, the gross mass of the signature ion (observed as a mass to charge (m/z) ratio in the mass spectrometer) and its intensity (i.e. its peak intensity) can be observed directly in MS/MS analysis.

The reporter/linker moiety can comprise various combinations of the same or different heavy atom isotopes amongst the various labeling reagents of a set or kit. In the scientific literature this has sometimes been referred to as "coding", "isotope coding" or simply as "encoding". For example, Abersold et al. has disclosed the isotope coded affinity tag (ICAT; see WO00/11208). In one respect, the reagents of Abersold et al. differ from the labeling reagents described herein that Abersold does not teach two or more same mass labeling reagents such as isomeric and/or isobaric labeling reagents. Rather, Abersold et al. teach about "light" and "heavy" versions of their labeling reagents. Versions of the ICAT reagent that comprise a non-encoded detectable label are (sometimes referred to as VICAT) described in WO 2004/019000, in Lu et al., *Anal. Chem.*, 76: 4104-4111 (2004) and in Bottari et al, *Bioconjugate Chemistry*, 15(2): 380-388 (2004).

Figure 6:
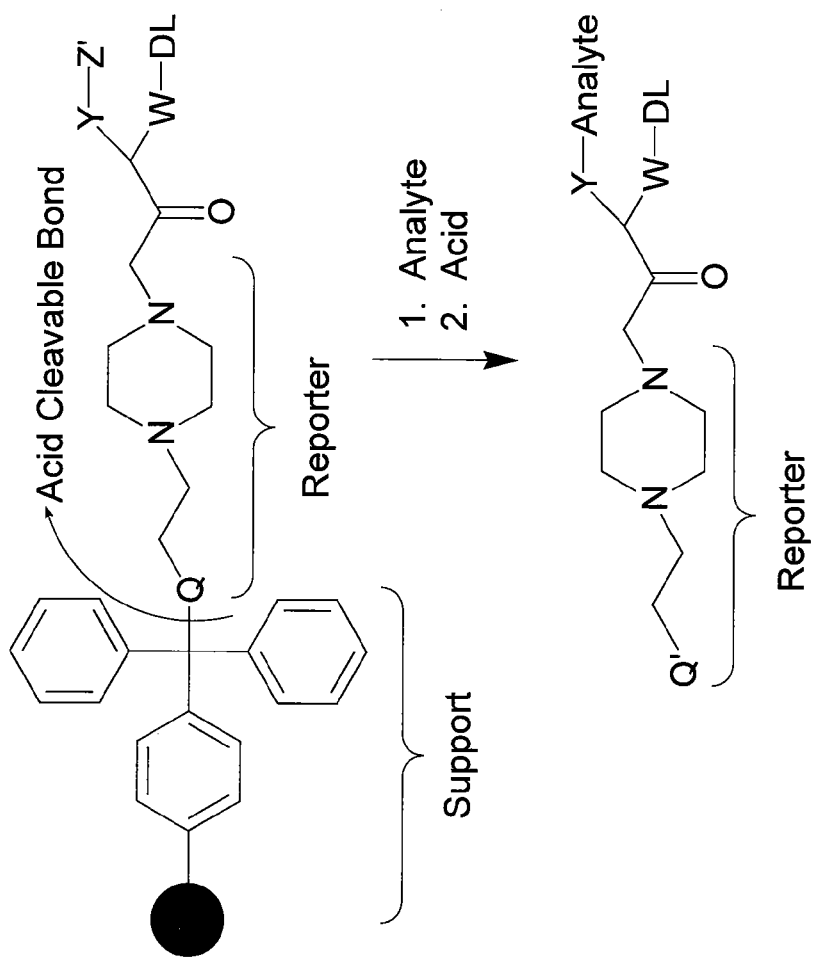
FIG. 6 is an illustration of the process of using a support-bound labeling reagent to prepare a support-bound labeled analyte followed by release of the labeled analyte from the solid support.

In some embodiments, the reporter and/or linker moieties can comprise an atom or group that can be used to immobilize the labeling reagent or labeled analyte to a support. Immobilization can be direct or indirect. For example, direct immobilization can occur if an atom or group (e.g. an alkyl amine substituent of the reporter) associated with the reporter interacts directly with a reactive group (e.g. the reactive group of a cleavable linker) of the support to effect mobilization. By comparison, indirect immobilization occurs if, for example, a substituent of the reporter (e.g. an alkylamine substituent of the reporter and/or linker) is modified (e.g. is biotinylated) and the modifying group interacts with a reactive group of the support (e.g. avidin or streptavidin) to effect immobilization. Consequently, this invention contemplates embodiments wherein the analytes can be reacted with support-bound labeling reagents wherein each support comprises a unique labeling reagent such that different samples are reacted with different supports as well as embodiments where each different sample is reacted with a different labeling reagent and the reaction products are thereafter immobilized to the same or to different supports. In either case, a sample mixture is generally obtained by cleaving the labeled analytes from the support(s) for analysis by mass spectrometry (See: FIG. 6). The released labeled analytes of each sample can be optionally collected separately or they can be mixed during the cleavage process to thereby form a sample mixture. If collected, the released labeled analytes can thereafter be mixed to form a sample mixture.

The Non-Encoded Detectable Label:

The labeling reagents described herein comprise a non-encoded detectable label (sometimes referred to by use of the shorthand "DL"). Non-limiting examples of non-encoded detectable labels (moieties) that can be used with the labeling reagents disclosed herein include, but are not limited to, a chromophore, a fluorophore, a spin label, an enzyme or a chemiluminescent compound. By "non-encoded" we mean that the detectable label isn't synthetically enriched with one or more heavy atom isotopes. Accordingly, the non-encoded detectable label doesn't produce a reporter ion (signature ion) and doesn't represent part of the linker (balance) moiety.

Non-limiting examples of fluorophores include 5(6)-carboxyfluorescein (Flu), 6-((7-amino-4-methylcoumarin-3-acetyl)amino)hexanoic acid (Cou), 5(and 6)-carboxy-X-rhodamine (Rox), Cyanine 2 (Cy2) Dye, Cyanine 3 (Cy3) Dye, Cyanine 3.5 (Cy3.5) Dye, Cyanine 5 (Cy5) Dye, Cyanine 5.5 (Cy5.5) Dye Cyanine 7 (Cy7) Dye, Cyanine 9 (Cy9) Dye (Cyanine dyes 2, 3, 3.5, 5 and 5.5 are available as NHS esters from Amersham, Arlington Heights, Ill.) or the Alexa dye series (Molecular Probes, Eugene, Oreg.).

Non-limiting examples of enzymes include polymerases (e.g. Taq polymerase, Klenow DNA polymerase, T7 DNA polymerase, Sequenase, DNA polymerase 1 and phi29 polymerase), alkaline phosphatase (AP), horseradish peroxidase (HRP), soy bean peroxidase (SBP)), ribonuclease and protease.

For sets of isomeric and/or isobaric labeling reagents, each non-encoded detectable label has the same gross mass and same net charge as the other non-encoded detectable labels of the labeling reagents of the set under similar conditions. Each different non-encoded detectable label is independently detectable of the others in the set. For example, the fluorophores (i.e. the non encoded detectable labels) of the labeling reagents illustrated in FIGS. 8a and 8b are believed to have distinguishable fluorescent profiles, identical net charges at physiological pH and have the same nominal gross mass.

Because each non-encoded detectable label is independently detectable within a set, in some embodiments, the non-encoded detectable labels can be used for determining where there appears to be a difference in relative concentrations of a particular labeled analyte (or other condition of interest) during the electrophoretic separation as described below. Thus, in some embodiments, analytes of interest can be judiciously selected for MS analysis (and to some degree quantified) based upon an (electrophoretic separation and) analysis that precedes the MS analysis and quantification. In this way, $MS^n$ analysis of analytes that don't seem to have changed in amount, or don't seem to be different in relative quantification, with reference to an expected amount, can be skipped thereby permitting more efficient use of time and resources.

The Bond X:

X is a bond between an atom of the reporter and an atom of the linker moiety or non-encoded detectable label. Bond X of the various labeling reagents disclosed herein can fragment, in at least a portion of selected ions, when subjected to dissociative energy. Therefore, the dissociative energy level can be adjusted in a mass spectrometer so that bond X can fragment in at least a portion of the selected ions of the labeled analytes. Fragmentation of bond X releases the reporter from the analyte so that the reporter (i.e. signature ion) can be determined independently from ions of the analyte.

The Bond or Linker Group Y:

Y is a bond or linking group that links the linker moiety ("LK") to the reactive group ("RG"). Whether a bond or a linking group, Y is optionally fragmentable by application of dissociative energy in a mass spectrometer. If Y is a linking group, it can be an alkylene group, an alkenylene group, an alkynylene group, an arylene group, or an arylalkylene group. If Y is a linking group, it may optionally comprise one or more heavy atom isotopes. If Y is a linking group and the labeling reagent is used in a set of isomeric and/or isobaric labeling reagents, its gross mass is the same for every labeling reagent of the set.

If Y is a fragmentable, fragmentation of Y releases the reporter/linker/non-encoded detectable label moiety from the analyte, or a fragment thereof depending on whether or not bond X has already been fragmented. If a bond, bond Y can be more labile than bond X. Bond X can be more labile than bond Y. Bonds X and Y can be of the same relative lability.

When the analyte of interest is a protein or peptide, the relative lability of bonds X and Y can be adjusted with regard to an amide (peptide) bond. Bond X, bond Y or both bonds X and Y can be more, equal or less labile as compared with a typical amide (peptide) bond. For example, under conditions of dissociative energy, bond X and/or bond Y can be less prone to fragmentation as compared with the peptide bond of a $Z'''$-pro dimer or $Z'''$-asp dimer, wherein $Z'''$ is any natural amino acid, pro is proline and asp is aspartic acid. In some embodiments, bonds X and Y will fragment with approximately the same level of dissociative energy as a typical amide bond. In some embodiments, bonds X and Y will fragment at a greater level of dissociative energy as compared with a typical amide bond.

Bonds X and Y can also exist such that fragmentation of bond Y results in the fragmentation of bond X, and vice versa. In this way, both bonds X and Y can fragment essentially simultaneously such that no substantial amount of analyte, or daughter fragment ion thereof, comprises a partial label in the second mass analysis. By "substantial amount of analyte" we mean that less than 25%, and preferably less than 10%, of partially labeled analyte can be determined in the MS/MS spectrum.

Because in some embodiments there can be a clear demarcation between labeled and unlabeled fragments of the analyte in the spectra of the second mass analysis (MS/MS), this feature can simplify the identification of the analytes from computer assisted analysis of the daughter fragment ion spectra. Moreover, because the fragment ions of analytes can, in some embodiments, be either fully labeled or unlabeled (but not partially labeled) with the reporter/linker/detectable moiety, there can be little or no scatter in the masses of the daughter fragment ions caused by isotopic distribution across fractured bonds such as would be the case where isotopes were present on each side of a single labile bond of a partially labeled analyte routinely determined in the second mass analysis.

The Bond or Linker Group W:

W is a bond or linking group that links the linker moiety ("LK") to the non-encoded detectable label ("DL"). W is optionally cleavable by application of light, heat or chemical reagent(s) and/or fragmentable (i.e. cleavable) by application of dissociative energy in a mass spectrometer. If W is a linking group, it can be an alkylene group, an alkenylene group, an alkynylene group, an arylene group or an arylalkylene group. If W is a linking group, it may optionally comprise one or more heavy atom isotopes. If W is a linking group and the labeling reagent is used in a set of isomeric and/or isobaric labeling reagents, its gross mass is the same for every labeling reagent of the set. In some embodiments, where W is a linking group, W can comprise, for example, a cleavable moiety such as XAL, PAL or HMPB as described in more detail in: Kates et al., *Solid Phase Synthesis: A Practical Guide*, Marcel Dekker, Inc., New York, 2000.

Support-Bound Labeling Reagents Comprising Cleavable Linkers:

According to some embodiments, the analytes from a sample can be reacted with a solid support comprising a labeling reagent (each sample being reacted with a different solid support and therefore labeled analytes of each sample comprises a different reporter moiety) and the components of the sample that do not react with the reactive group can be optionally washed away. The labeled analyte or analytes can then be removed from each solid support by treating the support under conditions that cleave a cleavable linker and thereby release the reporter-linker-non-encoding detectable label/analyte complex from the support. Each support can be similarly treated under conditions that cleave the cleavable linker to thereby obtain two or more different samples, each sample comprising one or more labeled analytes wherein the labeled analytes associated with a particular sample can be identified and/or quantified by the unique reporter moiety linked thereto. The collected samples can then be mixed to form a sample mixture, as described below.

Various supports are commercially available that can be used to attach a labeling reagent to the support through a cleavable linker. In some embodiments, the labeling reagent can be attached to the support through the reporter moiety. Generally, the labeling reagent will comprise a nucleophilic or electrophilic group that can react with a functional group of the cleavable linker to thereby cleavably link the labeling reagent to the support. In some embodiments, the labeling reagent can be synthesized on the support bearing the cleavable linker. In still other embodiments, the labeling reagent comprising the cleavable linker can be reacted with the support to thereby form the support-bound labeling reagent comprising the cleavable linker.

For example, the amino, hydroxyl or thiol group of a reporter moiety of a labeling reagent can be reacted with the cleavable linker of a suitable support. The cleavable linker can be a "sterically hindered cleavable linker". Cleavage of the cleavable linker will release the label or a labeled analyte from the support. Non-limiting examples of sterically hindered solid supports include: Trityl chloride resin (trityl-Cl, Novabiochem, P/N 01-64-0074), 2-Chlorotrityl chloride resin (Novabiochem, P/N 01-64-0021), DHPP (Bachem, P/N Q-1755), MBHA (Applied Biosystems P/N 400377), 4-methyltrityl chloride resin (Novabiochem, P/N 01-64-0075), 4-methoxytrityl chloride resin (Novabiochem, P/N 01-64-0076), Hydroxy-(2-chorophnyl)methyl-PS (Novabiochem, P/N 01-64-0345), Rink Acid Resin (Novabiochem P/Ns 01-64-0380, 01-64-0202), NovaSyn TGT alcohol resin (Novabiochem, P/N 01-64-0074). Numerous other cleavable linkers are known in the art and can be used to prepare suitable supports using no more than commercially available materials, routine experimentation and the teachings provided herein.

For example, the reporter moiety can be a 5, 6 or 7 member heterocyclic ring comprising an atom or group that facilitates the cleavable linkage of it to a suitable support. For example, the group can be an alkylene, alkenylene, alkynylene, arylene or alkylarylene group comprising an amino, hydroxyl or thiol group. In some embodiments, the heterocyclic ring doesn't require an additional functional group. For example, the atom that is bound to the cleavable linker can be the secondary nitrogen of a piperazine ring. A discussion of exemplary piperazine compounds and methods for their manufacture can be found in published United States Patent Application No: US 2004-0219685 A1. Reaction of the amino, hydroxyl or thiol group of the reporter moiety with the support comprising the linker moiety can form the support comprising the labeling reagent. Reaction of the support with the support-bound labeling reagent can produce the support-bound labeled analyte. Since the cleavable linker can be selected to be cleavable by light, heat or chemical reagent(s), appropriate treatment will release the labeled analyte(s) that can be used to produce a sample mixture as described below.

With reference to FIG. 6, an exemplary labeling reagent cleavably linked to a support is illustrated. As illustrated, a trityl group linked to the beaded support is the cleavable linker (e.g. Trityl chloride resin (trityl-Cl, Novabiochem, P/N 01-64-0074). As illustrated, the linked functional group Q of an alkylated piperazine reporter moiety of the labeling reagent is cleavably linked to the support-bound trityl group and the leaving group Z' of the reactive group can be displaced by the functional group of the analyte to thereby form the support-bound labeled analyte. For example, the reactive group of the labeling reagent can be a carboxylic acid that is activated in-situ for reaction with an amine functional group of the analyte (e.g. a peptide) to thereby form the support-bound labeled analyte. As illustrated, treatment of the support with acid releases the labeled analyte from the support by regeneration of the functional group Q' of the reporter moiety of the labeling reagent.

Mass Spectrometers/Mass Spectrometry (MS):

The methods of this invention can be practiced using tandem mass spectrometers and other mass spectrometers that have the ability to select and fragment molecular ions. Tandem mass spectrometers (and to a lesser degree single-stage mass spectrometers) have the ability to select and fragment molecular ions according to their mass-to-charge (m/z) ratio, and then record the resulting fragment (daughter) ion spectra. More specifically, daughter fragment ion spectra can be generated by subjecting selected ions to dissociative energy (e.g. collision-induced dissociation (CID)). For example, ions corresponding to labeled peptides of a particular m/z ratio can be selected from a first mass analysis, fragmented and reanalyzed in a second mass analysis. Representative instruments that can perform such tandem mass analysis include, but are not limited to, magnetic four-sector, tandem time-of-flight, triple quadrupole, ion-trap, and hybrid quadrupole time-of-flight (Q-TOF) mass spectrometers.

These types of mass spectrometers may be used in conjunction with a variety of ionization sources, including, but not limited to, electrospray ionization (ESI) and matrix-assisted laser desorption ionization (MALDI). Ionization sources can be used to generate charged species for the first mass analysis where the analytes do not already possess a fixed charge. Additional mass spectrometry instruments and fragmentation methods include post-source decay in MALDI-MS instruments and high-energy CID using MALDI-TOF (time of flight)-TOF MS. For a recent review of tandem mass spectrometers please see: R. Aebersold and D. Goodlett, *Mass Spectrometry in Proteomics. Chem. Rev.* 101: 269-295 (2001).

Fragmentation By Dissociative Energy:

It is well accepted that bonds can fragment as a result of the processes occurring in a mass spectrometer. Moreover, bond fragmentation can be induced in a mass spectrometer by subjecting ions to dissociative energy. For example, the dissociative energy can be produced in a mass spectrometer by collision-induced dissociation (CID). Other non-limiting examples of dissociative energy that can be used to fragment ions in a mass spectrometer include, but are not limited to, collision activated dissociation (CAD), photoinduced dissociation (PID)), surface induced dissociation (SID)), electron induced dissociation (EID), electron capture dissociation (ECD)), thermal/black body infrared radiative dissociation (BIRD), post source decay, or combinations thereof. Those of ordinary skill in the art of mass spectrometry will appreciate that other exemplary techniques for imposing dissociative energy that cause fragmentation include, but are not limited to, photo dissociation, electron capture and surface induced dissociation.

The process of fragmenting bonds by collision-induced dissociation involves increasing the kinetic energy state of selected ions, through collision with an inert gas, to a point where bond fragmentation occurs. For example, kinetic energy can be transferred by collision with an inert gas (such as nitrogen, helium or argon) in a collision cell. The amount of kinetic energy that can be transferred to the ions is proportional to the number of gas molecules that are allowed to enter the collision cell. When more gas molecules are present, a greater amount of kinetic energy can be transferred to the selected ions, and less kinetic energy is transferred when there are fewer gas molecules present.

It is therefore clear that the application of dissociative energy in a mass spectrometer can be controlled. It is also well accepted that certain bonds are more labile than other bonds. The lability of the bonds in an analyte or the reporter/linker/non-encoded detectable label moiety depends upon the nature of the analyte and the nature of the reporter/linker/non-encoded detectable label moiety. Accordingly, the dissociative energy can be adjusted so that the analytes and/or the labeling reagents (e.g. the reporter/linker combinations) can be fragmented in a manner that is determinable. One of skill in the art will appreciate how to make such routine adjustments to the components of a mass spectrometer to thereby achieve the appropriate level of dissociative energy to thereby fragment at least a portion of ions of labeled analytes into signature ions (i.e. reporter ions) and daughter fragment ions.

For example, dissociative energy can be applied to ions that are selected/isolated from the first mass analysis. In a tandem mass spectrometer, the extracted ions can be subjected to dissociative energy, to thereby cause fragmentation, and then transferred to a second mass analyzer. The selected ions can have a selected mass to charge ratio. The mass to charge ratio can be within a range of mass to charge ratios depending upon the characteristics of the mass spectrometer. When collision induced dissociation is used, the ions can be transferred from the first to the second mass analyzer by passing them through a collision cell where the dissociative energy can be applied to thereby produce fragment ions. For example the ions sent to the second mass analyzer for analysis can include some, or a portion, of the remaining (unfragmented) selected ions (if any), as well as reporter ions (signature ions) and daughter fragment ions of the labeled analyte.

Analyte Determination By Computer Assisted Database Analysis:

In some embodiments, analytes can be determined based upon daughter-ion fragmentation patterns that are analyzed by computer-assisted comparison with the spectra of known or "theoretical" analytes. For example, the daughter fragment ion spectrum of a peptide ion fragmented under conditions of low energy CID can be considered the sum of many discrete fragmentation events. The common nomenclature differentiates daughter fragment ions according to the amide bond that breaks and the peptide fragment that retains charge following bond fission (Reopstorff et al., *Biomed. Mass Spectrom.*, 11: 601 (1988)). Charge-retention on the N-terminal side of the fissile amide bond results in the formation of a b-type ion. If the charge remains on the C-terminal side of the broken amide bond, then the fragment ion is referred to as a y-type ion. In addition to b- and y-type ions, the CID mass spectrum may contain other diagnostic fragment ions (these include ions generated by neutral loss of ammonia (−17 amu) from glutamine, lysine and arginine or the loss of water (−18 amu) from hydroxyl-containing amino acids such as serine and threonine); the diagnostic fragment ions as well as the b- and y-type ions all being daughter fragment ions. Certain amino acids have been observed to fragment more readily under conditions of low-energy CID than others. This is particularly apparent for peptides containing proline or aspartic acid residues, and even more so at aspartyl-proline bonds (Mak, M. et al., *Rapid Commun. Mass Spectrom.*, 12: 837-842 (1998)). Accordingly, the peptide bond of a $Z'''$-pro dimer or $Z'''$-asp dimer, wherein $Z'''$ is any natural amino acid, pro is proline and asp is aspartic acid, will tend to be more labile as compared with the peptide bond between all other amino acid dimer combinations.

For peptide and protein samples therefore, low-energy CID spectra contain redundant sequence-specific information in overlapping b- and y-series ions, internal fragment ions from the same peptide, and immonium and other neutral-loss ions. Interpreting such CID spectra to assemble the amino acid sequence of the parent peptide de novo is challenging and time-consuming but can be done. Recent advances in computer assisted de novo methods for sequencing are were described in Huang, Y., Ross, P, Smirnov, I, Martin, S. and Pappin, D. 2003, Proceedings of 6th International Symposium on MS in Health and Life Sciences, Aug. 24-28, 2003, San Francisco Calif. The most significant advances in identifying peptide sequences have been the development of computer algorithms that correlate peptide CID spectra with peptide sequences that already exist in protein and DNA sequence databases. Such approaches are exemplified by programs such as SEQUEST (Eng, J. et al. *J. Am. Soc. Mass Spectrom.*, 5: 976-989 (1994)) and MASCOT (Perkins, D. et al. *Electrophoresis*, 20: 3551-3567 (1999)).

In brief, experimental peptide CID spectra (MS/MS spectra) are matched or correlated with 'theoretical' daughter fragment ion spectra computationally generated from peptide sequences obtained from protein or genome sequence databases. The match or correlation is based upon the similarities between the expected mass and the observed mass of the daughter fragment ions in MS/MS mode. The potential match or correlation is scored according to how well the experimental and 'theoretical' fragment patterns coincide. The constraints on databases searching for a given peptide amino acid sequence are so discriminating that a single peptide CID spectrum can be adequate for identifying any given protein in a whole-genome or expressed sequence tag (EST) database. For other reviews please see: Yates, J. R. *Trends, Genetics,* 16: 5-8 (2000) and Yates, J. R., *Electrophoresis* 19: 893-900 (1998).

Accordingly, daughter fragment ion analysis of MS/MS spectra can be used not only to determine the analyte of a labeled analyte, it can also be used to determine analytes from which the determined analyte originated. For example, identification of a peptide in the MS/MS analysis can be can be used to determine the protein from which the peptide was cleaved as a consequence of an enzymatic digestion of the protein. It is envisioned that such analysis can be applied to other analytes, such as nucleic acids, lipids steroids and/or prostaglandins.

The X Bond and the Y Bond:

The bond between an atom of the reporter moiety and an atom of the linker moiety is the X bond. If a bond in a labeled analyte, the bond between an atom of the linker moiety and an atom of the analyte is the Y bond. In some embodiments, the X bond and the Y bond can fragment, in at least a portion of selected ions, when subjected to dissociative energy. Therefore, the dissociative energy can, in some embodiments, be adjusted in a mass spectrometer so that both the X bond and the Y bond fragment in at least a portion of the selected ions of the labeled analytes.

Fragmentation of the X bond releases the reporter moiety from the analyte so that the reporter ion can be determined independently from the analyte. Fragmentation of the Y bond releases the reporter/linker/non-encoded detectable label moiety from the analyte, or the linker from the analyte, depending on whether or not the Y bond has already fragmented. In some embodiments, the X bond can be more labile than the Y bond. In some embodiments, the Y bond can be more labile than the X bond. In some embodiments, the X and Y bonds can be of the same relative lability. Stated briefly, the X bond is designed to fragment to thereby release the reporter ion but the Y bond may, or may not, fragment in the various embodiments of this invention. If the labeling reagent doesn't comprise a fragmentable Y bond, daughter ion analysis can be adjusted so that the mass of any modification of analyte by the labeling reagent is compensated for in relevant analyses.

In some embodiments, when the analyte of interest is a protein or peptide, the relative lability of the X and Y bonds can be adjusted with regard to an amide (peptide) bond. The X bond, the Y bond or both bonds X and Y can be more, equal or less labile as compared with a typical amide (peptide) bond. For example, under conditions of dissociative energy, the X bond and/or the Y bond can be less prone to fragmentation as compared with the peptide bond of a $Z'''$-pro dimer or $Z'''$-asp dimer, wherein $Z'''$ is any natural amino acid, pro is proline and asp is aspartic acid. In some embodiments, the X bond and the Y bond can fragment with approximately the same level of dissociative energy as a typical amide bond. In some embodiments, the X and Y bonds can fragment at a greater level of dissociative energy as compared with a typical amide bond.

In some embodiments, the X bond and the Y bond can exist such that fragmentation of the X bond results in the fragmentation of the Y bond, and vice versa. In this way, both bonds X and Y can fragment essentially simultaneously such that no substantial amount of analyte, or daughter fragment ion thereof, comprises a partial label. By "substantial amount of analyte" we mean that less than 25%, and preferably less than 10%, of partially labeled analyte can be determined in the mass spectrometer (e.g. in MS/MS or $MS^{n'}$ analysis, wherein n' is an integer greater than 1).

Because in some embodiments there can be a clear demarcation between labeled and unlabeled fragments of the analyte in the mass spectra (e.g. in MS/MS analysis), this feature can simplify the identification of the analytes from computer assisted analysis of the daughter fragment ion spectra since no compensation for the remnants of the label need be applied to the mass calculations used to analyze the daughter fragment ions of an analyte. Moreover, because the fragment ions of analytes can, in some embodiments, be either fully labeled or unlabeled (but not partially labeled), there can be little or no scatter in the masses of the daughter fragment ions caused by isotopic distribution across fractured bonds such as would be the case where isotopes were present on each side of a single labile bond of a partially labeled analyte resulting from fragmentation of the labeled analyte caused by the application of dissociative energy levels.

The Labeling of Analytes:

As discussed previously, analytes can be labeled by reacting a functional group of the analyte with the reactive group of the labeling reagent. The functional group on the analyte can be one of an electrophilic group or a nucleophilic group and the functional group of the labeling reagent can be the other of the electrophilic group or the nucleophilic group. The electrophile and nucleophile can react to form a covalent link between the analyte and the labeling reagent.

The labeling reaction can take place in solution. In some embodiments, one of the analyte or the labeling reagent can be support-bound. The labeling reaction can sometimes be performed in aqueous conditions. Aqueous conditions can be selected for the labeling of biomolecules such as proteins, peptides and/or nucleic acids. The labeling reaction can sometimes be performed in organic solvent or a mixture of organic solvents. Organic solvents can be selected for analytes that are small molecules. Mixtures of water and organic solvent or organic solvents can be used across a broad range. For example, a solution of water and from about 5 percent to about 95 percent organic solvent or solvents (v/v) can be prepared and used for labeling the analyte. In some embodiments, a solution of water and from about 50 percent to about 95 percent organic solvent or solvents (v/v) can be prepared and used for labeling the analyte. In some embodiments, a solution of water and from about 65 percent to about 80 percent organic solvent or solvents (v/v) can be prepared and used for labeling the analyte. Non-limiting examples of organic solvents include N,N'-dimethylformamide (DMF), acetonitrile (ACN), N-Methyl pyrrolidine (NMP) and alcohols such as methanol, ethanol, propanol and/or butanol. Those of skill in the art will be able to determine appropriate solvent conditions to facilitate analyte labeling depending upon the nature of the labeling reagent and the nature of the analyte using no more than knowledge available in the art and the disclosure provided herein in combination with routine experimentation.

When performing a labeling reaction, the pH can be modulated. The pH can be in the range of 4-10. The pH can be outside this range. Generally, the basicity of non-aqueous reactions can be modulated by the addition of non-nucleophilic organic bases. Non-limiting examples of suitable bases include N-methylmorpholine, triethylamine and N,N-diisopropylethylamine. Alternatively, the pH of water containing solvents can be modulated using biological buffers such as (N-[2-hydroxyethyl]piperazine-N'-[2-ethanesulfonic acid) (HEPES) or 4-morpholineethane-sulfonic acid (MES) or inorganic buffers such as sodium carbonate and/or sodium bicarbonate. Because at least one of the reactive groups can be electrophilic, it can be desirable to select the buffer to not contain any nucleophilic groups. Those of skill in the art will, with the application of ordinary experimentation, be able to identify other buffers that can be used to modulate the pH of a labeling reaction so as to facilitate the labeling of an analyte with a labeling reagent. Accordingly, those of skill in the art will be able to determine appropriate conditions of solvent and pH to thereby facilitate analyte labeling depending upon the nature of the labeling reagent and the nature of the analyte using no more than the disclosure provided herein in combination with routine experimentation.

Sample Processing:

In certain embodiments of this invention, a sample can be processed prior to, as well as after, labeling of the analyte or analytes. Processing can facilitate the labeling of the analyte or analytes. The processing can facilitate the analysis of the sample components. Processing can simplify the handling of the samples. Processing can facilitate two or more of the foregoing.

For example, a sample can be treated with an enzyme or a chemical. The enzyme can be a protease (to degrade proteins and peptides), a nuclease (to degrade nucleic acids) or some other enzyme. The enzyme can be chosen to have a very predictable degradation pattern. Two or more proteases and/or two or more nuclease enzymes may also be used together, or with other enzymes, to thereby degrade sample components.

For example, the proteolytic enzyme trypsin is a serine protease that cleaves peptide bonds between lysine or arginine and an unspecific amino acid to thereby produce peptides that comprise an amine terminus (N-terminus) and lysine or arginine carboxyl terminal amino acid (C-terminus). In this way the peptides from the cleavage of the protein are predictable and their presence and/or quantity, in a sample from a trypsin digest, can be indicative of the presence and/or quantity of the protein of their origin. Moreover, the free amine termini of a peptide can be a good nucleophile that facilitates its labeling. Other exemplary proteolytic enzymes include papain, pepsin, ArgC, LysC, V8 protease, AspN, pronase, chymotrypsin and carboxypeptidase (e.g. carboxypeptidase A, B, C, etc).

For example, a theoretical protein G might produce three peptides (e.g. peptides B, C and D) when digested with a protease such as trypsin. Accordingly, a sample that has been digested with a proteolytic enzyme, such as trypsin, and that when analyzed is confirmed to contain peptides B, C and D, can be said to have originally comprised the protein G. The quantity of peptides B, C and D will also correlate with the quantity of the protein G in the sample that was digested. In this way, any determination of the identity and/or quantify of one or more of peptides B, C and D in a sample (or a fraction thereof), can be used to identify and/or quantify the protein G in the original sample (or a fraction thereof).

Because activity of the enzymes is predictable, the sequence of peptides that are produced from degradation of a protein of known sequence can be predicted (See above the discussion under the heading: "Analyte Determination By Computer Assisted Database Analysis"). With this information, "theoretical" peptide information can be generated. A determination of the 'theoretical" peptide fragments in computer assisted analysis of daughter fragment ions (as described above) from mass spectrometry analysis of an actual sample can therefore be used to determine one or more peptides or proteins in one or more unknown samples (Id.).

In some embodiments, sample processing can include treatment of precursors to the analyte or analytes to be labeled. For example, if the analyte or analytes to be labeled are peptides derived from a digested protein and the labeling reagent is, for this example, selected to react with amine groups (e.g. N-α-amine groups and N-ε-amine group of lysine) of the peptide or peptide analytes, the protein (the analyte precursor molecule) of the sample may be processed in a manner that facilitates the labeling reaction. In this example, the protein can be reduced with a reducing agent (e.g. tris[2-carboxyethyl]phosphine (TCEP)) and the thiol groups then blocked by reaction with a blocking reagent (e.g. methyl methanethiosulfonate (MMTS)). In this way the thiol groups of the protein are blocked and therefore do not interfere with the labeling reaction between the amines of the analytes and labeling reagent.

Those of skill in the art will appreciate that treatment of certain other precursor molecules can be performed using readily available reagents and protocols that can be adapted with the aid of routing experimentation. The precise choices or reagents and conditions can be selected depending on the nature of the analyte to be labeled and the labeling reagent.

In some embodiments, sample processing can include the immobilization of the analytes or analyte precursors to a solid support, whether labeled with a labeling reagent or not. Immobilization can include covalent immobilization as well as adsorption and other non-covalent means of immobilization (e.g. electrostatic immobilization). In some embodiments, immobilization can facilitate reducing sample complexity. In some embodiments, immobilization can facilitate analyte labeling. In some embodiments, immobilization can facilitate analyte precursor labeling. In some embodiments, immobilization can facilitate selective labeling of a fraction of sample components comprising a certain property (e.g. they comprise or lack cysteine moieties). In some embodiments, immobilization can facilitate purification. The immobilization can facilitate two or more of the foregoing.

Separation Including Separation of the Sample Mixture:

In some embodiments, the processing of a sample or sample mixture of labeled analytes can involve separation. One or more separations can be performed on the labeled and/or unlabeled analytes, labeled and/or unlabeled analyte precursors, or fractions thereof. One or more separations can be performed on one or more fractions obtained from a solid phase capture and/or other products of a separations process. Separations can be preformed on two or more of the foregoing sample types and different types of separations can be performed prior to mass analyses.

For example, a sample mixture comprising differentially labeled analytes from different samples can be prepared. By differentially labeled we mean that each of the labels comprises a unique property that can be identified. The labels described herein can comprise two independently detectable properties. Specifically, they can comprise a non-encoded detectable label as well as a unique reporter moiety that produces a unique "signature ion" in MS/MS (or $MS^{n'}$ analysis). For example, in order to analyze the sample mixture, components of the sample mixture can be separated and mass analysis performed on only a fraction of the sample mixture. In this way, the complexity of the analysis can be substantially reduced since separated analytes can be individually analyzed for mass thereby increasing the sensitivity of the analysis process. Of course, the analysis can be repeated one or more time on one or more additional fractions of the sample mixture to thereby allow for the analysis of all fractions of the sample mixture and thus a more complete analysis of the components of the sample mixture.

Separation conditions under which identical analytes that are differentially labeled co-elute at a concentration, or in a quantity, that is in proportion to their abundance in the sample mixture can be used to determine the amount of each labeled analyte in each of the samples that comprise the sample mixture provided that the amount of each sample added to the sample mixture is known. Accordingly, in some embodiments, separation of the sample mixture can simplify the analysis whilst maintaining the correlation between signals determined in the mass analysis (e.g. MS/MS analysis) with the amount of the differently labeled analytes in the sample mixture.

In some embodiments, a separation can be performed by chromatography. For example, liquid chromatography/mass spectrometry (LC/MS) can be used to effect sample separation and mass analysis. Moreover, any chromatographic separation process suitable to separate the analytes of interest can be used. For example, the chromatographic separation can be normal phase chromatography, reversed-phase chromatography, ion-exchange chromatography (i.e. anion exchange chromatography or cation exchange chromatography), size exclusion chromatography or affinity chromatography.

When analyzing sample mixtures comprising analytes labeled with the isomeric and/or isobaric labeling reagents described herein, electrophoretic separation can be particularly useful. Non-limiting examples of electrophoretic separations techniques that can be used include, but are not limited to, 1D electrophoretic separation, 2D electrophoretic separation and/or capillary electrophoretic separation (See: Westermeier, R., *Electrophoresis in Practice: A Guide to Methods and Applications of DNA and Protein Separations*, Wiley-VCH Verlan GmbH, Weinheim, Germany, 2005 and M. Khaledi, M., *High-Performance Capillary Electrophoresis: Theory, Techniques, and Applications*, John Wiley and Sons, Inc. New York, 1998). During or after the separation, the non-encoded detectable labels can be used to locate mixtures of labeled analytes that co-elute, wherein the mixture can comprise an analyte of interest differentially labeled with different isomeric and/or isobaric labels wherein the each different label indicates from which sample the analyte originated. Moreover, because the non-encoded detectable can be independently detectable, the relative amounts of the labeled analytes can, in some embodiments, be determined and this information used to judiciously select certain of the co-migrating labeled analytes (based upon certain criteria) for further analysis by mass spectrometry, thereby avoiding the need to analyze all possible labeled analytes present in the electrophoretic separation.

For example, the electrophoretic separation process can produce, for certain analytes, a mixture comprising an amount of each isobarically labeled analyte that is in proportion to the amount of that labeled analyte in the sample mixture. Furthermore, from the knowledge of how the sample mixture was prepared (portions of samples and other optional components (e.g. calibration standards added to prepare the sample mixture)), it is possible to relate the amount of labeled analyte in the sample mixture back to the amount of that labeled analyte in the sample from which it originated. Based upon the relative amounts observed, it is also possible to select only those labeled analytes that meet a certain criteria of interest (e.g. are different in relative intensity by greater than 10%) for further analysis. For example, certain mixtures of isolated co-migrating analytes can also be subjected to analysis in a mass spectrometer including analysis that provides quantification information.

Relative and Absolute Quantification Of Analytes:

In some embodiments, the relative quantification of differentially labeled identical analytes of a sample mixture is possible. For example, relative quantification of differentially labeled identical analytes is possible by comparison of the relative amounts (e.g. area and/or height of the peak reported) of reporter ion (i.e. signature ion) that are determined in the mass analysis (e.g. in the second mass analysis for a selected, labeled analyte observed in a first mass analysis). Stated differently, where each reporter ion can be correlated with information for a particular sample used to produce a sample mixture, the relative amount of that reporter ion, with respect to other reporter ions observed in the mass analysis, is the relative amount of that analyte in the sample mixture. Where components combined to form the sample mixture are known (e.g. the amount of each sample combined to form a sample mixture), the relative amount of the analyte in each sample used to prepare the sample mixture can be back calculated based upon the relative amounts of reporter ion observed for the labeled analyte of selected mass to charge. This process can be repeated for all of the different labeled analytes observed in the first mass analysis. In this way, the relative amount (often expressed in concentration and/or quantity) of each reactive analyte, in each of the different samples used to produce the sample mixture, can be determined.

In other embodiments, absolute quantification of analytes can be determined. For these embodiments, a known amount of one or more differentially labeled analytes (the calibration standard or calibration standards) can be added to the sample mixture or the intensity of the reporter ion can be correlated with a calibration curve.

A calibration standard can be an expected analyte that is labeled with an isomeric and/or isobaric label of the set of labels used to label the analytes of the sample mixture provided that the reporter moiety for the calibration standard is unique as compared with any of the samples used to form the sample mixture. Once the relative amount of reporter ion for the calibration standard, or standards, is determined with relation to the relative amounts of the reporter ion or ions for the differentially labeled analytes of the sample mixture, it is possible to calculate the absolute amount (often expressed in concentration and/or quantity) of all of the differentially labeled analytes in the sample mixture with reference to the amount of calibration standard or standards that was (were) added to the sample mixture. In this way, the absolute amount of each differentially labeled analyte (for which there is a calibration standard in the sample from which the analyte originated) can also be determined based upon the knowledge of how the sample mixture was prepared.

Alternatively, a calibration curve can be prepared by analysis of representative samples of labeled analytes, each sample comprising a different known amount of the labeled analyte. The intensities of the peaks of the reporter ion for the analyzed labeled analyte can be plotted with respect to the known amount of each labeled analyte to thereby generate the standard curve. Once prepared the intensity of a reporter ion in an unknown sample can be compared with the standard curve to thereby determine the amount of the analyte in a test sample.

Notwithstanding the foregoing, corrections to the intensity of the reporters ion (signature ions) can be made, as appropriate, for any naturally occurring, or artificially created, isotopic abundance within the reporter moieties. There are numerous ways to correct for isotopic abundance of impurities in the signature ions of reporter moieties. An example of such a correction can be found in published copending and co-owned United States Provisional Patent Application No. US 2005-0114042 A1, entitled: "Method and Apparatus For De-Convoluting A Convoluted Spectrum", filed on Aug. 12, 2004. Basically, the intensity of up-mass and down mass peaks associated with the isotopic cluster of a single labeling reagent can be determined by deconvolution of the convoluted spectrum of the overlapping isotopic clusters of the labeling reagents using mathematical formulas and calculations. Regardless of how the values are determined, the more care taken to accurately quantify the intensity of each reporter ion (i.e. signature ion), the more accurate will be the relative and absolute quantification of the analytes in the original samples.

Proteomic Analysis:

Embodiments of this invention can be used for complex analysis because samples can be multiplexed, analyzed and reanalyzed in a rapid and repetitive manner using mass analysis techniques. For example, sample mixtures can be analyzed for the amount of one or more analytes in one or more samples. The amount (often expressed in concentration and/or quantity) of the analyte or analytes can be determined for the samples from which the sample mixture was comprised. Because the sample processing and mass analyses can be performed rapidly, these methods can be repeated numerous times so that the amount of many differentially labeled analytes of the sample mixture can be determined with regard to their relative and/or absolute amounts in the sample from which the analyte originated.

One application where such a rapid multiplex analysis is useful is in the area of proteomic analysis. Proteomics can be viewed as an experimental approach to describe the information encoded in genomic sequences in terms of structure, function and regulation of biological processes. This may be achieved by systematic analysis of the total protein component expressed by a cell or tissue. Mass spectrometry, used in combination with the method, mixture, kit and/or composition embodiments of this invention is one possible tool for such global protein analysis. Accordingly, experimental analysis for which these labeling reagents can be used includes, but is not limited to, time course experiments, biomarker analysis, multiplex proteomic analysis, mudpit experiments, affinity pull-downs, determination of post-translational modifications (PTMs) and multiple control experiments.

II Compositions

In some embodiments, this invention pertains to compounds represented by formula I;

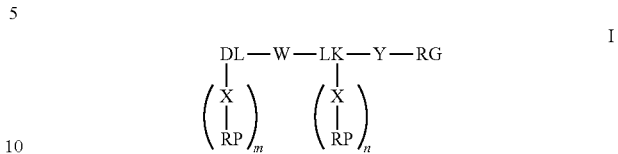

including a salt form and/or hydrate form thereof, wherein m and n are each 0 or 1 provided that m+n=1 and wherein the compound can be isotopically encoded with one or more heavy atom isotopes in the reporter moiety and/or linker moiety. As described in more detail above, the reactive group "RG" can comprising a nucleophile or an electrophile wherein said reactive group is capable of reacting with one or more reactive analytes of a sample to thereby form one or more labeled analytes. As described in more detail above, the reporter moiety "RP" can comprise a fixed charge or be ionizable in a mass spectrometer, wherein said reporter moiety is capable of producing a signature ion in a mass spectrometer upon fragmentation of bond X. As described in more detail above, "DL" can be a non-encoded detectable label. As described in more detail above, the linker moiety "LK" can be linear or branched, wherein LK links the reactive group to both the reporter moiety and the non-encoded detectable label. As described in more detail above, covalent bond X links the reporter moiety to the linker moiety or to the non-encoded detectable label wherein bond X is fragmentable by application of dissociative energy in a mass spectrometer. As described in more detail above, Y can be a covalent bond or linking group that links the reactive group to the linker moiety, wherein Y is optionally fragmentable by application of dissociative energy in a mass spectrometer. As described in more detail above, W can be a covalent bond or linking group that links the non-encoded detectable label to the linker moiety, wherein W is optionally cleavable by application of light, heat and/or chemical reagent(s) and/or fragmentable by application of dissociative energy in a mass spectrometer. In some embodiments, the compound is optionally linked to a solid support via a cleavable linker. In some embodiments, the compound is linked to the solid support through the reporter moiety. Certain fragmentation properties of labeling reagents of formula I are illustrated in FIG. 2a.

For example, the composition can be a compound represented by formula II or III;

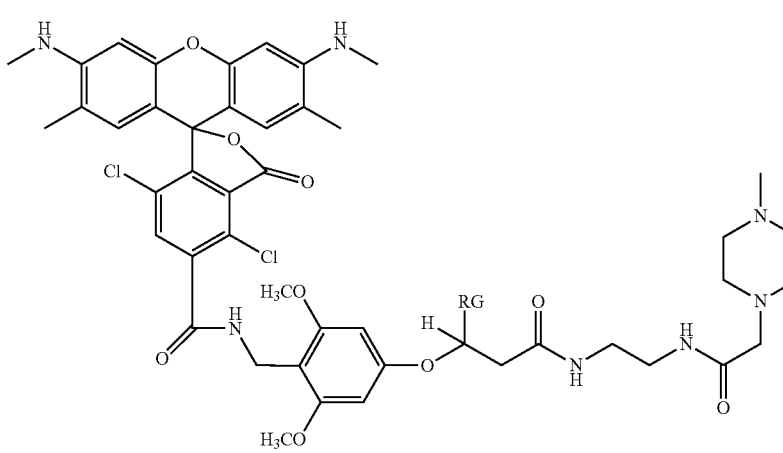

-continued

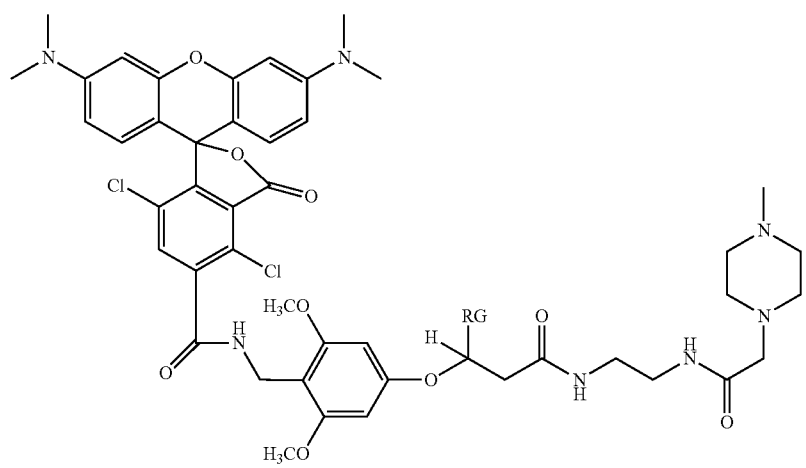

wherein RG is the reactive group and wherein the compound can be isotopically encoded (c.f. FIG. 8a). Compositions of formulas I, II or III can be used to label analytes for their analysis in methods that can utilize electrophoretic separations techniques in combination with mass spectrometry (e.g. tandem mass spectrometry) as discussed in more detail herein. The elements and certain fragmentation properties of labeling reagents of formula II and III are illustrated in FIG. 2b.

The compositions can comprise an isotopically enriched (i.e. encoded) reporter moiety and/or an isotopically enriched linker moiety. For example, the reporter moiety and/or linker moiety can each be isotopically enriched to comprise one or more heavy atom isotopes. In some embodiments, the reporter moiety and/or linker moiety can each be isotopically enriched to comprise two or more heavy atom isotopes. In some embodiments, the reporter moiety and/or linker moiety can each be isotopically enriched to comprise three or more heavy atom isotopes. In some embodiments, the reporter moiety and/or linker moiety can each be isotopically enriched to comprise four or more heavy atom isotopes.

In some embodiments, the reporter moiety can be cleavably linked to a support. By "cleavably linked" we mean that the reporter moiety, and anything covalently linked thereto, can be released from the support by treatment with an appropriate agent, such as light, heat and/or chemical reagent(s), based upon the nature of the cleavable linker chosen. Various supports comprising cleavable linkers are well known in the art. For example, various supports comprising a trityl moiety are sold commercially or can otherwise be prepared (e.g. Trityl chloride support (Trityl-Cl) or 2-Chlorotrityl chloride support). With reference to FIG. 6, an embodiment of a support-bound labeling reagent is illustrated wherein the reporter moiety of the labeling reagent comprises a bis-N-alkylated piperazine ring wherein one of the substituents of the N-alkylated piperazine ring is an alkyl group terminating with group functional Q, wherein Q is a functional group that can be released upon treatment of the support with acid to thereby produce the labeled analyte.

Thus, in some embodiments, this invention pertains to labeling reagent compositions represented by formula $I^{ss}$;

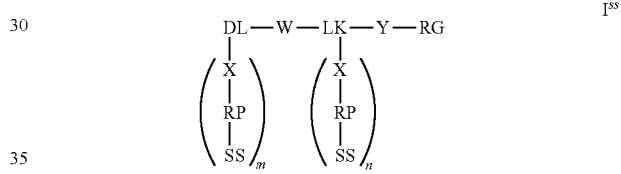

including a salt form and/or hydrate form thereof, wherein m and n are each 0 or 1 provided that m+n=1 and wherein the compound can be isotopically encoded with one or more heavy atom isotopes in the reporter moiety and/or linker moiety. As described in more detail above, the reactive group "RG" can comprising a nucleophile or an electrophile wherein said reactive group is capable of reacting with one or more reactive analytes of a sample to thereby form one or more labeled analytes. As described in more detail above, the reporter moiety "RP" can comprises a fixed charge or be ionizable in a mass spectrometer, wherein said reporter moiety is capable of producing a signature ion in a mass spectrometer upon fragmentation of bond X. As described in more detail above, "DL" can be a non-encoded detectable label. As described in more detail above, the linker moiety "LK" can be linear or branched, wherein LK links (directly or indirectly) the reactive group to both the reporter moiety and the non-encoded detectable label (c.f. FIGS. 1a and 1b). As described in more detail above, covalent bond X links the reporter moiety to the linker moiety or to the non-encoded detectable label wherein bond X is fragmentable by application of dissociative energy in a mass spectrometer. As described in more detail above, Y can be a covalent bond or linking group that links the reactive group to the linker moiety, wherein Y is optionally fragmentable by application of dissociative energy in a mass spectrometer. As described in more detail above, W can be a covalent bond or linking group that links the non-encoded detectable label to the linker moiety, wherein W is optionally cleavable by application of light, heat and/or chemical reagent(s) and/or fragmentable by application of dissociative energy in a mass spectrometer. As described in more detail above, SS is a solid support to which the reporter moiety of the composition is covalently linked through a cleavable linker. Certain fragmentation properties of labeling reagent of formula I$^{ss}$ are illustrated in FIG. 2a.

For example, the composition can be a compound represented by formula II$^{ss}$ or III$^{ss}$;

groups such as amines can be protonated by treatment with acid to thereby form salts of the amine. For example, piperazine containing labeling reagents can be obtained as a mono-TFA salt, a mono-HCl salt, a bis-TFA salt or a bis-HCl salt (See for Example, US Patent Application Publication No. US 2005-0148771 A1). One of ordinary skill in the art will surely appreciate how to manipulate the charge state and nature of II$^{ss}$

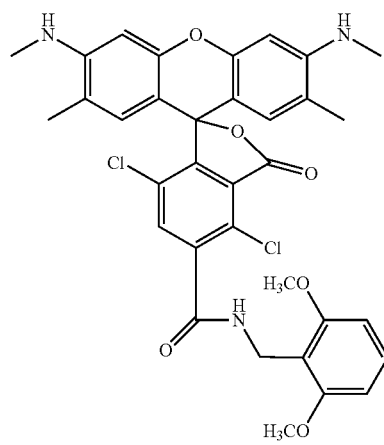
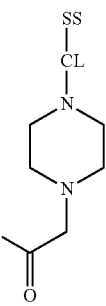

III$^{ss}$

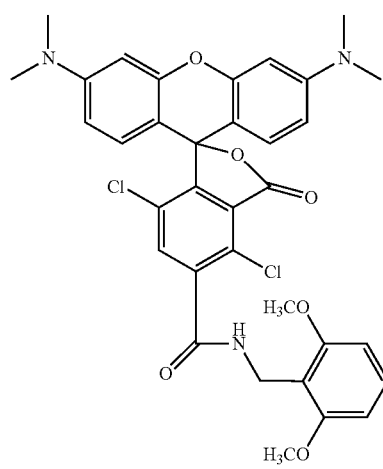
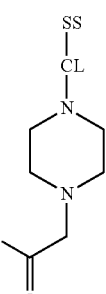

wherein RG is the reactive group, SS is the solid support and CL is the cleavable linker and wherein the compound can be isotopically encoded with one or more heavy atom isotopes in the reporter moiety and/or linker moiety. The elements and certain fragmentation properties of labeling reagents of formulas II$^{ss}$ and III$^{ss}$ are illustrated in FIG. 2c.

In some embodiments, the group RG of a compounds of formulas I, II, III, I$^{ss}$, II$^{ss}$ or III$^{ss}$, described above, can be a carboxylic acid, a sulfonic acid, a carboxylic acid halide, a sulfonyl halide, an active ester, a mixed anhydride, an isocyanate or an isothiocyanate group. In some embodiments, the group RG can be a malemide group, an alkyl halide group, an α-halo-acyl group, an α-halo thione group or an α-halo imine group. In some embodiments, the group RG can be a trityl-halide or a silyl-halide group. In some embodiments, the group RG can be an amine group, a hydroxyl group or a thiol group.

As stated, the compositions described above can exist in a salt form and/or hydrate form. Whether or not the composition exists as a salt form will typically depend upon the nature and number of substituents as well as the conditions under which it exists and/or was isolated. It is well known that basic any counterion the salt form of the compositions disclosed herein using no more than routine experimentation and the disclosure provided herein.

Whether or not a composition exists as a hydrate will also depend on the conditions under which it exists or was isolated. Hydrates merely comprise one or more complexed water molecules. This invention contemplates any possible hydrate form.

In some embodiments, this invention also pertains to analytes that are labeled with the labeling reagent compositions disclosed herein. Thus, in some embodiments, this invention pertains to labeled analyte compositions represented by formula I$^A$;

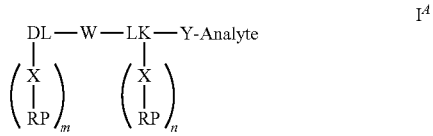

including a salt form and/or hydrate form thereof, wherein m and n are each 0 or 1 provided that m+n=1 and wherein RP, X, W and DL are as described for the composition of formula I, above and wherein the compound can be isotopically encoded with one or more heavy atom isotopes in the reporter moiety and/or linker moiety. As described in more detail above, the linker moiety "LK" can be linear or branched, wherein LK links (directly or indirectly) the analyte to both the reporter moiety and the non-encoded detectable label. As described in more detail above, Y can be a covalent bond or linking group that links the analyte to the linker moiety, wherein Y is optionally fragmentable by application of dissociative energy in a mass spectrometer.

Figure 3A:
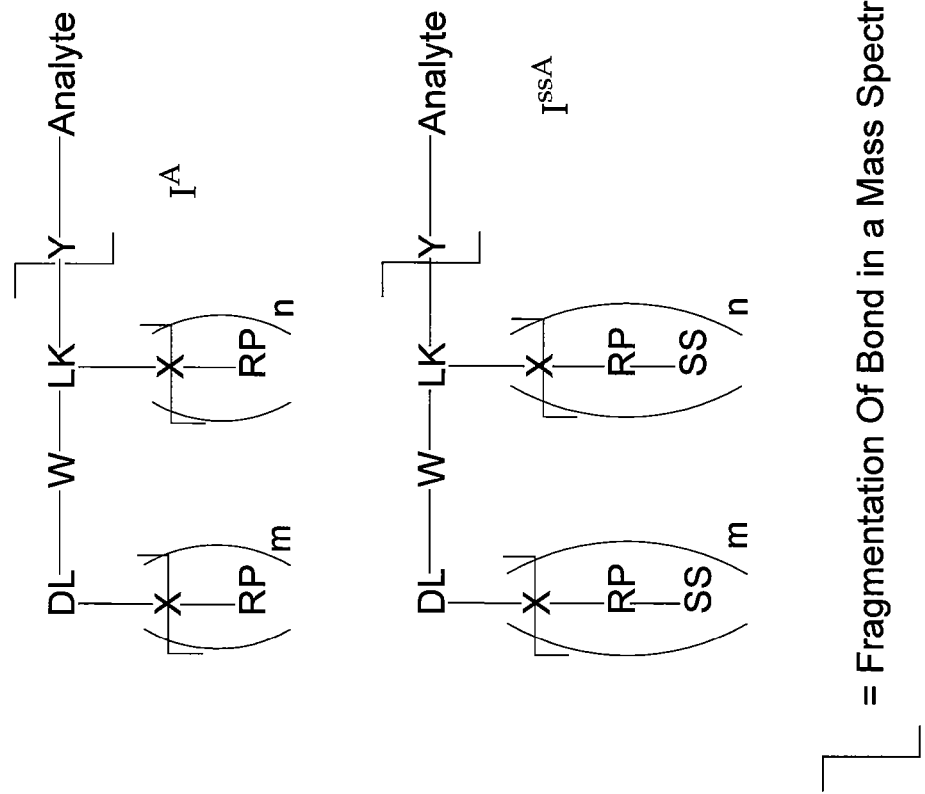
FIG. 3a is an illustration of the certain fragmentation characteristics of various labeled analytes represented by a generic formula.

In some embodiments, this invention also pertains to support-bound labeled analyte compositions represented by formula I$^{ssA}$;

including a salt form and/or hydrate form thereof, wherein m and n are each 0 or 1 provided that m+n=1 and wherein SS, RP, X, W and DL are as described for the composition of formula I$^{ss}$, above and wherein the compound can be isotopically encoded with one or more heavy atom isotopes in the reporter moiety and/or linker moiety. As described in more detail above, the linker moiety "LK" can be linear or branched, wherein LK links (directly or indirectly) the analyte to both the reporter moiety and the non-encoded detectable label. As described in more detail above, Y can be a covalent bond or linking group that links the analyte to the linker moiety, wherein Y is optionally fragmentable by application of dissociative energy in a mass spectrometer. Certain fragmentation properties of support-bound labeled analyte I$^{ssA}$ is illustrated in FIG. 3a.

For example, the support-bound labeled analyte can be represented by formula II$^{ssA}$ or III$^{ssA}$.

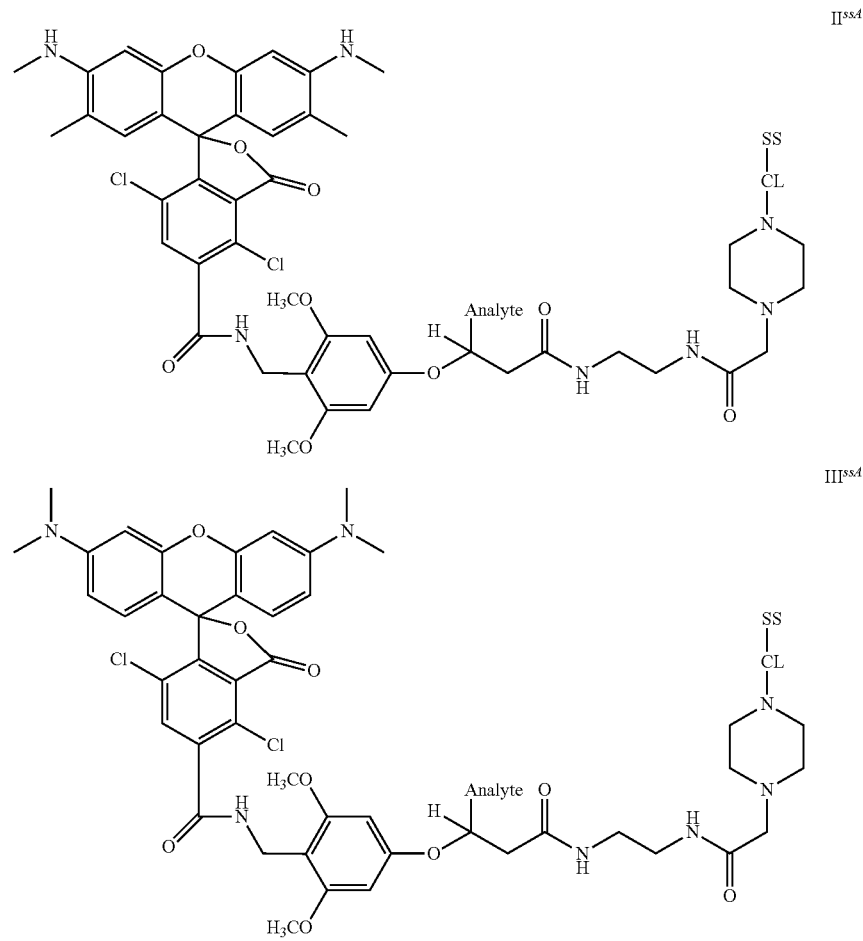

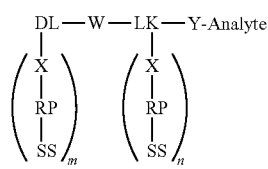

I$^{ssA}$ wherein SS is the solid support and CL is the cleavable linker. The elements and certain fragmentation properties of labeled analytes II$^{ssA}$ and III$^{ssA}$ are illustrated in FIG. 3c.

Analytes have been previously described herein. In some embodiments, the labeled analyte can be a labeled calibration standard. As described herein, calibration standards can be added to mixtures in known quantities to facilitate absolute quantitative analysis of an analyte of interest. Accordingly, in some embodiments, this invention pertains to an analyte, such as a peptide, protein, nucleic acid, carbohydrate, steroid, lipid, amino acid, vitamin or prostaglandin of interest, which has been labeled with a labeling reagent composition as described above for the purpose of being a calibration standard. Thus, the labeled calibration standard can be any analyte labeled with a labeling reagent as described herein. Typically, the labeling reagent is selected from a set of isomeric and/or isobaric labeling reagents so that it comprises a unique reporter moiety as compared with the labeling reagents used to label one or more test samples of interest for which quantification of said analyte in said test samples is of interest.

III. Methods for Labeling and Analysis

According to some embodiments of this invention, analytes can be labeled with labeling reagents described above and then determined. The labeled analyte, the analyte itself, one or more fragments of the analyte and/or fragments of the label, can be determined by mass analysis. In some embodiments, methods of this invention can be used for the analysis of different analytes in the same sample as well as for the multiplex analysis of the same and/or different analytes in two or more different samples. The two or more samples can be mixed to form a sample mixture. In multiplex analysis, labeling reagents can be used to determine from which sample of a sample mixture an analyte originated. The absolute and/or relative (with respect to the same analyte in different samples) amount (often expressed in concentration or quantity) of the analyte, in each of two or more of the samples combined to form the sample mixture, can be determined. Moreover, mass analysis of fragments of the analyte (e.g. daughter fragment ions) can be used to identify the analyte and/or the precursor to the analyte; such as where the precursor molecule to the analyte was degraded.

The samples used in the analysis may be any sample comprising an analyte or analytes that can be labeled with isotopically encoded versions of the labeling reagents. For example, the sample can be a crude or processed cell lysate, a body fluid, a tissue extract or a cell extract. In some embodiments, the sample can be processed before labeling to thereby prepare the analytes, or other components of the sample, for the labeling reaction. The sample can be a fraction from a separations process. The analyte in the sample can be any analyte that can be labeled with the labeling reagent. For example, the analyte can be a peptide, a protein, a nucleic acid, a carbohydrate, a lipid, a steroid, an amino acid, a vitamin, a prostaglandin or other small molecule with a molecular weight of less than 1500 daltons (Da). Other possible analyte types have been disclosed herein.

Consequently, in some embodiments, this invention also pertains to a method comprising reacting two or more samples, each sample comprising one or more reactive analytes, with a different labeling reagent of a set of labeling reagents to thereby produce two or more differentially labeled samples each comprising one or more labeled analytes. The labeling reagents can be selected from a set of isotopically encoded isomeric and/or isobaric labeling reagents wherein the different labeling reagents each comprise a reporter moiety of unique mass. The reporter moiety can be any reporter moiety having the properties disclosed herein. For example, the reporter moiety can comprise a substituted or unsubstituted piperidine, piperazine or morpholine group. Examples of other reporter moieties are also described above.

In some embodiments, this invention pertains to reacting two or more samples, each sample comprising one or more reactive analytes, with a different labeling reagent of a set of isotopically enriched isomeric and/or isobaric labeling reagents to thereby form two or more differentially labeled samples each comprising one or more labeled analytes; wherein the different labeling reagents of the set are represented by formula I;

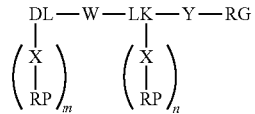

including a salt form and/or hydrate form thereof, wherein m and n are each 0 or 1 provided that m+n=1. According to the method, RG (as described in more detail above) is a reactive group comprising a nucleophile or an electrophile and said reactive group reacts with the one or more reactive analytes of the sample to thereby form the one or more labeled analytes. The reporter moiety "RP" (as described in more detail above) comprises a fixed charge or is ionizable in a mass spectrometer, wherein said reporter moiety is capable of producing a signature ion in a mass spectrometer upon fragmentation of bond X and wherein the gross mass of each reporter moiety, and its corresponding signature ion, is different for each labeling reagent of the set. The non-encoded detectable label "DL" (as described in more detail above) is a different independently detectable non-encoded detectable label for each reagent of the set, wherein each non-encoded detectable label has the same gross mass and same net charge as the other non-encoded detectable labels of the labeling reagents of the set. The linker moiety "LK" (as described in more detail above) can be linear or branched, wherein LK links (directly or indirectly) the reactive group to both the reporter moiety and the non-encoded detectable label and wherein the mass of the linker moiety of each different reagent of the set compensates for the difference in gross mass between the reporter moieties for the different labeling reagents of the set such that the aggregate gross mass of the combination for the reporter moiety and the linker moiety is the same for each labeling reagent of the set. The covalent bond X (as described in more detail above) links the reporter moiety to the linker moiety or to the non-encoded detectable label, wherein X is fragmentable by application of dissociative energy in a mass spectrometer. Y (as described in more detail above) is a covalent bond or linking group that links the reactive group to the linker moiety, wherein Y is optionally fragmentable by application of dissociative energy in a mass spectrometer, provided that if Y is a linking group its gross mass is the same for every labeling reagent of the set. W (as described in more detail above) is a covalent bond or linking group that links the non-encoded detectable label to the linker moiety, wherein W is optionally cleavable by application of light, heat and/or chemical reagent(s) and/or fragmentable by application of dissociative energy in a mass spectrometer, provided that if W is a linking group its gross mass is the same for every labeling reagent of the set.

In some embodiments, each differentially labeled sample is labeled with a labeling reagent of formula II or formula III;

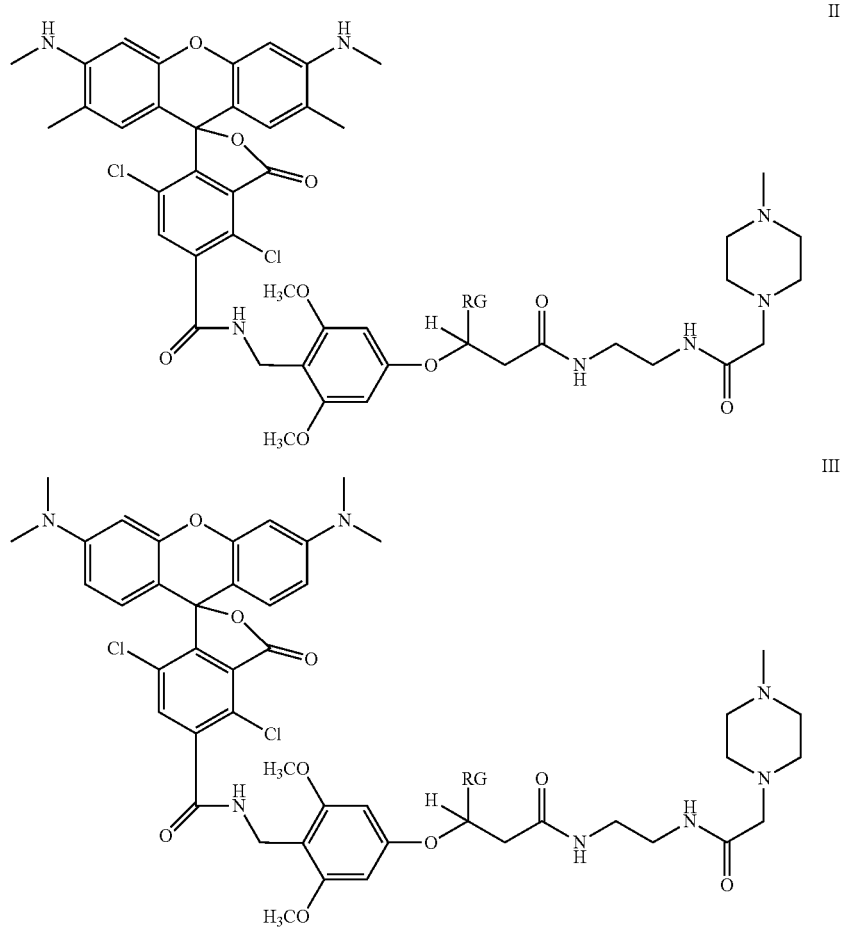

wherein RG is the reactive group. In some embodiments, compounds II and III can be isotopically encoded as shown in FIG. 8a.

The labeling process can produce two or more differentially labeled samples each comprising one or more labeled analytes. Once the analytes of each sample are labeled with the labeling reagent that is unique to that sample, two or more of the differentially labeled samples, or a portion thereof, can be mixed to produce a sample mixture. The sample mixture can optionally comprise one or more calibration standards as described above.

The volume and/or quantity of each sample of labeled analytes combined to produce the sample mixture can be recorded. The volume and/or quantity of each sample, relative to the total sample volume and/or quantity of the sample mixture, can be used to determine a ratio that can be used for determining the amount (often expressed in concentration and/or quantity) of an identified analyte in each sample from the analysis of the sample mixture. The sample mixture can therefore comprise a complex mixture wherein relative amounts of the same and/or different analytes can be identified and/or quantified, either by relative quantification of the amounts of analyte in each of the two or more samples or absolutely where a calibration standard is also added to the sample mixture or where a calibration curve for the signature ions is available.

In some embodiments, the method can further comprise separating electrophoretically the sample mixture, or a portion thereof. For example, the electrophoretic separation can be a 1D electrophoretic separation, a 2D electrophoretic separation and/or a capillary electrophoretic separation.

The two or more non-encoded detectable labels can be independently detectable. Because the labels can be independently detectable, it is possible to locate, detect and/or quantify labeled analytes during the electrophoretic separation. For example, the independently detectable non-encoded detectable labels can be used to locate labeled analytes in a 1-D or 2-D gel during and/or after separation. In some embodiments, the labels can be used to locate the labeled analytes in the gel after separation so that they can be excised from the gel and further analyzed, such as by mass spectrometry as discussed below.

For example the method can further comprise collecting one or more sub-samples of co-migrating differentially labeled analytes from the electrophoretic separation and optionally treating the one or more sub-samples under appropriate conditions to thereby cleave the non-encoded detectable label from the differentially labeled analytes of the sub-sample or sub-samples where m is 0, n is 1 and W is a covalent bond or linking group that is cleavable by application of light, heat or chemical reagent(s). Once the non-encoded detectable label has been cleaved from the analytes, they can be further analyzed, such as by mass spectrometry, wherein analysis of reporter moieties can be used to determine and/or confirm the relative and/or absolute quantity of the analyte associated with each sample used to form the sample mixture as discussed below.

In some embodiments, the non-encoded detectable labels can be used in capillary electrophoresis to detect and/or quantify labeled analytes as they exit the capillary column. Quantification can be determined based upon an analysis of the intensity of signal generated from the non-encoded detectable labels in a suitable detector. Preferentially (but not essentially), the non-encoded detectable labels of a set are selected to have similar migration properties (i.e. they co-migrate) during the electrophetic separation. In some embodiments, the co-migrating differentially labeled analytes can optionally be analyzed, based upon the independently detectable properties of the non-encoded detectable labels, for a condition of interest and judiciously selected for further analysis based upon satisfaction of the condition else be discarded based upon a failure to satisfy the condition. For example, if the co-migrating differentially labeled analytes satisfy the condition of interest (e.g. the relative amounts of the two independently detectable labels differs by more than 10%), the co-migrating differentially labeled analytes can be subsequently analyzed and quantified by mass spectrometry but if they don't, they are discarded. In this way, it is possible to achieve more efficient and economical use of the mass spectrometry equipment.

In some embodiments, the method can further comprise performing a first mass spectrometric analysis on one of the sub-samples, or a fraction thereof, using a first mass analyzer. Ions of a particular mass to charge ratio from the first mass analysis can then be selected. The selected ions can be subjected to dissociative energy levels (e.g. collision-induced dissociation (CID)) to thereby induce fragmentation. For example, fragmentation of bond X can cause release the ionized reporter moiety (i.e. the reporter ion or signature ion) from the labeled analyte. Fragmentation of the selected ions by the dissociative energy can also produce daughter fragment ions of the analyte that can be subsequently analyzed to determine the analyte and/or one or more precursors to the analyte. Thus, the ions (remaining selected ions, daughter fragment ions and ionized reporter moieties (i.e. signature ions)), or a fraction thereof, can then be directed to a second mass analyzer for analysis.

In the second mass analyzer, a second mass analysis can be performed on the selected ions, the signature ions and the daughter fragment ions or a fraction thereof. The second mass analysis can determine the gross mass (or m/z) and relative amount of each unique reporter ion that is present at the selected mass to charge ratio as well as the mass (gross and/or absolute) of some or all of the daughter fragment ions of at least one labeled analyte of the sample mixture. For each analyte present at the selected mass to charge ratio, the daughter fragment ions can be used to identify the analyte and/or analytes present at the selected mass to charge ratio. For example, this analysis can be done as previously described in the section entitled: "*Analyte Determination By Computer Assisted Database Analysis*". Thus, in some embodiments, the method further comprises determining the gross mass and relative amount of each signature ion in the second mass analysis and the gross and/or absolute mass of some or all of the daughter fragment ions in the second mass analysis. In some embodiments, the method further comprises determining the labeled analyte (and/or a precursor thereto) associated with the selected mass to charge ratio by analysis of the daughter fragment ions.

In some embodiments, one or more steps of the process can be repeated one or more times. For example, in some embodiments, ions of a selected mass to charge ratio from the first mass spectrometric analysis, different from any previously selected mass to charge ratio, can be treated to dissociative energy to thereby form ionized reporter moieties (i.e. signature ions) and daughter fragment ions of at least some of the selected ions, as previously described. A second mass analysis of the selected ions, the reporter ions and/or the daughter fragment ions, or a fraction thereof, can be performed. The gross mass and relative amount of each unique signature ion in the second mass analysis and the mass (gross or absolute) of the daughter fragment ions can also be determined. Optionally, the labeled analyte (or precursor molecule) associated with the selected mass to charge ratio can be determined by analysis of the daughter fragment ions. In this way, the information can be made available for identifying and/or quantifying one or more additional analytes from the first mass analysis.

In some embodiments, it may be useful to repeat the process (or certain steps of the method) one or more times on a different collected sub-sample where the sample mixture has been fractionated (e.g. by electrophoretic separation). By repeating the processes on one or more additional fractions of the sample, it is possible to more fully analyze the sample mixture. Consequently, the method can comprise selecting a different sub-sample and performing a first mass analysis on the sub-sample and then repeating one or more of the subsequent steps previously described.

In some embodiments, it may be useful to repeat the process one or more times by collecting one or more different sub-samples of co-migrating differentially labeled analytes from the electrophoretic separation where the sample mixture has been fractionated. By repeating the processes to thereby collect one or more additional sub-samples, it is possible to more fully analyze the sample mixture. Consequently, the method can comprise collecting one or more different sub-samples of co-migrating differentially labeled analytes from the electrophoretic separation and then repeating one or more of the subsequent previously described steps.

It is contemplated that in some embodiments, the whole process will be repeated one or more times and within each of these repeats, certain steps can also be repeated one or more times such as described above. In this way, the contents of the sample mixture can be interrogated and determined to the fullest possible extent. In some embodiments, the entire process can also be repeated on a new set of two or more samples.

As previously discussed, in some embodiments, the labeling reagents of the set of isomeric and/or isobaric labeling reagents can be support-bound. Accordingly, except for accommodating recapture of the labeled analytes from the support, the above described methods can be practiced with the support-bound reagents. This, in some embodiments, this invention pertains to practicing any of the above disclosed methods, wherein each different labeling reagent of the set is support-bound and is linked to the support through a cleavable linker such that each different sample is reacted with a support carrying a different labeling reagent of the set and wherein the method further comprises, after performing the step of labeling the sample but before performing the step of mixing the labeled samples to prepare the sample mixture: i) optionally washing each support to remove components of each sample that do not react with the reactive group of the support-bound labeling reagent; ii) cleaving the cleavable linker to thereby release the labeled analytes from each support, each differentially labeled sample comprising one or more labeled analytes wherein the labeled analytes associated with a particular sample are identifiable and/or quantifiable by the reporter moiety of unique mass linked thereto; and iii) optionally collecting the labeled analytes of each sample prior to mixing them according to step (b).

For example, the method can be practiced with a set of isotopically labeling reagents wherein each different labeling reagent of the set is represented by formula $I^{ss}$;

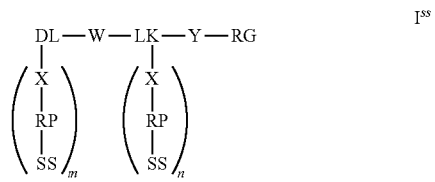

including a salt form and/or hydrate form thereof; wherein m and n are each 0 or 1 provided that m+n=1. According to the method, RG (as described in more detail above) is a reactive group comprising a nucleophile or an electrophile and said reactive group reacts with the one or more reactive analytes of the sample to thereby form the one or more labeled analytes. The reporter moiety "RP" (as described in more detail above) comprises a fixed charge or is ionizable in a mass spectrometer, wherein said reporter moiety is capable of producing a signature ion in a mass spectrometer upon fragmentation of bond X and wherein the gross mass of each reporter moiety, and its corresponding signature ion, is different for each labeling reagent of the set. The non-encoded detectable label "DL" (as described in more detail above) is a different independently detectable non-encoded detectable label for each reagent of the set, wherein each non-encoded detectable label has the same gross mass and same net charge as the other non-encoded detectable labels of the labeling reagents of the set. The linker moiety "LK" (as described in more detail above) can be linear or branched, wherein LK links (directly or indirectly) the reactive group to both the reporter moiety and the non-encoded detectable label and wherein the mass of the linker moiety of each different reagent of the set compensates for the difference in gross mass between the reporter moieties for the different labeling reagents of the set such that the aggregate gross mass of the combination of the reporter moiety and the linker moiety is the same for each labeling reagent of the set. The covalent bond X (as described in more detail above) links the reporter moiety to the linker moiety or to the non-encoded detectable label, wherein X is fragmentable by application of dissociative energy in a mass spectrometer. Y (as described in more detail above) is a covalent bond or linking group that links the reactive group to the linker moiety, wherein Y is optionally fragmentable by application of dissociative energy in a mass spectrometer, provided that if Y is a linking group its gross mass is the same for every labeling reagent of the set. W (as described in more detail above) is a covalent bond or linking group that links the non-encoded detectable label to the linker moiety, wherein W is optionally cleavable by application of light, heat and/or chemical reagent(s) and/or fragmentable by application of dissociative energy in a mass spectrometer, provided that if W is a linking group its gross mass is the same for every labeling reagent of the set. SS (as described in more detail above) is a solid support to which the reporter moiety of the labeling reagent is covalently linked through a cleavable linker.

In some embodiments, one of the labeling reagents can be represented by formula $II^{ss}$ or $III^{ss}$;

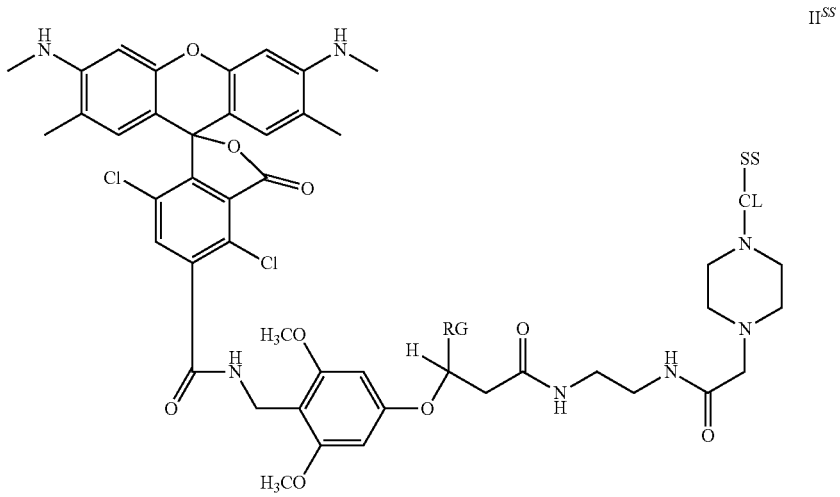

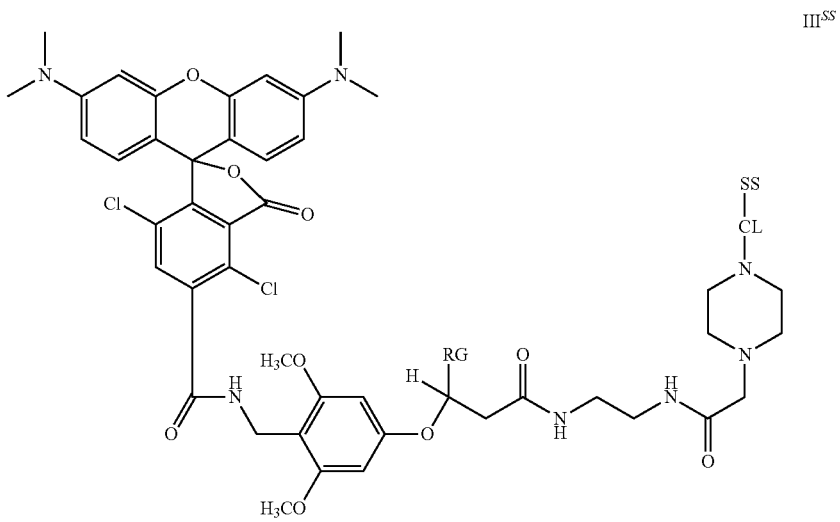

wherein RG is the reactive group, SS is the solid support and CL is the cleavable linker. In some embodiments, compounds II$^{ss}$ and III$^{ss}$ can be isotopically encoded as illustrated in FIG. 8b.

Those of ordinary skill in the art of mass spectrometry will appreciate that the first and second mass analysis described in the above disclosed methods can be performed in a tandem mass spectrometer. Instruments suitable for performing tandem mass analysis have been previously described herein. Although tandem mass spectrometers are preferred, single-stage mass spectrometers may also be used. For example, analyte fragmentation may be induced by cone-voltage fragmentation, followed by mass analysis of the resulting fragments using a single-stage quadrupole or time-of-flight mass spectrometer. In other examples, analytes may be subjected to dissociative energy levels using a laser source and the resulting fragments recorded following post-source decay in time-of-flight or tandem time-of-flight (TOF-TOF) mass spectrometers.

In some embodiments, methods of the invention can further comprise digesting each sample and/or the sample mixture with at least one enzyme to partially, or fully, degrade components of the sample and/or the sample mixture prior to performing the labeling of the analytes of the sample (Also see the above section entitled: "Sample Processing"). For example, the enzyme can be a protease (to degrade proteins and/or peptides) or a nuclease (to degrade nucleic acids). Two or more enzymes may also be used together to thereby further degrade sample components. For example, the enzyme can be a proteolytic enzyme such as trypsin, papain, pepsin, ArgC, LysC, V8 protease, AspN, pronase, chymotrypsin or a carboxypeptidase (e.g. A, B, C, etc).

In some embodiments, methods can further comprise separating the sample mixture by application of an additional separations process other than electrophoresis prior to performing the first mass analysis (Also see the above section entitled: "Separation Including Separation Of The Sample Mixture"). For example, liquid chromatography/mass spectrometry (LC/MS) can be used to effect such a sample separation prior to the mass analysis.

In some embodiments, the methods can be practiced with digestion and additional separation steps. While these steps are optional, they can be performed together, for example, when proteomic analysis is being done to thereby determine the up and down regulation of proteins in cells. In some embodiments, the steps of the methods, with or without the digestion and/or separation steps, can be repeated one or more times to thereby identify and/or quantify one or more other analytes in a sample or one or more analytes in each of the two or more samples (including samples labeled with support-bound labeling reagents). Depending of whether or not a calibration standard is present in the sample mixture or whether or not a calibration curve for the signature ion is available, the quantification of a particular analyte can be relative to the other labeled analytes, or it can be absolute.

As described previously, it is possible to determine the analyte associated with the selected ions by analysis of the mass (gross or absolute) of the daughter fragment ions. One such method of determination is described in the section entitled: "Analyte Determination By Computer Assisted Database Analysis". Once the analyte has been determined, information regarding the gross mass and relative amount of each unique reporter ion in the second mass analysis and the mass of daughter fragment ions provides the basis to determine other information about the sample mixture.

The relative amount of signature ion (reporter ion) can be determined by peak intensity in the mass spectrum. In some embodiments, the amount of each unique signature ion can be determined by analysis of the peak height or peak width (or peak area) of the reporter ion (signature ion) obtained using a mass spectrometer. Because each sample can be labeled with a different labeling reagent and each labeling reagent can comprise a unique reporter moiety that produces a unique signature ion that can be correlated with a particular differentially labeled sample used to formulate the sample mixture, determination of the different reporter ions in the second mass analysis can be used to identify the differentially labeled sample from which the signature ions of the selected analyte originated. Where multiple signature ions are found (e.g. according to the multiplex methods of the invention), the relative amount of each unique signature ion can be determined with respect to the other signature ions. Because the relative amount of each unique signature ion determined in the second mass analysis can be correlated with the relative amount of an analyte in the sample mixture, the relative amount (often expressed as concentration and/or quantity) of the analyte in each of the differentially labeled samples combined to form the sample mixture can be determined. Moreover, it is possible to relate the quantification information for an analyte to components of the original differentially labeled samples where an analyte that is determined is a by-product from another compound of interest (e.g. the analyte is a product of a degradation reaction such as where the analyte is a peptide formed by the digestion of a protein).

As discussed above, this analysis can be repeated one or more times on selected ions of a different mass to charge ratio to thereby obtain the relative amount of one or more other determined analytes in each sample combined to form the sample mixture. Moreover, as appropriate, a correction of peak intensity associated with each unique signature ion can be performed for naturally occurring, or artificially created, isotopic abundance, as previously discussed in the section entitled: "Relative and Absolute Quantification of Analytes".

For example, the analytes can be peptides in a sample or sample mixture. Analysis of the peptides in a sample, or sample mixture, can be used to determine the amount (often expressed as a concentration and/or quantity) of identifiable proteins in the sample or sample mixture wherein proteins in one or more samples can be degraded prior to the first mass analysis and wherein the amount of protein in the sample is determined based upon the identity and relative amount of the one or more peptides in each of the two or more differentially labeled samples mixed to form the sample mixture. Moreover, the information from different samples can be compared for the purpose of making determinations, such as for the comparison of the effect on the amount of the protein in cells that are incubated with differing concentrations of a substance that may affect cell growth, development, differentiation and/or death. Other, non-limiting examples may include comparison of the expressed protein components of diseased and healthy tissue or cell cultures. This may encompass comparison of expressed protein levels in cells, tissues or biological fluids following infection with an infective agent such as a bacteria or virus or other disease states such as cancer. In other examples, changes in protein concentration over time (time-course) studies may be undertaken to examine the effect of drug treatment on the expressed protein component of cells or tissues. In still other examples, the information from different samples taken over time may be used to detect and monitor the concentration of specific proteins in tissues, organs or biological fluids as a result of disease (e.g. cancer) or infection. Such experiments may include one or more control samples. In some embodiments, the experiments can be used to determine two or more of the characteristics of interest described above.

Where a calibration standard comprising a unique signature moiety linked to an analyte, having the selected mass to charge ratio, has been added to the sample mixture in a known amount (often expressed as a concentration and/or quantity) for the determined analyte, the amount of the unique signature ion associated with the calibration standard can be used to determine the absolute amount (often expressed as a concentration and/or quantity) of the analyte in each of the samples combined to form the sample mixture. This is possible because the amount of analyte associated with the unique signature ion for the calibration standard in the sample mixture is known and the relative amounts of all unique signature ions can be determined for the labeled analyte associated with the selected ions with reference to the intensity of the signature ion of the calibration standard. Because the relative amount of each unique signature ion, determined for each of the unique reporters moieties (including the reporter moiety for the calibration standard), is proportional to the amount of the analyte associated with each differentially labeled sample combined to form the sample mixture, the absolute amount (often expressed as a concentration and/or quantity) of the analyte in each of the samples can be determined with reference to the amount of each different signature ion of unique mass based upon a ratio calculated with respect to the formulation used to produce the sample mixture. As appropriate, a correction of peak intensity associated with each of the unique signature ions can be performed for naturally occurring, or artificially created, isotopic abundance. Such an analysis method can be particularly useful for proteomic analysis of multiplex samples of a complex nature, especially where a preliminary separation of the labeled analytes (e.g. liquid chromatography or electrophoretic separation) precedes the first mass analysis.

For example, if a sample mixture comprises 100 fmol/mL of a calibration standard and the relative intensity of the unique signature ion associated with the calibration standard was 1 while the relative intensity of a first other unique signature ion associated with a first sample was one-half and the relative intensity of a second other unique signature ion associated with a second sample was 2, the amount of the analyte in the first differentially labeled sample mixed to form the sample mixture (assuming equal amounts of sample 1 and sample 2 are mixed to form the sample mixture) is 50 fmol/mL (0.5×100 fmol/mL) and the amount of the analyte in the second differentially labeled sample mixed to form the sample mixture is 200 fmol/mL (2×100 fmol/mL). Moreover, if, for example, the analyte is a peptide associated with a particular protein, it can be inferred that the amount of the protein in sample 1 is 50 fmol/mL and the amount of the protein in sample 2 is 200 fmol/mL. Thus, the presence of the calibration standard permits absolute quantification of the labeled analytes (and in some cases their precursors) in each differentially labeled sample mixed to form the sample mixture.

Because the analyte can be a precursor molecule, in some embodiments, the analytes can be peptides and the identity and absolute amount of one or more proteins in each of the two or more differentially labeled samples mixed to form the sample mixture can be determined based upon the identity and absolute amount of the one or more peptides in each of the two or more differentially labeled samples mixed to form the sample mixture.

As previously discussed, this analysis can be repeated one or more times on selected ions of a different mass to charge ratio to thereby obtain the absolute amount of one or more other determined analytes in each sample combined to form the sample mixture. Moreover, as appropriate, a correction of peak intensity associated with each unique reporter ion can be performed for naturally occurring, or artificially created, isotopic abundance, as previously discussed.

In some embodiments, methods described herein can be practiced with support-bound labeling reagents, wherein each different labeling reagent of the set is support-bound and is cleavable linked to the support by the reporter moiety through a cleavable linker such that each different sample can be reacted with a support carrying a different labeling reagent of the set. Exemplary supports have been discussed above in the section entitled: "Compositions" (Also see FIG. 6). According to the method, the support can be optionally washed to remove components of the sample that do not react with the reactive group of the labeling reagent after the analyte has been permitted to react with the support-bound labeling reagent but before the samples are mixed. Once the analyte has been permitted to react with the labeling reagent to thereby form the labeled analyte and the washing step is optionally performed, the labeled analyte(s) can be released from the support by treating the support under conditions whereby the cleavable linker is cleaved. Once cleaved, each of the two or more differentially labeled samples can be optionally collected, each sample comprising one or more labeled analytes wherein the labeled analytes associated with a particular sample are identifiable and/or quantifiable by the unique reporter moiety linked thereto. Whether or not they are collected individually, the products of cleavage can be mixed to form a sample mixture.

IV. Mixtures

In some embodiments, this invention pertains to mixtures (i.e. sample mixtures). For example, the mixtures can comprise labeled analytes comprising isotopically encoded isomeric and/or isobaric labels. Exemplary mixtures of labeled analytes and methods for their preparation and/or analysis have been described in the section entitled: "*Methods for Labeling and Analysis*", set forth above.

The mixture can be formed by mixing all, or a part, of the product of two or more labeling reactions wherein each sample is labeled with a different labeling reagent of a set of labeling reagents wherein each labeling reagent comprises a reporter moiety of unique (gross) mass as well as a non-encoded detectable label. The unique reporter moiety of each different labeling reagent can identify from which labeling reaction each of the two or more labeled analytes is derived (i.e. originated). The non-encoded detectable label can be used to locate labeled analytes during an electrophoretic separation. Characteristics of the labeling reagents and labeled analytes associated with these methods have been previously discussed.

One or more of the analytes of the mixture can be peptides. One or more of the analytes of the mixture can be proteins. One or more of the analytes of the mixture can be peptides and proteins. One or more of the analytes of the mixture can be nucleic acid molecules. One or more of the analytes of the mixture can be carbohydrates. One or more of the analytes of the mixture can be lipids. One or more of the analytes of the mixture can be steroids. One or more of the analytes of the mixture can be vitamins. One or more of the analytes of the mixture can be prostaglandins. One or more of the analytes of the mixture can be amino acids. One or more of the analytes of the mixture can be small molecules having a mass of less than 1500 daltons. In some cases the analytes can be mixtures of various analyte types. For example, the analytes of the mixture comprise lipids and steroids; or 2) proteins, peptides, amino acids, lipids, steroids and carbohydrates). Mixtures can comprise any type of differentially labeled analytes labeled with the novel labeling reagents disclosed herein including mixtures comprising two or more different analyte types.

For example, the mixtures can comprise at least two differentially labeled analytes wherein said mixture is formed by mixing the product of a labeling reaction of at least two different samples each sample being labeled with a different labeling reagent from a set of isotopically encoded isomeric and/or isobaric labeling reagents, wherein each differentially labeled analyte of the mixture is represented by formula $I^4$:

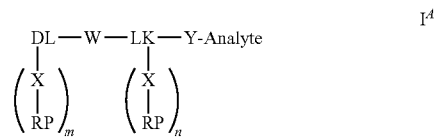

including a salt form and/or hydrate form thereof, wherein m and n are each 0 or 1 provided that m+n=1; The reporter moiety "RP" (as described in more detail above) comprises a fixed charge or is ionizable in a mass spectrometer, wherein said reporter moiety is capable of producing a signature ion in a mass spectrometer upon fragmentation of bond X and wherein the gross mass of each reporter moiety, and its corresponding signature ion, is different for each different sample depending on which labeling reagent of the set was used to label the sample. The non-encoded detectable label "DL" (as described in more detail above) is different for each different labeling reagent of the set and each different non-encoded detectable label is independently detectable of the others in the set and wherein each different non-encoded detectable label has the same gross mass and same net charge as the other non-encoded detectable labels of the other labeling reagents of the set. The linker moiety "LK" (as described in more detail above) can be linear or branched, wherein LK links (directly or indirectly) the analyte to both the reporter moiety and the non-encoded detectable label and wherein the mass of the linker moiety of each different labeling reagent of the set compensates for the difference in gross mass between the reporter moieties for the different labeling reagents of the set such that the aggregate gross mass of the combination of the reporter moiety and the linker moiety is the same for each labeling reagent of the set. X (as described in more detail above) is a covalent bond that links the reporter moiety to the linker moiety or to the non-encoded detectable label and wherein bond X is fragmentable by application of dissociative energy in a mass spectrometer. Y (as described in more detail above) is a covalent bond or linking group that links the analyte to the linker moiety and wherein Y is optionally fragmentable by application of dissociative energy in a mass spectrometer, provided that if Y is a linking group its gross mass is the same for every labeling reagent of the set. W (as described in more detail above) is a covalent bond or linking group that links the non-encoded detectable label to the linker moiety and wherein W is optionally cleavable by application of light, heat and/or chemical reagent(s) and/or fragmentable by application of dissociative energy in a mass spectrometer, provided that if W is a linking group its gross mass is the same for every labeling reagent of the set. Certain fragmentation properties of labeled analyte $I^4$ are illustrated in FIG. 3a.

For example, the mixture can comprise at least one labeled analyte represented by formula $II^4$ or $III^4$;

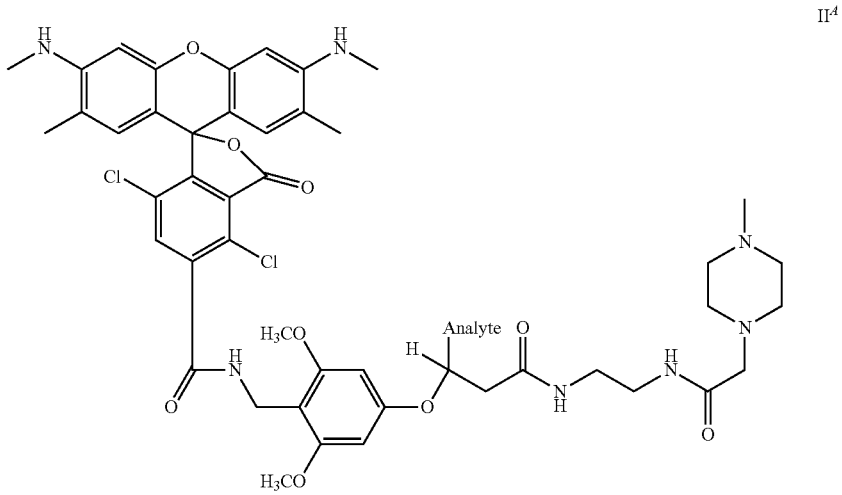

$II^4$

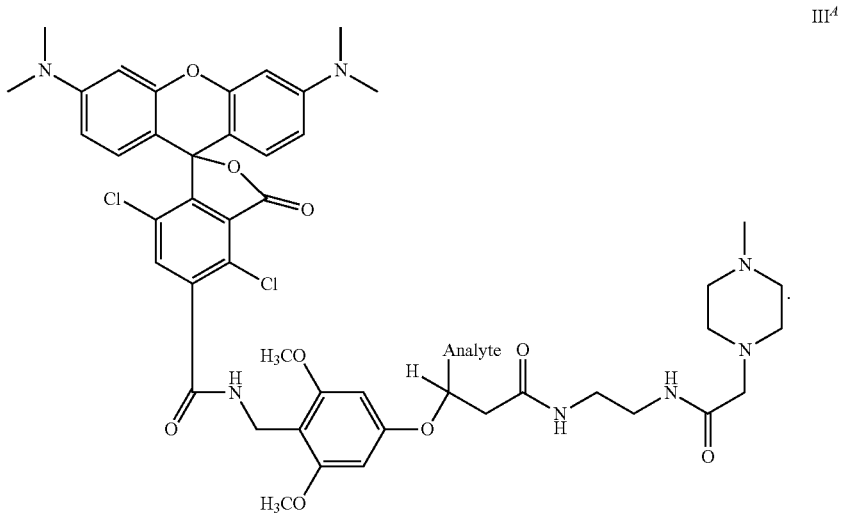

$III^4$

Figure 3B:
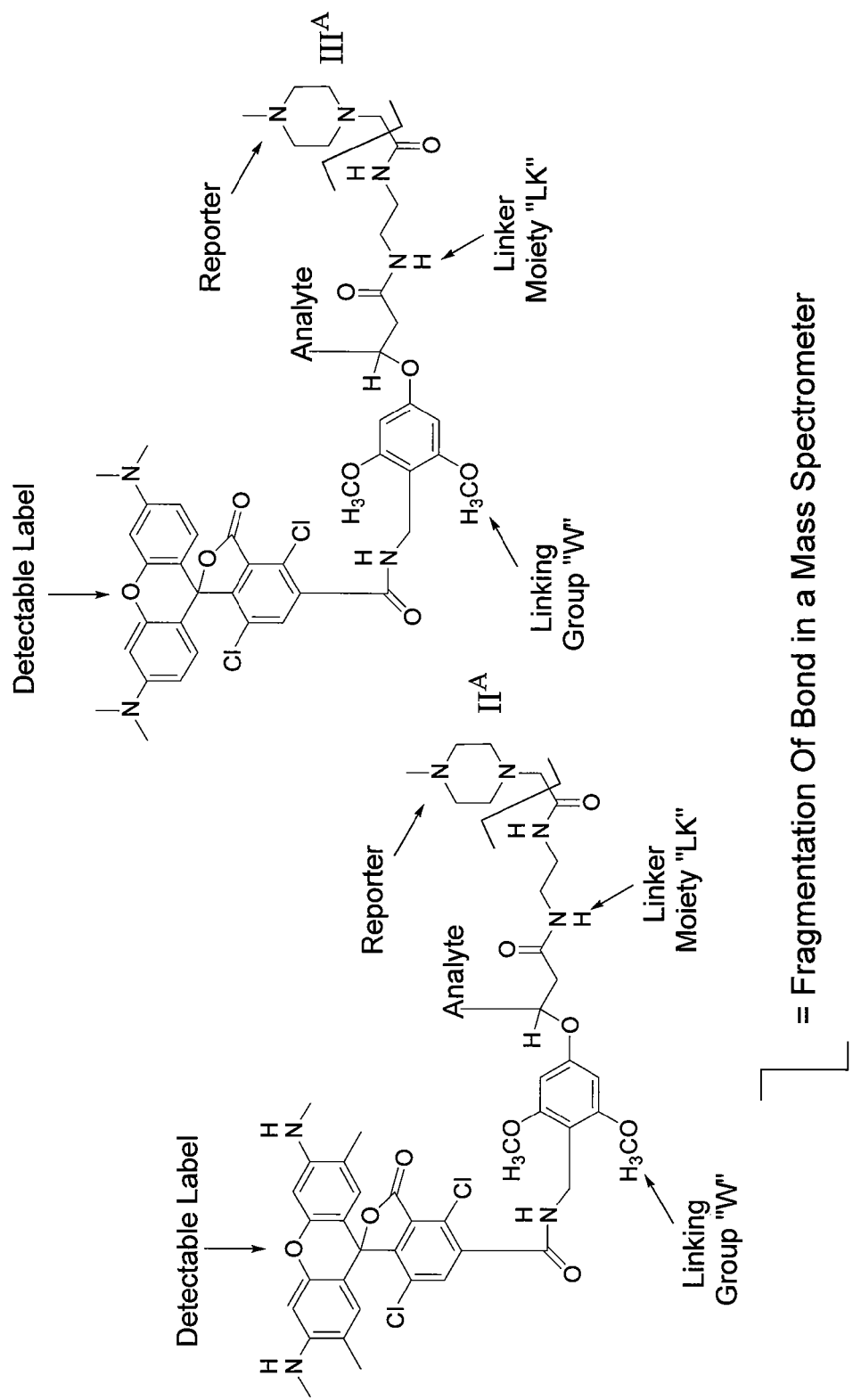
FIG. 3b is an illustration of the certain fragmentation characteristics of various labeled analytes.
Figure 3C:
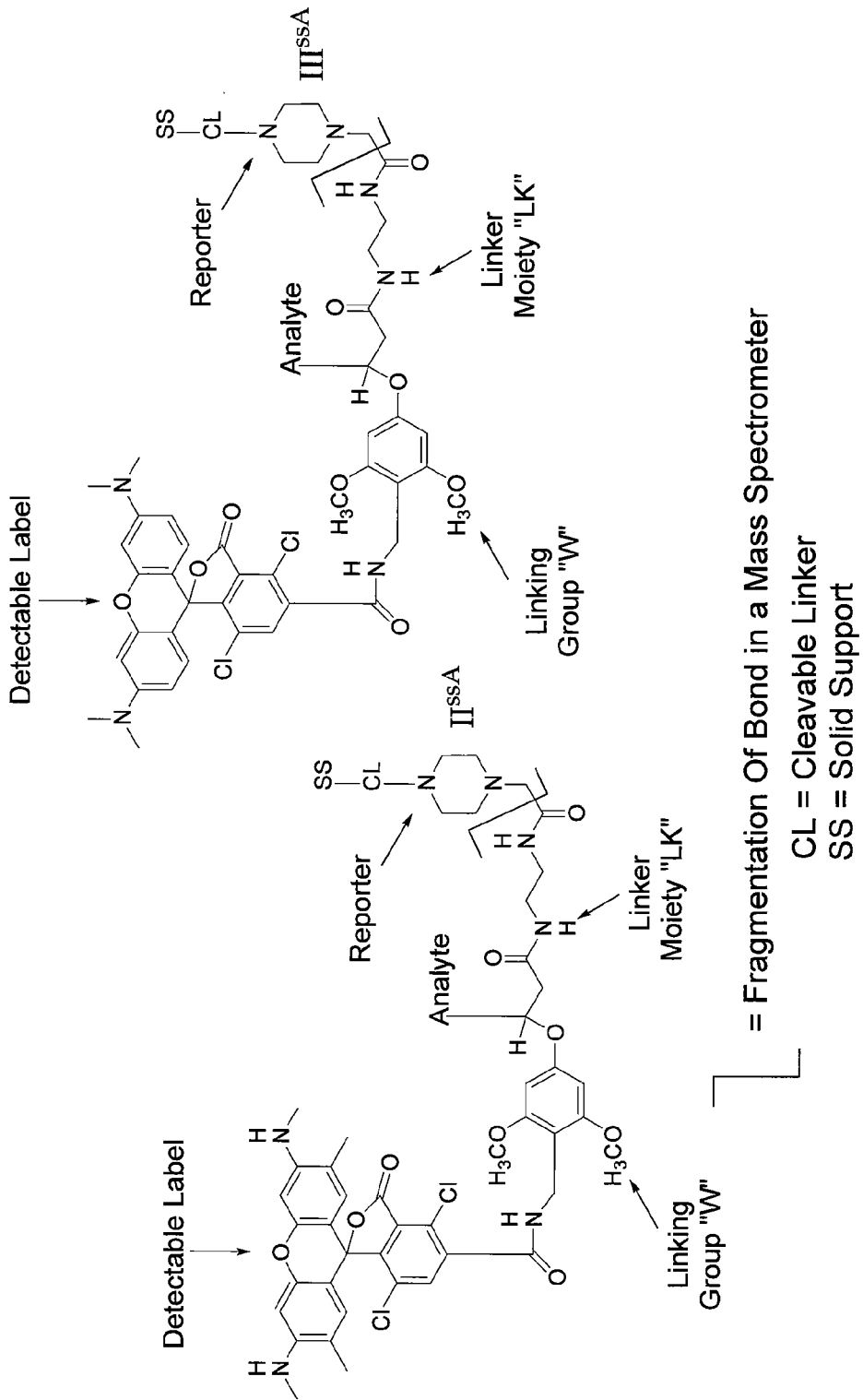
FIG. 3c is an illustration of the certain fragmentation characteristics of various support-bound labeled analytes.

The elements and certain fragmentation properties of labeled analytes II$^A$ and III$^A$ are illustrated in FIG. 3b.

In some embodiments, the mixture is prepared by using support-bound labeling reagents and the labeled analytes are cleaved from the support to thereby form the mixture. Thus, in some embodiments, this invention pertains to a mixture comprising at least two differentially labeled analytes wherein said mixture is formed by mixing the product of a labeling reaction of at least two different samples each sample being labeled with a different labeling reagent from a set of isotopically encoded isomeric and/or isobaric labeling reagents, wherein each differentially labeled analyte of the mixture is represented by formula I$^{ssAx}$;

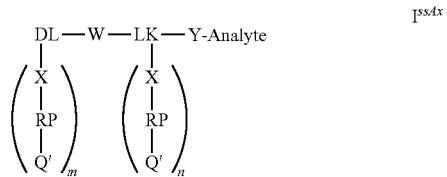

including a salt form and/or hydrate form thereof; wherein m and n are each 0 or 1 provided that m+n=1. The reporter moiety "RP" (as described in more detail above) comprises a fixed charge or is ionizable in a mass spectrometer, wherein said reporter moiety is capable of producing a signature ion in a mass spectrometer upon fragmentation of bond X and wherein the gross mass of each reporter moiety, and its corresponding signature ion, is different for each different sample depending on which labeling reagent of the set was used to label the sample. The non-encoded detectable label "DL" (as described in more detail above) is different for each different labeling reagent of the set, wherein each different non-encoded detectable label is independently detectable of the others in the set and wherein each different non-encoded detectable label has the same gross mass and same net charge as the other non-encoded detectable labels of the other labeling reagents of the set. The linker moiety "LK" (as described in more detail above) can be linear or branched, wherein LK links (directly or indirectly) the analyte to both the reporter moiety and the non-encoded detectable label and wherein the mass of the linker moiety of each different labeling reagent of the set compensates for the difference in gross mass between the reporter moieties for the different labeling reagents of the set such that the aggregate gross mass of the combination of the reporter moiety and the linker moiety is the same for each labeling reagent of the set. X (as described in more detail above) is a covalent bond that links the reporter moiety to the linker moiety or to the non-encoded detectable label and wherein bond X is fragmentable by application of dissociative energy in a mass spectrometer. Y (as described in more detail above) is a covalent bond or linking group that links the analyte to the linker moiety and wherein Y is optionally fragmentable by application of dissociative energy in a mass spectrometer, provided that if Y is a linking group its gross mass is the same for every labeling reagent of the set. W (as described in more detail above) is a covalent bond or linking group that links the non-encoded detectable label to the linker moiety and wherein W is optionally cleavable by application of light, heat, chemical reagent(s) and/or fragmentable by application of dissociative energy in a mass spectrometer, provided that if W is a linking group its gross mass is the same for every labeling reagent of the set. Q' is a functional group formed by cleavage of the differentially labeled analyte from a solid support. For example Q' can be an alkyl amine group, an alkyl hydroxyl group or an alkyl thiol group.

For example, the mixture can comprise at least one labeled analyte represented by formula II$^{ssAx}$ or III$^{ssAx}$;

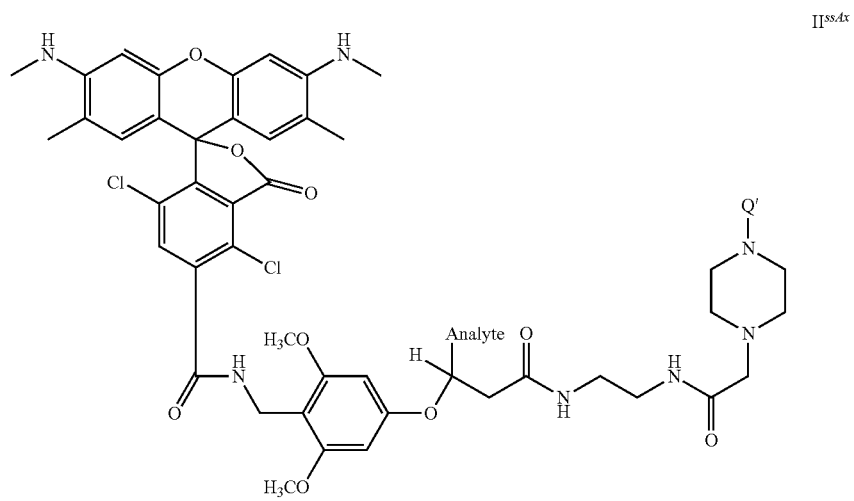

Figure 3D:
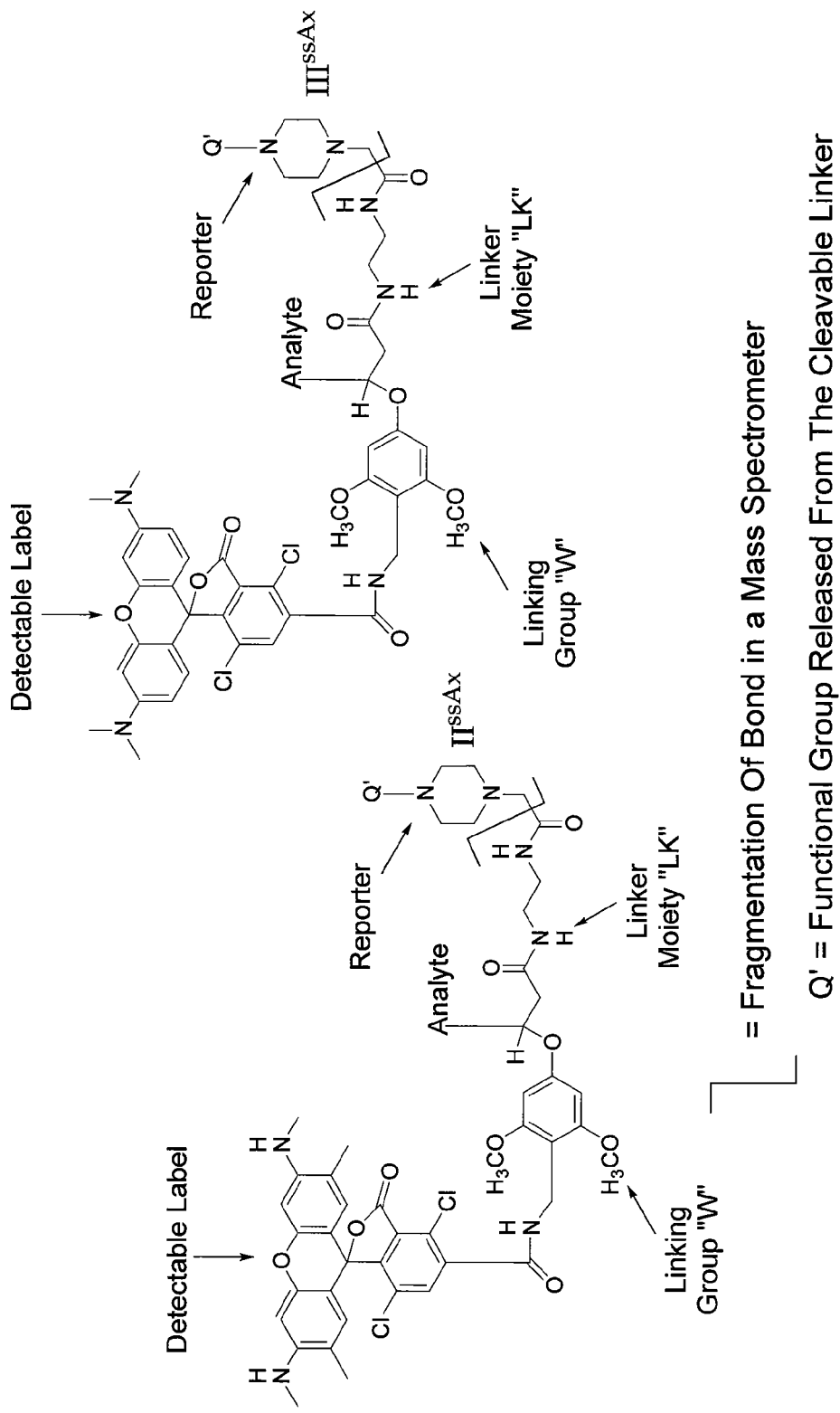
FIG. 3d is an illustration of the certain fragmentation characteristics of various labeled analytes that have been released from a solid support.

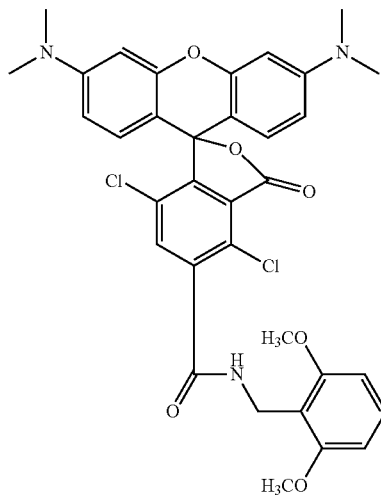
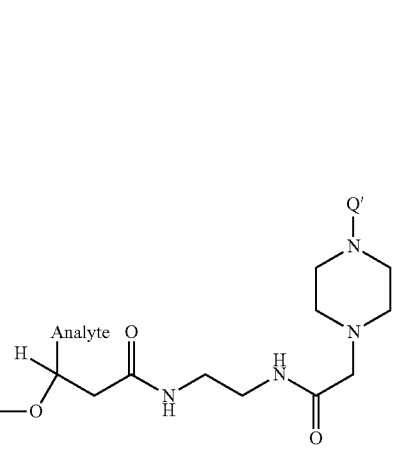

wherein Q' is a functional group formed by cleavage of the differentially labeled analyte from a solid support. The elements and certain fragmentation properties of labeled analytes $II^{ssAx}$ and $III^{ssAx}$ are illustrated in FIG. 3d.

V. Kits

In some embodiments, this invention pertains to kits. The kits can comprise one or more labeling reagents as described herein as well as one or more other reagents, containers, enzymes, buffers and/or instructions. For example, the reagents of the kit can be selected to perform an assay for quantifying one or more analytes in two or more different samples. The kits can comprise a set of two or more labeling reagents and one or more other reagents, containers, enzymes, buffers and/or instructions. Two or more of the labeling reagents of a kit can be isomeric and/or isobaric. The labeling reagents can be isotopically encoded.

The labeling reagents of the kit can be any labeling reagent described herein. For example, the one or more labeling reagents of the kits can be compounds (including sets of compounds) of the formula: I, II, III, $I^{ss}$, $II^{ss}$, and/or $III^{ss}$, as previously disclosed herein, including isotopically encoded versions thereof.

In some embodiments, the kit can comprise a labeled analyte of formula: $I^A$, $II^A$, $III^A$, $I^{ssAx}$, $II^{ssAx}$, and/or $III^{ssAx}$, as previously disclosed herein, including isotopically encoded versions thereof. Other properties of the labeling reagents of the kits have been disclosed. In some embodiments, at least one additional reagent of the kit can be a labeled calibration standard comprising a reporter moiety. In some embodiments, the reporter can have a unique mass as compared with any of the compound (i.e. labeling reagents) in the kit. The kits can, for example, be useful for the multiplex analysis of one or more analytes in the same sample, or in two or more different samples.

EXAMPLES

Aspects of the present teachings can be further understood in light of the following examples, which should not be construed as limiting the scope of the present teachings in any way.

Example 1

Proposed Synthetic Route to Labeling Reagents

Figure 9A:
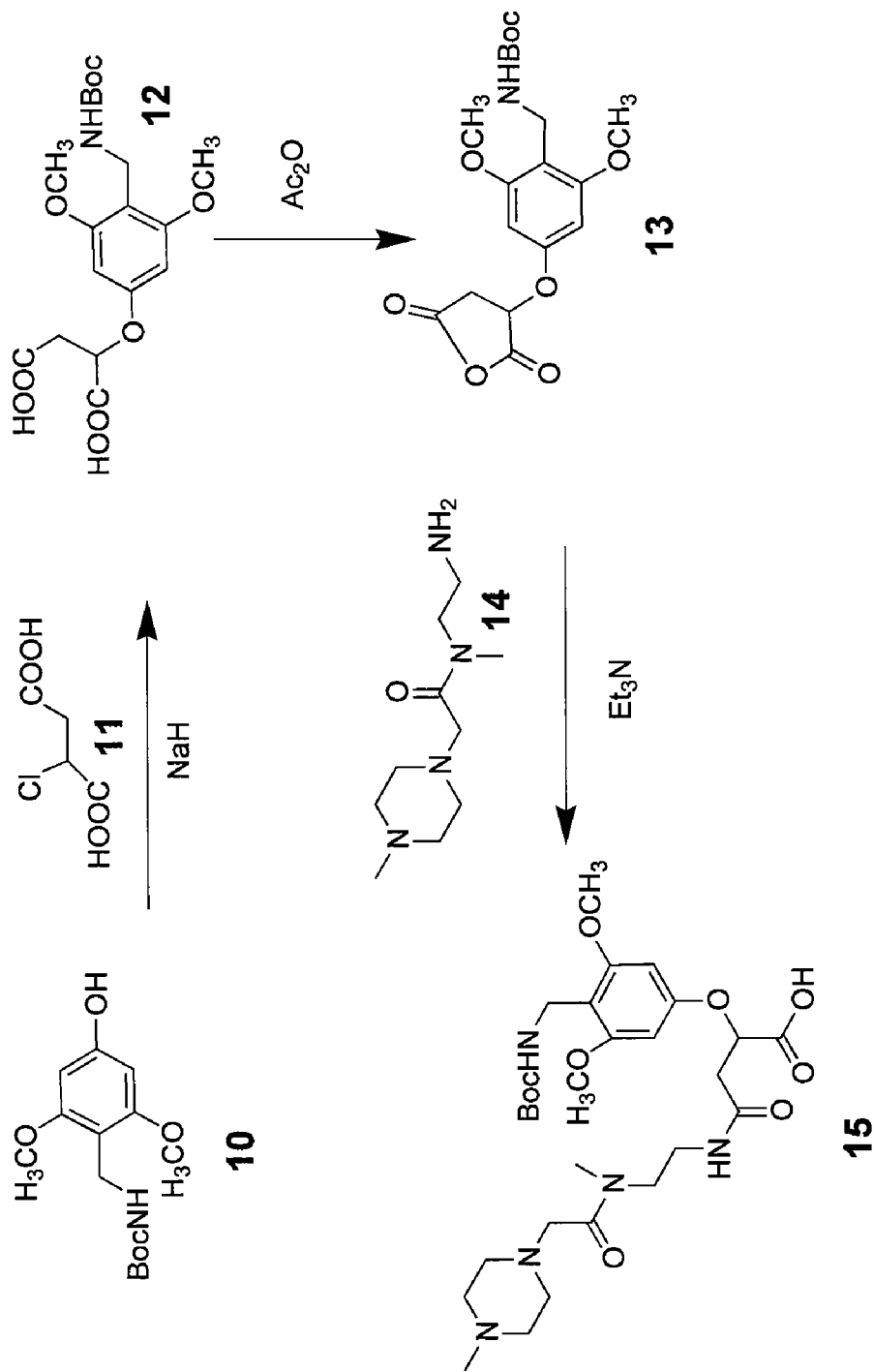
FIG. 9a illustrates part of a prophetic synthetic route to a representative labeling reagent.
Figure 9B:
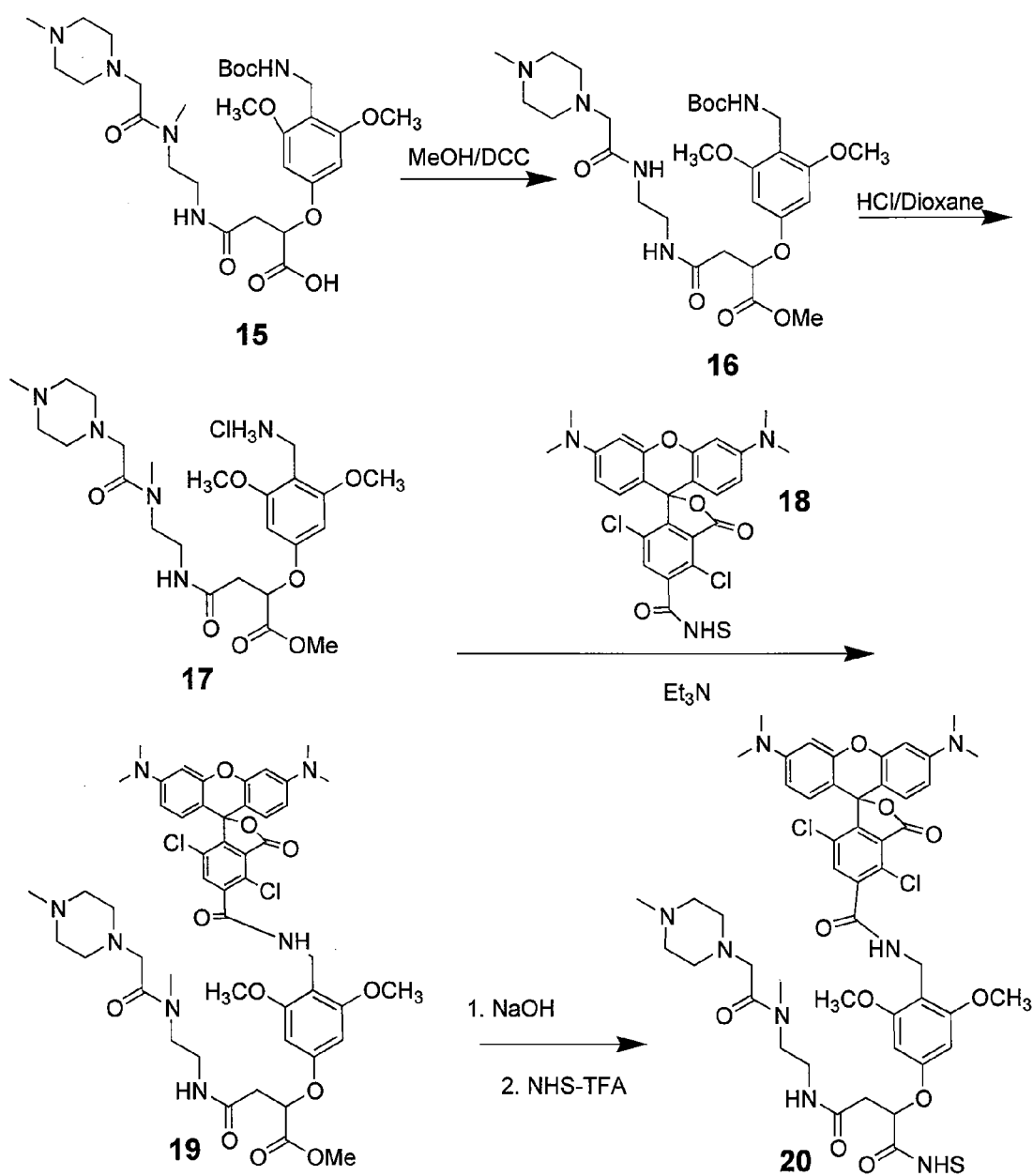
FIG. 9b illustrates the remaining part (with respect to FIG. 9a) of a prophetic synthetic route to a representative labeling reagent.

With reference to FIGS. 9a and 9b, a proposed synthetic route to exemplary labeling reagent III is presented. It is to be understood that the same method can be used to prepare exemplary labeling reagent II by simple substitution of the appropriate fluorescent dye. It also is to be understood that the compositions can be prepared with isotopically enriched sites by substitution of appropriately encoded starting materials.

With reference to FIG. 9a, compound 10 is reacted with compound 11 in the presence of sodium hydride (NaH) to thereby produce the product compound 12. Compound 12 is treated with acetic anhydride ($Ac_2O$) to there by form Compound 13. Compound 13 is treated with compound 14 (including isotopically encoded versions thereof as appropriate—See for example, Example 2, below) to thereby produce compound 15.

With reference to FIG. 9b, compound 15 is then treated with methanol (MeOH) and dicyclohexylcarbodiimide (DCC) to thereby produce compound 16. Compound 16 is then treated with hydrochloric acid (HCl) in dioxane to thereby produce compound 17. Compound 17 is then treated under basic conditions with a non-nucleophilic base, such as triethylamine ($Et_3N$), and an activated (e.g. activated as an N-hydroxysuccinimide ester (NHS ester)) non-encoded detectable label, such as compound 18, to thereby produce compound 19. Compound 18 is a one possible non-encoded detectable label and this label is represented in compounds of formula III, illustrated herein. An activated form of a non-encoded detectable label, such as that represented in compounds of formula II, could also be used to form a companion label of a set of isomeric and/or isobaric labeling reagents. Compound 19 is then treated with a strong base, such as sodium hydroxide (NaOH) to saponify the methyl ester and the resulting carboxylic acid is converted to an N-hydroxysuccinimidyl ester by treatment with N-hydroxysuccinimidyl-trifluoroacetate (NHS-TFA), which is a reagent commonly known to be suitable for converting carboxylic acid groups to N-hydroxysuccinimidyl esters (see FIG. 7), to thereby produce labeling reagent 20.

Example 2

Proposed Synthetic Route to Encoded Reporter Molecules (i) Synthesis of BocNH$^{13}$CH$_2$$^{13}$CH$_2$OH (31)

Figure 10A:
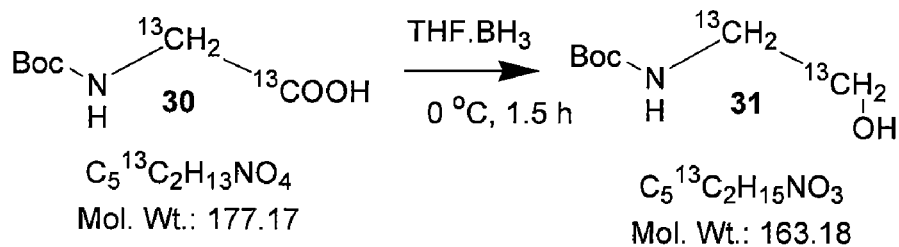
FIGS. 10a to 10d illustrate various steps for the synthesis of an encoded N-Fmoc,N'-methyl-ethylene diamine.

With reference to FIG. 10a, BocNH$^{13}$CH$_2$$^{13}$COOH (30, P/N: Aldrich 604992; 10 g, 56.44 mmol) was transferred to a 500 mL two-neck round bottom flask equipped with septa, magnetic stir bar and argon input line. After flushing the system with argon, dry tetrahydrofuran (THF, P/N: Aldrich, 186562; 100 mL) was transferred via cannula using pressure difference and stirred at room temperature until a clear solution was obtained. The reaction mixture then cooled to 0° C. and a solution of boran-THF complex (BH$_3$.THF, P/N: Aldrich 176192, 1 M, 197 mL) was added to the reaction mixture, via cannula, over 10 min period. The reaction then continued for another 90 minutes (min) at 0° C.

A small aliquot of the reaction mixture was quenched with methanol (MeOH) and analyzed by thin layer chromatography (TLC), which showed complete consumption of starting material 30 and formation of the product 31 ($R_f$30=0.00, $R_f$31=0.20; 1:1 hexanes-ethyl acetate (EtOAc); TLC developed by heating with 3% (w/v) ninhydrin solution in ethanol (EtOH)).

The reaction was quenched (at 0° C.) by slow addition of MeOH (100 mL, added over 20 min). Volatiles were removed under reduced pressure. The oil so obtained was coevaporated from additional MeOH (50 mL) and purified by column chromatography (two runs; 120 g Si$_2$ column Isco.; 85 mL/min, 0-10 min 40% EtOAc in hexanes, 10-25 min 90% EtOA hexanes. 18 mL-fractions collected; fractions 39-55 had pure product) to give BocNH$^{13}$CH$_2$$^{13}$CH$_2$OH (31) as colorless oil (7.40 g, 81%).

(ii) Synthesis of BocNHCH$_2$CH$_2$OMs (32)

Figure 10B:
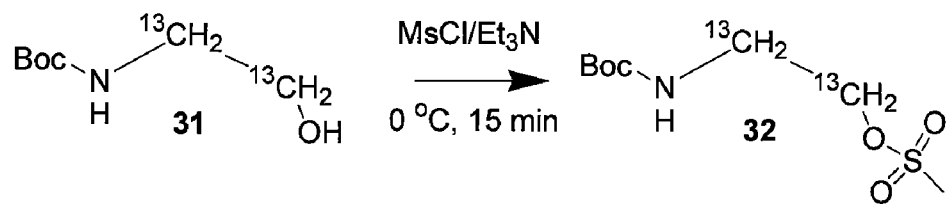

With reference to FIG. 10b, to an ice cold solution of 31 (1.15 g, 7.13 mmol), Et$_3$N (2.5 mL, 17.82 mmol) in dichloromethane (DCM, 100 mL) was added methanesulfonyl chloride (MsCl, P/N: Fluka 64260, 0.664 mL, 8.55 mmol) over 1 min while stirring. After another 15 min at 0° C. the reaction mixture was analyzed by TLC and showed formation of a new product ($R_f$31=0.20, $R_f$32=0.42; 1:1 hexanes-EtOAc; TLC developed by heating with 3% (w/v) ninhydrin solution in EtOH).

DCM evaporated and the yellow solid was dissolved in EtOAc (300 mL). The EtOAc layer was washed with HCl (1 M, 100 mL), followed by brine (50 mL×2), dried over Na$_2$SO$_4$ and concentrated to give yellow oil, which was used in the next reaction without purification.

(iii) Synthesis of BocNHCH$_2$CH$_2$NHMe (33)

Figure 10C:
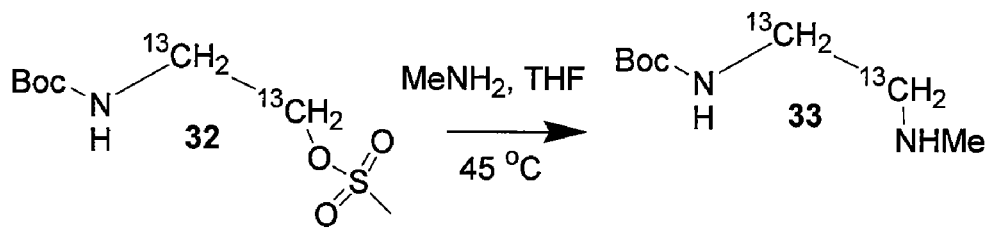

With reference to FIG. 10c, BocNHCH$_2$CH$_2$OMs (32) (1.42 g, 5.94 mmol) was transferred to a Chem-Glass pressure vessel using minimum amount of THF to which 60 mL of methylamine (MeNH$_2$, P/N: Aldrich 395056, 2.0 M in THF, 120 mmol) solution was added, capped and heated (while stirring) at 40-45° C. for 3 h, then at RT for overnight (use safety shield). TLC analysis (1:1 EtOAc-hexanes) showed complete consumption of 32 and formation of a new product ($R_f$33=0.38; 1:1 DCM-MeOH+1% (v/v) Et$_3$N; TLC plate was heated first for 5 min to remove Et$_3$N then developed by heating with 3% (w/v) ninhydrin solution in EtOH). Reaction mixture then concentrated to an oil and purified by column chromatography (40 g SiO$_2$ column Isco.; 40 mL/min, Column equilibrated with EtOAc, eluted with 1:1 MeOH-DCM+1% Et$_3$N (v/v). 18 mL-fractions collected; fractions 13-19 had pure product) to give BocNH$^{13}$CH$_2$$^{13}$CH$_2$NHMe 33 as colorless oil (0.79 g, 76%).). ES-MS (Direct infusion in MeOH) Calculated MH$^+$ [$^{13}$C$_2$C$_6$H$_{18}$N$_2$O$_2$+H]$^+$=177.14, observed MH$^+$=177.14.

(iv) Synthesis of NH$_2$CH$_2$CH$_2$NH(Me)Fmoc (34)

Figure 10D:
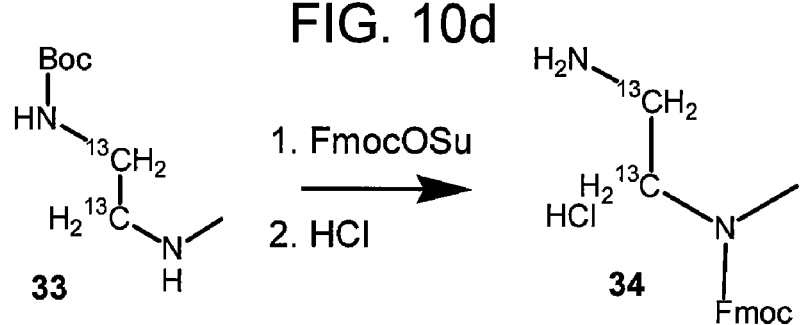

With reference to FIG. 10d, to a well stirred solution of BocNH$^{13}$CH$_2$$^{13}$CH$_2$NHMe (33, 1.78 g, 10.2 mmol) in acetone (125 mL) is added a solution of Fmoc-OSu (P/N: Advance ChemTech RC8015, 3.46 g, 10.2 mmol in 125 mL acetone). The mixture is stirred for 10 min at ambient temperature. At this point NaHCO$_3$ (saturated, 25 mL) solution is added to the reaction mixture, to adjust the pH to 8-9, and stirred vigorously for another 30 min (biphasic reaction). After evaporation of acetone, the product is partitioned between EtOAc (500 mL) and dilute (aq) hydrochloric acid (HCl, 30 mL, 1 M)+30 mL brine. The EtOAc layer is then further washed with dilute HCl (30 mL, 1 M)+30 mL brine, followed by a mixture of NaHCO$_3$ (10 mL)+brine (60 mL) and brine (50 mL×2), dried over Na$_2$SO$_4$ and concentrated to give a thick colorless oil.

The oil is then dissolved in DCM (50 mL), HCl solution in dioxane (4 M, 50 mL) is added and the reaction mixture is stirred for 30 min at ambient temperature. Volatiles are removed under reduced pressure to give a white dry solid, which is washed with 7:3 EtOAc-hexanes to give NH$_2$$^{13}$CH$_2$$^{13}$CH$_2$N(Fmoc)Me 34 as a solid.

(v) Synthesis of the a Partial Encoded Reporter/Linker Moiety (35)

Figure 11:
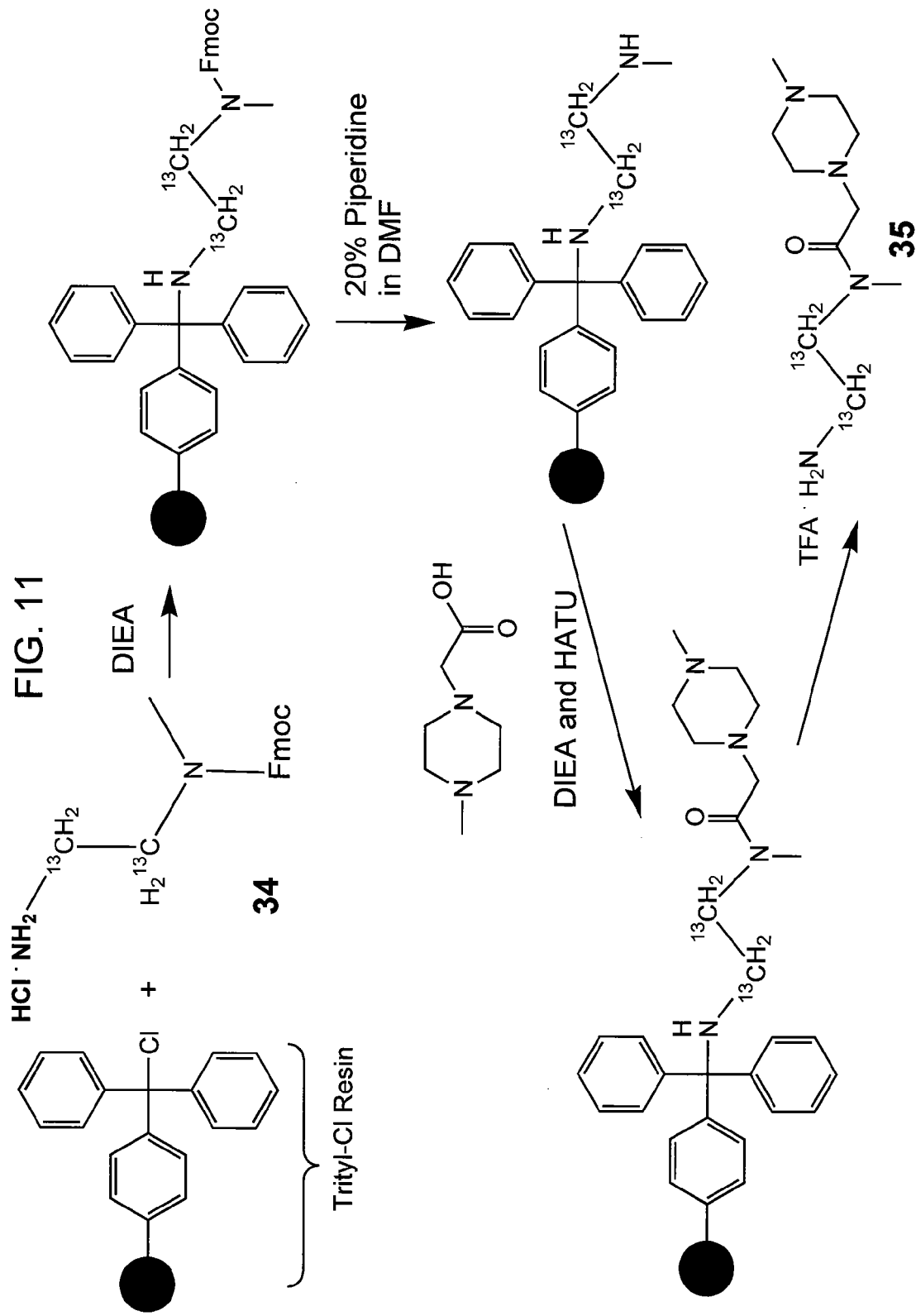
FIG. 11 illustrates the synthesis of a part of an encoded reporter/linker moiety.

With reference to FIG. 11, to a solution of 34 (3 eqv) and N,N'-diisopropylethylamine (DIEA, 6 eqv) in DCM, trityl-Cl resin (Advance ChemTech, P/N SC5028, 1 eqv) is added as a solid and mixed for 30 min. The resin is then filtered and washed with DMF. The resin is then treated with a 20% solution of piperidine in N,N'-dimethylformamide (DMF) for 5 min, and washed with DMF.

To a solution of N-methyl piperazine acetic acid (Chess GmbH, P/N 2022, 3 eqv) and O-(7-azabenzotriazol-1-yl)-N, N,N',N'-tetramethyluronium hexafluorophosphate HATU (3 eqv) in N-Methyl-2-pyrrolidinone (NMP), is added DIEA (9 eqv). This is mixed for 1 min and the added to the resin. After 30 min coupling, the resin is washed with NMP followed by acetonitrile.

Product (35) is cleaved from the resin using 15% TFA in DCM to give the compound as a TFA salt.

Figure 12:
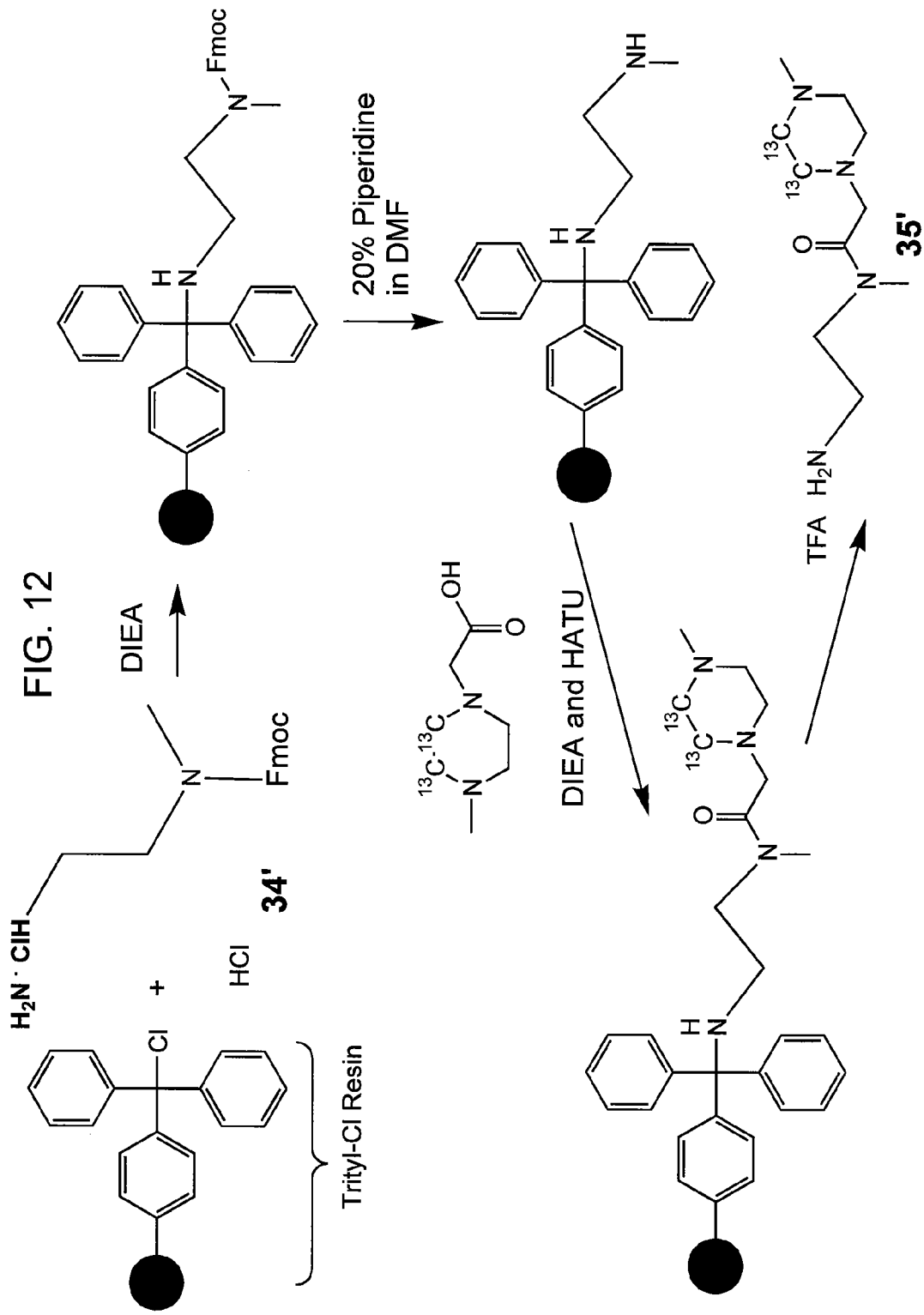
FIG. 12 illustrates the synthesis of a part of an encoded reporter/linker moiety.

It is to be understood encoded N-methyl piperazine acetic acid (See for Example US Published Patent Applications US 2005-0148774 A1 and US 2005-01448773 A1 for exemplary syntheses of encoded N-methyl piperazine acetic acid) and non-encoded $NH_2CH_2CH_2N(Fmoc)Me$ 34' (FIG. 12) can be substituted in the reaction synthesis to thereby produce a corresponding version of compound 35 (identified as 35' in FIG. 12), wherein the reporter comprises the isotopically enriched sites (See for example, the alternative synthesis illustrated in FIG. 12). By judicious selection of starting materials, essentially any desired encoded version of compound 35 can be prepared using the method(s) illustrated.

In some embodiments, the encoded N-methyl piperazine acetic acid moieties can be selected from compounds 36 or 37 represented by formulas:

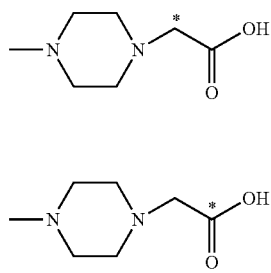

36

37 wherein the * indicates substitution of a $^{13}C$ for a $^{12}C$.

Example 3

Alternative Proposed Synthetic Route to Labeling Reagents

Figure 13A:
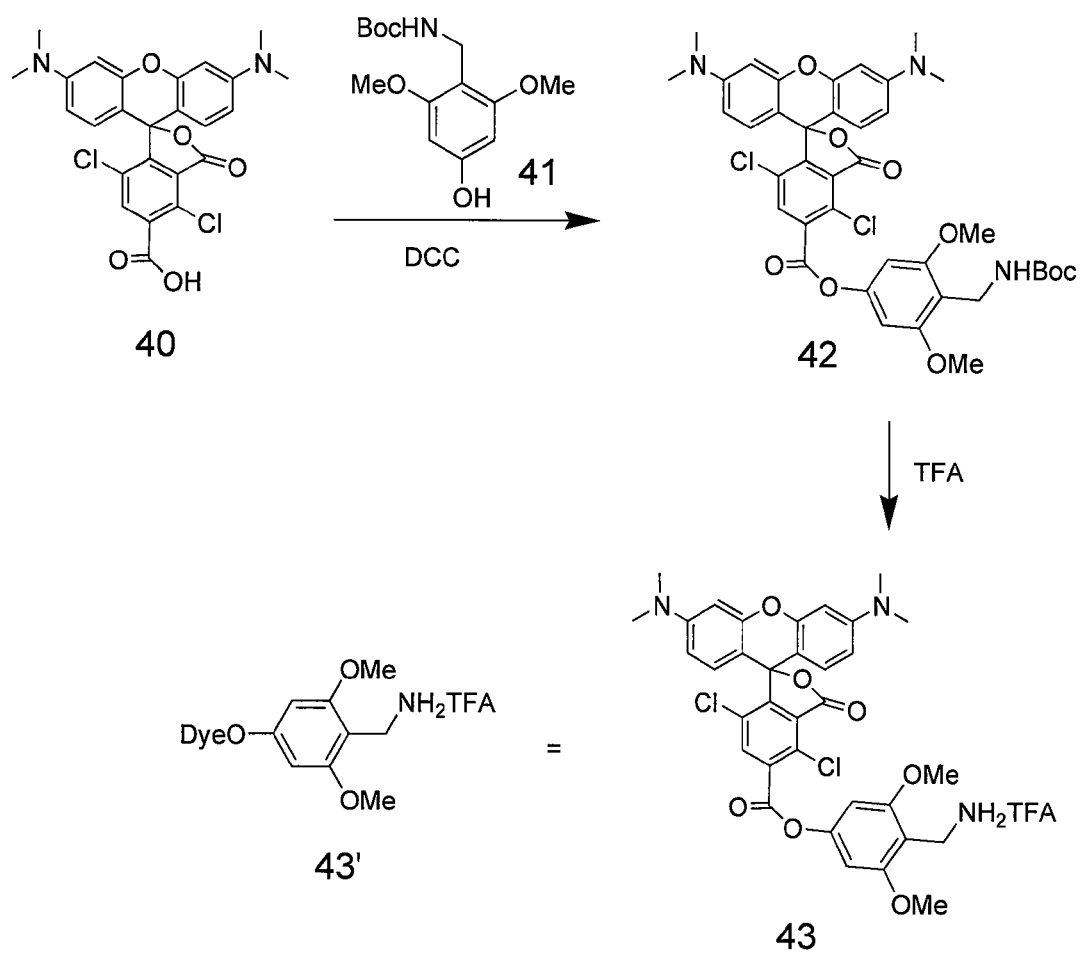
FIG. 13a illustrates part of a prophetic synthetic route to a representative labeling reagent.
Figure 13B:
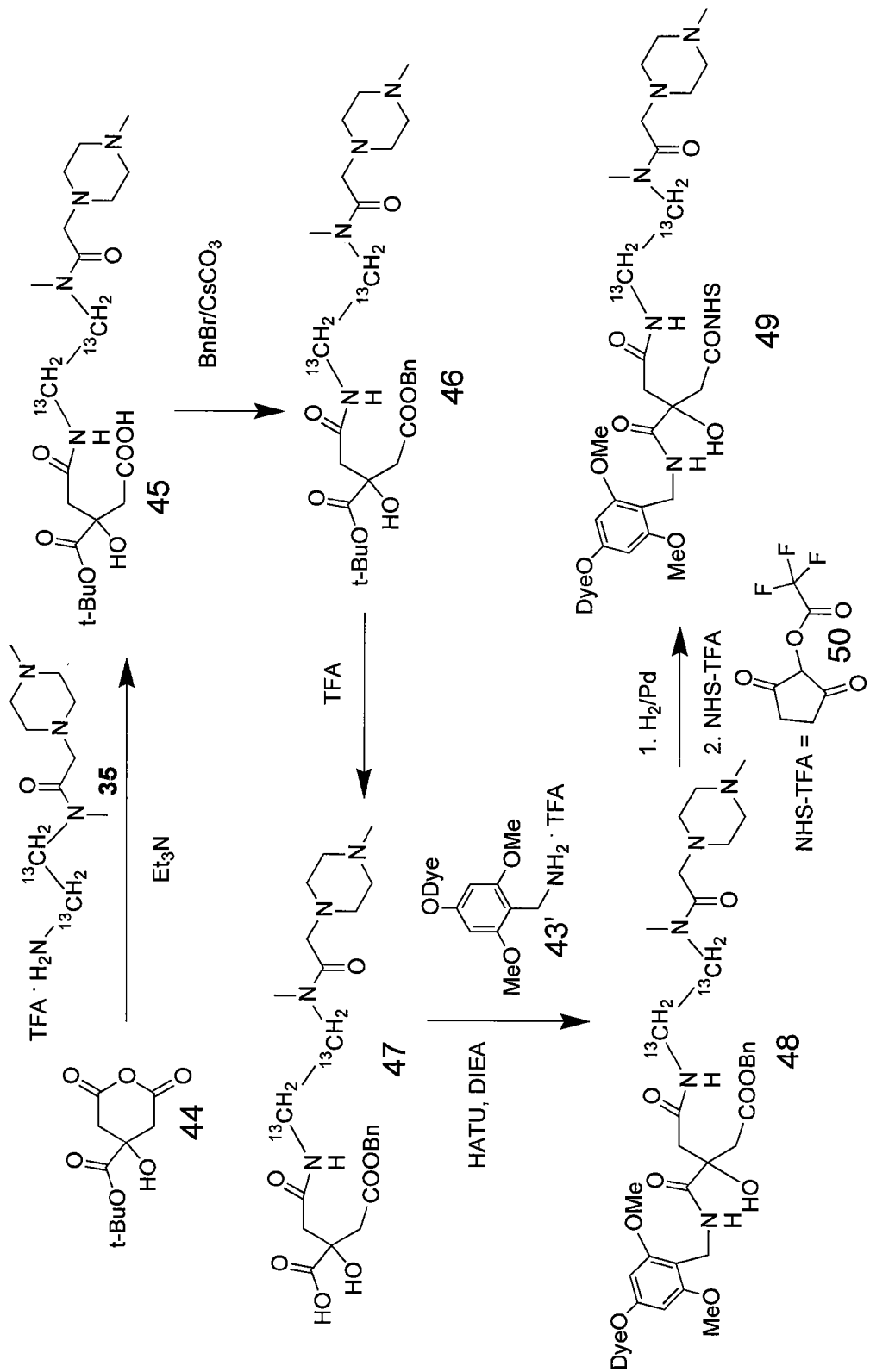
FIG. 13b illustrates the remaining part (with respect to FIG. 13a) of a prophetic synthetic route to a representative labeling reagent.
Figure 14:
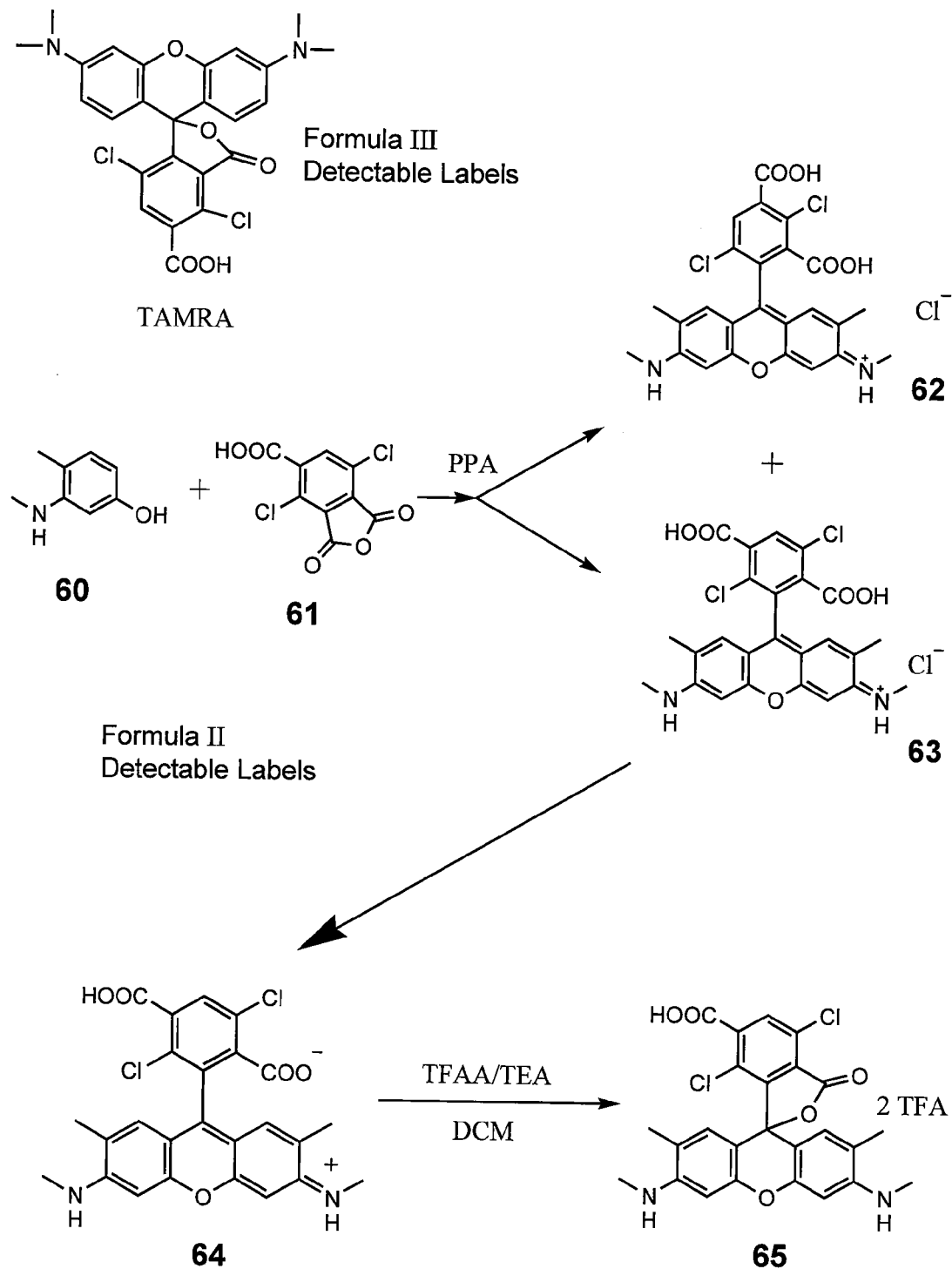
FIG. 14 illustrates a proposed synthetic route to Non-Encoded Detectable Labels

With reference to FIGS. 13 and 14, an alternative synthetic route to the labeling reagents is illustrated wherein the linker that cleavably links the non-encoded detectable label to the remainder of the labeling reagent is inverted as compared with the description in Example 1, above. With reference to FIG. 13a, the fluorescent dye 40 (it is to be understood that one could choose the fluorescent dye that leads to compounds of formula II as disclosed herein) is reacted with compound 41 in the presence of dicyclohexylcarbodiimide (DCC) to thereby produce compound 42. The tert-butyloxycarbonyl (t-boc or Boc) group of compound 42 is then removed by treatment with trifluoroacetic acid (TFA) to thereby produce compound 43 as its TFA salt. With reference to FIG. 13a, compound 43 is also illustrated in a shorthand form as compound 43' which from is used in the illustration in FIG. 14.

With reference to FIG. 13b, compound 44 (which can be prepared according to: Fadeev, Evgeny A.; Luo, Minkui; Groves, John T. *Synthesis and structural modeling of the amphiphilic siderophore rhizobactin-1021 and its analogs*. Bioorganic & Medicinal Chemistry Letters (2005), 15(16), 3771-3774) is reacted with compound 35 (it is to be understood that depending on the desired reagent, various encoded versions or a non-encoded version of compound 35 can be used) in the presence of a non-nucleophilic organic base, such as triethylamine ($Et_3N$) or N,N'-diisopropylethylamine (DIEA), to thereby produce compound 45. Compound 45 is reacted with benzyl bromide (BnBr) in the presence of the inorganic base; cesium carbonate ($CsCO_3$) to thereby form compound 46. The t-boc group of compound 46 is then removed by treatment with TFA to thereby produce compound 47. Compound 47 is then reacted treated with HATU in the presence of a non-nucleophilic organic base, such as DIEA, and then reacted with compound 43' to thereby produce compound 48. Compound 48 is then treated with hydrogen ($H_2$) and Palladium (Pd) catalyst to thereby convert the benzyl ester to a carboxylic acid group which is reacted with N-hydroxysuccinimidyl-triflouroacetate (NHS-TFA, compound 50) to thereby form the NHS-ester of the labeling reagent 49.

Example 4

Proposed Synthetic Route to Non-Encoded Detectable Labels

The fluorescent dyes used as non-encoded detectable labels can be available dyes and/or dyes that are modified from commercially available dyes. For example, with reference to FIG. 14, the compositions disclosed herein with the general formula III, comprise TAMRA moiety, wherein TAMRA is a dye commercially available from various sources.

In order to prepare a fluorescent dye comprising the same mass and charge as TAMRA, FIG. 14 also illustrates a proposed synthetic route to the dye used with respect to compounds with general formula II. The proposed synthesis follows a well known synthetic pathway wherein an N-ethyl version of phenolic compound is substituted with its N-methyl derivative 60 to thereby produce the desired dye 65 as its bis-TFA salt.

With reference to FIG. 14, dye 65 can be prepared by treating a mixture of compound 60 and 61 with polyphosphoric acid under high temperature for an extended period of time. Those of skill in the art of fluorescent dye manufacture will appreciate how to perform this meld. The reaction produces compounds 62 and 63, wherein compound 63 is isolated and converted to salt form 64. Compound 64 can then be treated with trifluoroacetic acid/triethylamine to thereby produce the bis-trifluoroactate 65.

While the present teachings are described in conjunction with various embodiments, it is not intended that the present teachings be limited to such embodiments. On the contrary, the present teachings encompass various alternatives, modifications and equivalents, as will be appreciated by those of skill in the art.

We claim:
1. The compound:
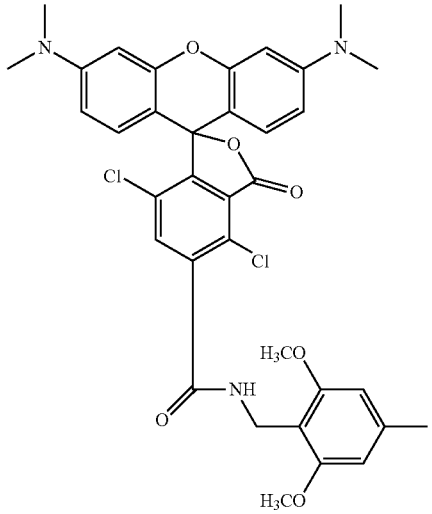
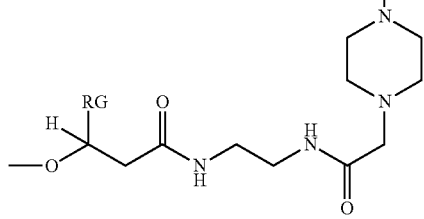
and any salt form thereof, wherein:
RG is:
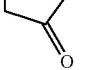
and wherein X' is O or S and each X" is independently of the other F, Cl, Br or I.
2. The compound:
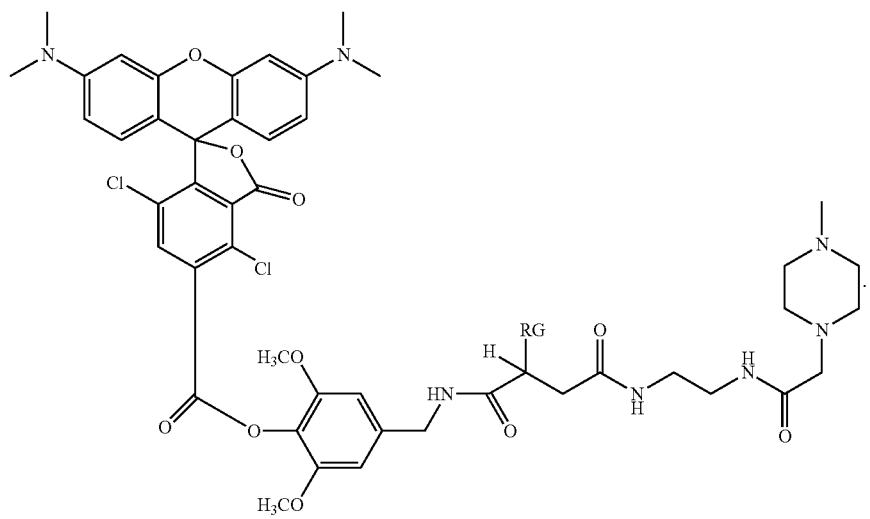

and any salt form thereof, wherein:
RG is:
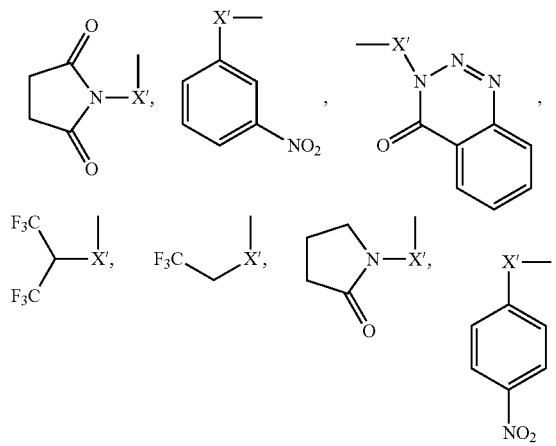
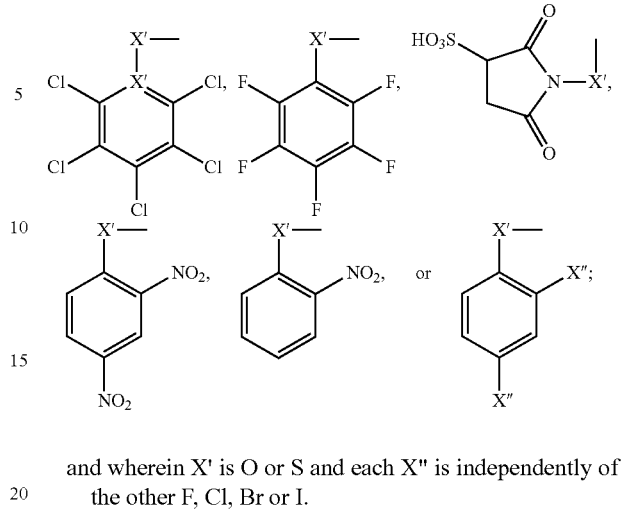
and wherein X' is O or S and each X" is independently of the other F, Cl, Br or I.
* * * * *